(12) United States Patent
Asada et al.

(10) Patent No.: US 11,479,550 B2
(45) Date of Patent: Oct. 25, 2022

(54) EP4 ANTAGONIST

(71) Applicant: ONO PHARMACEUTICAL CO., LTD., Osaka (JP)

(72) Inventors: Masaki Asada, Osaka (JP); Kousuke Tani, Osaka (JP); Satonori Higuchi, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 45 days.

(21) Appl. No.: 16/614,877

(22) PCT Filed: May 21, 2018

(86) PCT No.: PCT/JP2018/019440
§ 371 (c)(1),
(2) Date: Nov. 19, 2019

(87) PCT Pub. No.: WO2018/216640
PCT Pub. Date: Nov. 29, 2018

(65) Prior Publication Data
US 2021/0163466 A1 Jun. 3, 2021

(30) Foreign Application Priority Data

May 22, 2017 (JP) .............................. JP2017-100512

(51) Int. Cl.
| | | |
|---|---|---|
| *A61P 43/00* | (2006.01) | |
| *A61P 37/00* | (2006.01) | |
| *C07D 413/12* | (2006.01) | |
| *C07D 403/12* | (2006.01) | |
| *C07D 403/14* | (2006.01) | |
| *C07D 417/12* | (2006.01) | |
| *C07D 209/08* | (2006.01) | |
| *C07D 401/12* | (2006.01) | |
| *C07D 405/12* | (2006.01) | |
| *A61K 45/06* | (2006.01) | |

(52) U.S. Cl.
CPC ............ *C07D 417/12* (2013.01); *A61K 45/06* (2013.01); *C07D 401/12* (2013.01); *C07D 403/12* (2013.01); *C07D 403/14* (2013.01); *C07D 405/12* (2013.01); *C07D 413/12* (2013.01)

(58) Field of Classification Search
CPC .......... A61P 43/00; A61P 37/00; A61K 45/06; C07D 413/12; C07D 403/12; C07D 403/14; C07D 417/12; C07D 209/08; C07D 401/12; C07D 405/12
See application file for complete search history.

(56) References Cited

U.S. PATENT DOCUMENTS

| | | | |
|---|---|---|---|
| 2015/0094330 A1 | 4/2015 | Donde et al. | |
| 2017/0128431 A1 | 5/2017 | Ikegami et al. | |
| 2018/0002308 A1 | 1/2018 | Asada et al. | |

FOREIGN PATENT DOCUMENTS

| | | |
|---|---|---|
| EP | 1258473 A1 | 11/2002 |
| EP | 1312601 A1 | 5/2003 |
| EP | 1431267 A1 | 6/2004 |
| EP | 2 740 475 A1 | 6/2014 |
| WO | 01/62708 A1 | 8/2001 |
| WO | 02/16311 A1 | 2/2002 |
| WO | 03/016254 A1 | 2/2003 |
| WO | 2016/088903 A1 | 6/2016 |
| WO | 2016/111347 A1 | 7/2016 |

OTHER PUBLICATIONS

Adprevention, 2021,https://www.alz.org/alzheimers-dementia/research_progress/prevention.*
Cancerprevention, 2021,https://www.cancerresearchuk.org/about-cancer/causes-of-cancer/can-cancer-be-prevented-0.*
EP4Antagonist, 2021, https://en.wikipedia.org/wiki/Prostaglandin_EP4_receptor.*
Hong et al., J Immunother, 2020, 8, 1-12.*
Chandrasekar, 2017, 3, 3 pages.*
Marsumoto et al., 2019, 9, 12 pages.*
Cudaback et al., 2014, 88, 565-572.*
Bay-1316957, 2022, https://www.immune-system-research.com/autoimmune-disorders/encephalomyelitis-autoimmune-disorders/bay-1316957-is-a-selective-and-orally-active-ep4-r-antagonist/2021-03-24/.*
Li Yang et al., "Host and Direct Antitumor Effects and Profound Reduction in Tumor Metastasis with Selective EP4 Receptor Antagonism", American Association for Cancer Research, vol. 66, No. 19, DOI: 10.1158/0008-5472.CAN-06-1271, Oct. 1, 2006, pp. 9665-9672, 8 pages total, XP002659219.
International Search Report (PCT/ISA/210), issued by International Searching Authority in corresponding International Application No. PCT/JP2018/019440, dated Aug. 21, 2018.

(Continued)

*Primary Examiner* — Sun Jae Yoo
(74) *Attorney, Agent, or Firm* — Sughrue Mion, PLLC

(57) ABSTRACT

A compound represented by general formula (I):

$$(R^2)_p - B \overset{A-R^1}{\underset{L^1}{\diagdown}} \overset{L^2}{\underset{C}{\diagdown}} \overset{(R^3)_n}{\underset{(R^4)_m}{}} \quad \text{(I)}$$

(wherein in the formula, all the symbols have the same meanings as those described in the specification), or a pharmaceutically acceptable salt thereof is useful as a medicament's active ingredient having an $EP_4$ receptor antagonistic activity, in preventing and/or treating disease caused by activation of an $EP_4$ receptor.

12 Claims, No Drawings

(56) References Cited

OTHER PUBLICATIONS

Written Opinion (PCT/ISA/237) issued by the International Searching Authority in corresponding International Application No. PCT/JP2018/019440, dated Aug. 21, 2018.

* cited by examiner

EP4 ANTAGONIST

TECHNICAL FIELD

The present invention relates to a compound having an EP$_4$ receptor antagonistic activity or a salt thereof, and a medicament containing the compound or the salt thereof as an active ingredient. The present invention particularly relates to a compound represented by the general formula (I):

[Chem. 1]

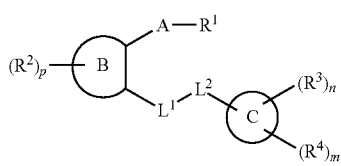

(wherein in the formula, all the symbols have the same meanings as given below), or a pharmaceutically acceptable salt thereof (hereinafter, referred to as a compound of the present invention), and a medicament containing thereof as an active ingredient.

BACKGROUND ART

The prostaglandin E$_2$ (PGE$_2$), a known metabolite of the arachidonic acid cascade, is known to have a range of effects including cytoprotection, uterine contraction, lowering of the threshold of pain, promotion of peristalsis in the digestive tract, wakefulness, inhibition of stomach acid secretion, hypotensive effect, and diuretic effect.

Recent studies have found that there are subtypes of PGE$_2$ receptors with different roles. To date, four broad subtypes are known, and these are called EP$_1$, EP$_2$, EP$_3$, and EP$_4$ (Journal of Lipid Mediators and Cell Signalling, Vol. 12, p. 379-391, 1995).

In these subtypes, the EP$_4$ receptor is thought to be involved in inhibition of MCP-1 production from macrophages, inhibition of TNF-α, IL-2, and IFN-γ production from lymphocytes. This EP$_4$ receptor is also believed to have involvement in anti-inflammation by enhanced IL-10 production, vasodilatation, angiogenesis, inhibition of elastic fiber formation, and regulation of MMP-9 expression. Other possible involvement of the EP$_4$ receptor includes immune control in cancer via myeloid derived suppressor cells, regulatory T cells, and natural killer cells.

It is therefore thought that compounds that strongly bind to the EP4 receptor, and show antagonistic activity are useful for the prevention and/or treatment of diseases caused by EP4 receptor activation, including, for example, a bone disease, a cancer, a systemic granulomatous disease, an immune disease, allergy, atopy, asthma, alveolar pyorrhea, gingivitis, periodontitis, Alzheimer's, Kawasaki disease, burn, multiple organ failure, chronic headache, pain, vasculitis, venous incompetence, varicose veins, aneurysm, aortic aneurysm, anal fistula, diabetes insipidus, stress, endometriosis, uterine adenomyosis, patent ductus arteriosus in neonates, and cholelithiasis (Pharmacological Reviews, Vol. 65, p. 1010-1052, July, 2013; 105th Annual Meeting of American Association for Cancer Research (AACR), Abstract: LB-265, Title of Presentation: ONO-AE3-208 Inhibits Myeloid Derived Suppressor Cells and Glioma Growth, Date of Presentation: Apr. 8, 2014; FEBS Letters, Vol. 364, p. 339-341, 1995; Cancer Science, Vol. 105, p. 1142-1151, 2014; Cancer Research, Vol. 70, p. 1606-1615, 2010; and Cancer Research, Vol. 62, p. 28-32, 2002).

On the other hand, Patent Literature 1 describes use of compounds represented by the general formula (A) as compounds used for treatment of diseases related to a prostaglandin E receptor, for example, pain, inflammation, cancer, and the like.

The general formula (A) is:

[Chem. 2]

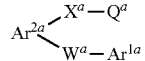

(wherein in the formula, Ar$^{1a}$ is an aryl or heteroaryl group, which is occasionally substituted with R$^{1a}$ or R$^{3a}$;
R$^{1a}$ is CN, NO$_2$, CON(R$^{5a}$)$_2$, or the like;
R$^{3a}$ is a halogen atom, CN, or the like;
W$^a$ represents a 3- to 6-membered binding group including 0 to 2 heteroatoms selected from O, N, and S, wherein the binding group occasionally includes CO, S(O)$_{na}$, C=C, or an acetylene group;
Ar$^{2a}$ is an aryl or heteroaryl group, which is occasionally substituted with R$^{3a}$;
X$^a$ is a linker bonded to Ar$^{2a}$ at the position ortho to a binding site of W$^a$; and
Q$^a$ is COOH or the like (the definitions of the groups are partially excerpted)).

Furthermore, Patent Literature 2 mentions that compounds represented by the following general formula (B) are useful for the prevention and/or treatment of diseases such as pain and cancer because they are bonded to a PGE$_2$ receptor, in particular, to EP$_3$ and/or EP$_4$, and have an antagonistic effect.

The general formula (B) is:

[Chem. 3]

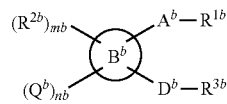

(wherein in the formula, R$^{1b}$ is —COOH, or the like;
A$^b$ represents (i) a single bond, (ii) C1-6 alkylene, (iii) C2-6 alkenylene, or (iv) C2-6 alkynylene, or the like;
a B$^b$ ring represents a C3-12 monocyclic or bicyclic carbon ring, or a 3- to 12-membered monocyclic or bicyclic heterocycle;
R$^{2b}$ represents a halogen atom, nitro, cyano, or the like;
Q$^b$ represents —(1-4 alkylene)-Cyc2$^b$, —(1-4 alkylene)-Z$^b$-Cyc3$^b$, cyano, nitro, or the like;
Z$^b$ represents —O— or the like;
Cyc2$^b$ represents C3-15 monocyclic, bicyclic, or tricyclic carbon ring, or 3- to 15-membered monocyclic, bicyclic, or tricyclic heterocycle substituted with 1 to 5 R$^{30b}$ or unsubstituted;
Cyc3$^b$ represents C3-15 monocyclic, bicyclic, or tricyclic carbon ring, or 3- to 15-membered monocyclic, bicyclic, or tricyclic heterocycle substituted with 1 to 5 R$^{30b}$ or unsubstituted;

$D^b$ represents a linking chain including 3- to 6-membered atoms selected from a carbon atom, a nitrogen atom, an oxygen atom, and a sulfur atom, and the chain may include a double bond or a triple bond, or the linking chain may be substituted with 1 to 12 $R^{40b}$s;

$R^{40b}$ represents oxo, halogen, or the like;

$R^{3b}$ represents (1) C1-6 alkyl, or (2) C3-15 monocyclic, bicyclic, or tricyclic carbon ring or 3- to 15-membered monocyclic, bicyclic, or tricyclic heterocycle, substituted with 1 to 5 $R^{42b}$s or unsubstituted;

$R^{42b}$ represents C1-6 alkyl, C1-6 alkoxy, a halogen atom, cyano, $-NR^{46b}COR^{47b}$, $Cyc10^b$, or $-CO-Cyc10^b$ (the definitions of the groups are partially excerpted)).

Furthermore, Patent Literature 3 describes use of compounds represented by the following general formula (C) as compounds to be used for treatment of diseases related to a prostaglandin E receptor, for example, pain, inflammation, cancer, and the like.

The general formula (C) is:

[Chem. 4]

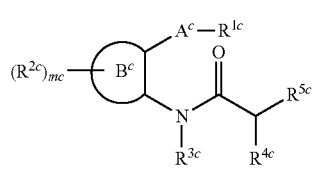

(c)

(wherein in the formula, $R^{1c}$ represents COOH or the like; $A^c$ is C1-6 alkylene or the like;

$R^{2c}$ is a C1-6 alkyl group, a cyano group, or the like;

$B^c$ ring represents a C5-7 monocyclic carbon ring or the like;

$R^{3c}$ represents a hydrogen atom or a C1-4 alkyl group, or the like;

$R^{4c}$ represents (1) a C1-8 alkyl, (2) a C2-8 alkenyl, or the like;

$R^{5c}$ represents C5-10 monocyclic or bicyclic carbon ring or at least one nitrogen atom, and 5- to 10-membered monocyclic or bicyclic heterocycle containing a heteroatom selected from an oxygen atom or a sulfur atom, substituted with 1 to 2 $R^{13c}$ groups or unsubstituted;

$R^{13c}$ represents C1-6 alkyl, C1-6 alkoxy, a halogen atom, $CF_3$, or the like;

when two $R^{13c}$s are present, both may be the same as or different from each other, (the definitions of the groups are partially excerpted)).

PRIOR ART LITERATURES

Patent Literatures

[Patent Literature 1] WO2000/020371
[Patent Literature 2] WO2003/016254
[Patent Literature 3] WO2002/016311

Non-Patent Literatures

[Non-Patent Literature 1] Journal of Lipid Mediators and Cell Signaling, Vol. 12, p 379-391, 1995
[Non-Patent Literature 2] Pharmacological Reviews, Vol. 65, p. 1010-1052, July, 2013
[Non-Patent Literature 3] 105th Annual Meeting of American Association for Cancer Research (AACR), Abstract: LB-265, Title of Presentation: ONO-AE3-208 Inhibits Myeloid Derived Suppressor Cells and Glioma Growth, Date of Presentation: Apr. 8, 2014
[Non-Patent Literature 4] FEBS Letters, Vol. 364, p. 339-341, 1995
[Non-Patent Literature 5] Cancer Science, Vol. 105, p. 1142-1151, 2014
[Non-Patent Literature 6] Cancer Research, Vol. 70, p. 1606-1615, 2010
[Non-Patent Literature 7] Cancer Research, Vol. 62, p. 28-32, 2002

SUMMARY OF INVENTION

Technical Problem

A problem to be solved by the present invention is to find a compound having a strong antagonistic activity with respect to an $EP_4$ receptor, and being useful as preventive and/or therapeutic drug for diseases caused by activation of the $EP_4$ receptor.

Solution to Problem

In order to solve the above-mentioned problem, the inventors of the present invention have keenly studied to find a compound having a strong antagonistic activity with respect to an $EP_4$ receptor. As a result, the inventors have found that a compound represented by the general formula (I) mentioned later strongly antagonizes $EP_4$ receptor, and have selectivity with respect to other EP receptors, and completed the present invention.

In other words, the present invention is as follows.

[1] A compound represented by the general formula (I), or a pharmaceutically acceptable salt thereof:

[Chem. 5]

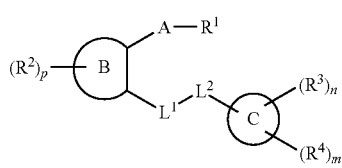

(I)

(wherein in the formula, $R^1$ represents $COOR^5$, tetrazole, $SO_3H$, $SO_2NH_2SO_2NHR^6$, $CONHSO_2R^7$, $SO_2NHCOR^8$, or hydroxamic acid, $R^5$ represents a hydrogen atom, C1-4 alkyl, or benzyl, $R^6$, $R^7$, and $R^8$ each independently represent C1-4 alkyl, a C3-10 carbon ring, or a 3- to 10-membered heterocycle, C1-4 alkyl, benzyl, a C3-10 carbon ring, and a 3- to 10-membered heterocycle in $R^5$, $R^6$, $R^7$, and $R^8$, each independently may be substituted with 1 to 5 $R^9$s, $R^9$ represents a halogen atom, C1-4 alkyl, C1-4 alkoxy, C1-4 alkylthio, or cyano, when two or more $R^9$s are present, a plurality of $R^9$'s may be the same as or different from each other, respectively, C1-4 alkyl, C1-4 alkoxy, and C1-4 alkylthio in $R^9$ may be substituted with a halogen atom, A represents C1-5 alkylene, C2-5 alkenylene, C2-5 alkynylene, $-(C1-3\ alkylene)-G^1-(C1-3\ alkylene)-$, $-G^1-(C1-5\ alkylene)-$, $-(C1-3\ alkylene)-(5-\ to\ 6-membered\ aromatic\ ring)-$, or $-G^1-(5-\ to\ 6-membered\ aromatic\ ring)-$, $G^1$ represents $-O-$, $-S-$, or $-NR^{10}-$, $R^{10}$ represents a hydrogen atom, C1-4 alkyl, or C2-5 acyl, A may be substituted with 1 to 5 substituents which may be the same as or different from each other, and the substituent is selected from a halogen atom or C1-4 alkyl, ring B represents a C5-10 carbon ring or a 5- to 10-membered heterocycle, $R^2$ represents a halogen atom, nitro, cyano, a hydroxyl group, mercapto (—H), oxo, thioxo(=S), carboxyl, C1-4 alkyl, C2-4 alkenyl, C2-4 alkynyl, C1-4 alkoxy, C1-4 alkylthio, —C(O)$R^{101}$, —SO$_2$$R^{102}$, —CONR$^{103}$$R^{104}$, —NR$^{105}$C(O)$R^{106}$—NR$^{107}$SO$_2$$R^{108}$, —SO$_2$NR$^{109}$$R^{110}$, —NR$^{111}$$R^{112}$, or -L$^3$-R$^{11}$, $R^{101}$, $R^{102}$, $R^{103}$, $R^{104}$, $R^{105}$, $R^{106}$, $R^{107}$, $R^{108}$, $R^{109}$, $R^{110}$, $R^{111}$, and $R^{112}$ each independently represent a hydrogen atom, C1-4 alkyl, C2-4 alkenyl, C2-4 alkynyl, a C3-10 carbon ring, or a 3- to 10-membered heterocycle, C1-4 alkyl, C2-4 alkenyl, C2-4 alkynyl, C1-4 alkoxy, C1-4 alkylthio, a C3-10 carbon ring, and a 3- to 10-membered heterocycle in $R^2$, $R^{101}$, $R^{102}$, $R^{103}$, $R^{104}$, $R^{105}$, $R^{106}$, $R^{107}$, $R^{108}$, $R^{109}$, $R^{110}$, $R^{111}$, and $R^{112}$ each independently may be substituted with a halogen atom, a hydroxyl group, cyano, C1-4 alkyl, C1-4 alkoxy, C1-4 alkylthio, —NR$^{113}$R$^{114}$, a C3-10 carbon ring, -G$^2$-(C3-10 carbon ring), a 3- to 10-membered heterocycle, or a -G$^2$-(3- to 10-membered heterocycle), $G^2$ represents —CH$_2$—, —O—, —S—, or —NR$^{115}$—, $R^{113}$, $R^{114}$, and $R^{115}$ each independently represent a hydrogen atom, C1-4 alkyl, or C2-5 acyl, $L^3$ represents a bond, —CR$^{12}$R$^{13}$—, —O—, —CR$^{14}$(OR$^{15}$)—, —C(O)—, —NR$^{16}$—, —CR$^{17}$R$^{18}$O—, —CR$^{19}$R$^{20}$NR$^{21}$—, —CR$^{22}$R$^{23}$NR$^{24}$CO—, —C(O)NR$^{25}$—, or —S(O)$_s$—, s represents an integer of 0 to 2, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ each independently represent a hydrogen atom, or C1-4 alkyl, $R^{11}$ represents a C3-10 carbon ring or a 3- to 10-membered heterocycle optionally substituted with 1 to 5 $R^{26}$s, $R^{26}$ represents a halogen atom, a hydroxyl group, a mercapto, oxo, thioxo, —NR$^{27}$R$^{28}$, nitro, cyano, carboxyl, C1-4 alkyl, C2-4 alkenyl, C2-4 alkynyl, C1-4 alkoxy, C1-4 alkylthio, C2-5 acyl, —SO$_2$NR$^{29}$R$^{30}$, a C3-10 carbon ring, a -G$^3$-(C3-10 carbon ring), 3- to a 10-membered heterocycle, or a -G$^3$-(3- to 10-membered heterocycle), $G^3$ represents —CH$_2$—, —O—, —S—, or —NR$^{31}$—, $R^{27}$, $R^{28}$, $R^{29}$, $R^{30}$, and $R^{31}$ each independently represent a hydrogen atom, C1-4 alkyl, or C2-5 acyl, C1-4 alkyl, C2-4 alkenyl, C2-4 alkynyl, C1-4 alkoxy, C1-4 alkylthio, C2-5 acyl, a C3-10 carbon ring, a -G$^3$-(C3-10 carbon ring), a 3- to 10-membered heterocycle, or a -G$^3$-(3- to 10-membered heterocycle) in $R^{26}$, $R^{27}$, $R^{28}$, $R^{29}$, $R^{30}$, and $R^{31}$ may be substituted with a halogen atom, when a plurality of $R^{26}$'s are present, they may be the same as or different from each other, respectively, p represents an integer of 1 to 4, when p is two or more, a plurality of $R^2$'s may be the same as or different from each other, $L^1$ represents —CH$_2$CH$_2$, —CH=CH—, —CH$_2$O—, —CH$_2$S—, —CH$_2$S(O)—, —CH$_2$SO$_2$—, —CH$_2$NR$^{32}$—, —NR$^{33}$CO—, or —NR$^{34}$SO$_2$—, $R^{32}$, $R^{33}$, and $R^{34}$, each independently, a hydrogen atom, or C1-4 alkyl, $L^2$ represents —(CR$^{35}$R$^{36}$)u-, u represents an integer of 0 to 2, $R^{35}$ and $R^{36}$ each independently represent a hydrogen atom or C1-4 alkyl, C1-4 alkyl in $R^{35}$ and $R^{36}$ may be substituted with a halogen atom or a hydroxyl group, when u is two, $R^{35}$ and $R^{36}$ each independently may be the same as or different from each other, $R^{35}$ and $R^{36}$ may be bonded to each other to form a C3-8 saturated carbon ring, ring C represents a C6-10 aromatic carbon ring or a 5- to 10-membered aromatic heterocycle, $R^3$ represents a halogen atom, nitro, cyano, a hydroxyl group, mercapto, oxo, thioxo, carboxyl, C1-4 alkyl, C2-4 alkenyl, C2-4 alkynyl, C1-4 alkoxy, C1-4 alkylthio, a C3-8 saturated carbon ring, a 3- to 8-membered saturated heterocycle, —C(O)R$^{201}$, —SO$_2$R$^{202}$, —CONR$^{203}$R$^{204}$, —NR$^{205}$C(O)R$^{206}$, —NR$^{207}$SO$_2$R$^{208}$, —SO$_2$NR$^{209}$R$^{210}$, or —NR$^{211}$R$^{212}$, $R^{201}$, $R^{202}$, $R^{203}$, $R^{204}$, $R^{205}$, $R^{206}$, $R^{207}$, $R^{208}$, $R^{209}$, $R^{210}$, $R^{211}$, and $R^{212}$, each independently represent a hydrogen atom, C1-4 alkyl, C2-4 alkenyl, C2-4 alkynyl, a C3-10 carbon ring, or a 3- to 10-membered heterocycle, C1-4 alkyl, C2-4 alkenyl, C2-4 alkynyl, C1-4 alkoxy, C1-4 alkylthio, a C3-8 saturated carbon ring, a 3- to 8-membered saturated heterocycle, a C3-10 carbon ring, and a 3- to 10-membered heterocycle in $R^3$, $R^{201}$, $R^{202}$, $R^{203}$, $R^{204}$, $R^{205}$, $R^{206}$, $R^{207}$, $R^{208}$, $R^{209}$, $R^{210}$, $R^{211}$, and $R^{212}$, each independently may be substituted with a halogen atom, a hydroxyl group, cyano, C1-4 alkyl, C1-4 alkoxy, C1-4 alkylthio, —NR$^{37}$R$^{38}$, a C3-10 carbon ring, a -G$^4$-(C3-10 carbon ring), a 3- to 10-membered heterocycle, or a -G$^4$-(3- to 10-membered heterocycle), $G^4$ represents —CH$_2$—, —O—, —S—, or —NR$^{115}$—, $R^{37}$ and $R^{38}$ each independently represent a hydrogen atom, C1-4 alkyl or C2-5 acyl, $R^3$ which is not on a bonding atom between $L^2$ and ring C may be bonded to $R^{35}$ or $R^{36}$ to form a C3-6 carbon ring, n represents an integer of 0 to 5, when n is two or more, a plurality of $R^3$'s may be the same as or different from each other, $R^4$ represents a halogen atom, a hydroxyl group, mercapto, oxo, thioxo, cyano, nitro, carboxyl, C1-4 alkyl, C2-4 alkenyl, C2-4 alkynyl, C1-4 alkoxy, C1-4 alkylthio, —CONR$^{41}$R$^{42}$, —NR$^{43}$COR$^{44}$, —C(O)R$^{45}$, —OR$^{46}$, —S(O)$_t$R$^{47}$—NR$^{48}$R$^{49}$, a C3-10 carbon ring, a -G$^5$-(C3-10 carbon ring), a 3- to 10-membered heterocycle, or a -G$^5$-(3- to 10-membered heterocycle), $G^5$ represents —CH$_2$—, —O—, —S—, or —NR$^{116}$—, t represents an integer of 0 to 2, $R^{116}$ represents a hydrogen atom, C1-4 alkyl or C2-5 acyl, $R^{41}$, $R^{42}$, $R^{43}$, $R^{44}$, $R^{45}$, $R^{46}$, $R^{47}$, $R^{48}$, and $R^{49}$ each independently represent a hydrogen atom, C1-6 alkyl, C2-6 alkenyl, C2-6 alkynyl, a C3-10 carbon ring, or a 3- to 10-membered heterocycle, C1-6 alkyl, C2-6 alkenyl, C2-6 alkynyl, a C3-10 carbon ring, and a 3- to 10-membered heterocycle in $R^{41}$, $R^{42}$, $R^{43}$, $R^{44}$, $R^{45}$, $R^{46}$, $R^{47}$, $R^{48}$, and $R^{49}$ may be substituted with 1 to 6 $R^{50}$s, $R^{50}$ represents a halogen atom, a hydroxyl group, oxo, thioxo, cyano, nitro, —NR$^{51}$R$^{52}$, C1-6 alkoxy, C1-6 alkylthio, C3-10 carbon ring, G$^6$-(C3-10 carbon ring), a 3- to 10-membered heterocycle, or a -G$^6$-(3- to 10-membered heterocycle), when two or more $R^{50}$ are present, $R^{50}$s may be the same as or different from each other, $G^6$ represents —CH$_2$—, —O—, —S—, or —NR$^{53}$—, $R^{51}$, $R^{52}$ and $R^{53}$, each independently represent a hydrogen atom, C1-4 alkyl or C2-5 acyl, $R^{41}$ and $R^{42}$, $R^{48}$ and $R^{49}$, $R^{51}$ and $R^{52}$ each independently may form a 3- to 8-membered saturated heterocycle together with nitrogen atoms bonded thereto, m represents an integer of 0 to 5, when m is two or more, a plurality of $R^4$'s may be the same as or different from each other).

[2] The compound according to [1], or a pharmaceutically acceptable salt thereof, wherein m is an integer of 1 to 4, at least one $R^4$ is (1) —$CONR^{41}R^{42}$, or (2) —$C(O)R^{45}$ (wherein $R^{45}$ represents C1-6 alkyl, C2-6 alkenyl, or C2-6 alkynyl).

[3] The compound according to [1] or [2], or a pharmaceutically acceptable salt thereof, wherein the ring B is benzene or a 5- to 6-membered aromatic heterocycle.

[4] The compound according to any one of [1] to [3], or a pharmaceutically acceptable salt thereof, wherein the ring C is a bicyclic C9-10 aromatic carbon ring, or a bicyclic 9- to 10-membered aromatic heterocycle.

[5] The compound according to [1], or a pharmaceutically acceptable salt thereof, which is represented by the general formula (I-0):

[Chem. 6]

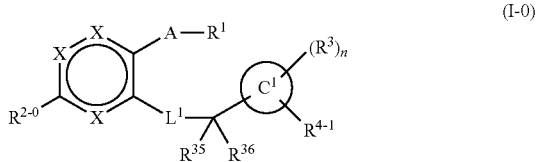

(I-0)

(wherein in the formula,
X is $CR^{2-2}$, or N, wherein each X may be the same as or different from each other,
$R^{2-0}$ represents $R^2$ ($R^2$ has the same meaning as defined in the above [1], except for oxo and thioxo),
$R^{2-2}$ represents a hydrogen atom or $R^2$ ($R^2$ has the same meaning as defined in the above [1], except for oxo and thioxo),
when a plurality of $R^{2-2}$'s is present, each $R^{2-2}$'s may be the same as or different from each other,
$R^{4-1}$ represents —$CONR^{41}R^{42}$ or —$C(O)R^{45-1}$,
$R^{45-1}$ represents C1-6 alkyl, C2-6 alkenyl, C2-6 alkynyl,
ring $C^1$ represents a bicyclic C9-10 aromatic carbon ring or a bicyclic 9- to 10-membered aromatic heterocycle, and the other symbols have the same meanings as defined in the above [1]).

[6] The compound according to [1], or a pharmaceutically acceptable salt thereof, which is represented by the general formula (I-1)

[Chem. 7]

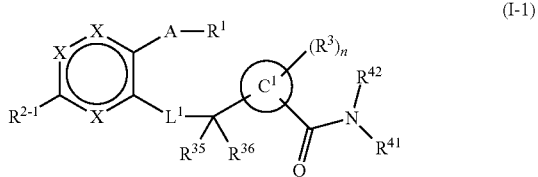

(I-1)

(wherein in the formula,
X is $CR^{2-2}$, or N, wherein each X may be the same as or different from each other,
$R^{2-2}$ represents a hydrogen atom or $R^2$ ($R^2$ has the same meaning as defined in the above [1], except for oxo and thioxo),
when a plurality of $R^{2-2}$'s is present, each $R^{2-2}$'s may be the same as or different from each other, $R^{2-1}$ represents a halogen atom, cyano, -$L^3$-$R^{11}$ ($L^3$ and $R^{11}$ have the same meanings as defined in the above [1]),
ring $C^1$ represents a bicyclic C9-10 aromatic carbon ring or a bicyclic 9- to 10-membered aromatic heterocycle, and the other symbols have the same meanings as defined in the above [1]).

[7] The compound according to [5] or [6], or a pharmaceutically acceptable salt thereof, wherein the ring $C^1$ is indole.

[8] The compound according to any one of [1] to [7], or a pharmaceutically acceptable salt thereof, wherein $L^1$ is —NHCO—.

[9] The compound according to any one of [6] to [8], or a pharmaceutically acceptable salt thereof, wherein $R^{41}$ is C1-6 alkyl, C2-6 alkenyl, C2-6 alkynyl, a C3-10 carbon ring, or a 3- to 10-membered heterocycle, which is substituted with one or more $R^{50}$'s ($R^{50}$ has the same meaning as defined in the above [1]) (excluding a compound in which $R^{41}$ is $CHF_2$, $CF_3$, or benzyl).

[10] The compound according to any one of [6] to [8], or a pharmaceutically acceptable salt thereof, wherein $R^{41}$ is C1-6 alkyl, C2-6 alkenyl, C2-6 alkynyl, a C3-10 carbon ring, or a 3- to 10-membered heterocycle, which is substituted with a substituent selected from (1) a hydroxyl group, (2) oxo, (3) thioxo, (4) cyano, (5) nitro, (6) —$NR^{51}R^{52}$, (7) C1-6 alkoxy, (8) C1-6 alkylthio, (9)-$G^6$-(C3-10 carbon ring), (10) a 3- to 10-membered heterocycle, and (11) -$G^6$-(3- to 10-membered heterocycle).

[11] The compound according to any one of [6] to [8], or a pharmaceutically acceptable salt thereof, wherein $R^{2-1}$ is -$L^3$-$R^{11}$ (wherein $R^{11}$ represents 3- to 10-membered heterocycle which may be substituted with one to five $R^{26}$'s).

[12] The compound according to any one of [6] to [8], or a pharmaceutically acceptable salt thereof, wherein $R^{2-1}$ is —$C(O)NR^{25}$-$R^{11}$, $R^{11}$ is a C3-10 carbon ring or a 3- to 10-membered heterocycle, which is substituted with $R^{26}$,

[13] The compound according to [1], which is:
(1) 4-{4-[(3,5-dimethyl-1H-pyrazol-1-yl)methyl]-2-({2-[3-methyl-6-(methylcarbamoyl)-1H-indol-1-yl]propanoyl}amino)phenyl}butanoic acid,
(2) 4-[2-({2-[3-methyl-6-(methylcarbamoyl)-1H-indol-1-yl]propanoyl}amino)-4-{[5-methyl-3-(trifluoromethyl)-1H-pyrazol-1-yl]methyl}phenyl]butanoic acid,
(3) 4-{2-({2-[6-(ethylcarbamoyl)-3-methyl-1H-indol-1-yl]propanoyl}amino)-4-[(4-methyl-1H-pyrazol-1-yl)methyl]phenyl}butanoic acid,
(4) 4-{2-({2-[3-methyl-6-(propylcarbamoyl)-1H-indol-1-yl]propanoyl}amino)-4-[(4-methyl-1H-pyrazol-1-yl)methyl]phenyl}butanoic acid,
(5) 4-{2-({2-[6-(isopropylcarbamoyl)-3-methyl-1H-indol-1-yl]propanoyl}amino)-4-[(4-methyl-1H-pyrazol-1-yl)methyl]phenyl}butanoic acid,
(6) 4-{2-[(2-{6-[(2-methoxyethyl)carbamoyl]-3-methyl-1H-indol-1-yl}propanoyl)amino]-4-[(4-methyl-1H-pyrazol-1-yl)methyl]phenyl}butanoic acid,
(7) 4-{2-({2-[(6-(dimethylcarbamoyl)-3-methyl-1H-indol-1-yl]propanoyl}amino)-4-[(4-methyl-1H-pyrazol-1-yl)methyl]phenyl}butanoic acid,
(8) 4-{2-[(2-{6-[(cyclopropylmethyl)carbamoyl]-3-methyl-1H-indol-1-yl}propanoyl)amino]-4-[(4-methyl-1H-pyra-zol-1-yl)methyl]phenyl}butanoic acid,
(9) 4-{4-[(3-cyclopropyl-1H-1,2,4-triazol-1-yl)methyl]-2-({2-[3-methyl-6-(methylcarbamoyl)-1H-indol-1-yl]propanoyl}amino)phenyl}butanoic acid,
(10) 4-{4-[(4-fluoro-1H-pyrazol-1-yl)methyl]-2-({2-[3-methyl-6-(methylcarbamoyl)-1H-indol-1-yl]propanoyl}amino)phenyl}butanoic acid,

(11) 4-{4-[(4-isopropyl-1H-1,2,3-triazol-1-yl)methyl]-2-({2-[3-methyl-6-(methylcarbamoyl)-1H-indol-1-yl]propanoyl}amino)phenyl}butanoic acid,

(12) 4-(2-[(2-{6-[(2-methoxyethyl)carbamoyl]-3-methyl-1H-indol-1-yl}propanoyl]-4-{[3-(trifluoromethyl)-1H-1,2,4-triazol-1-yl]methyl}phenyl)butanoic acid,

(13) 4-[2-({2-[3-methyl-6-(methylcarbamoyl)-1H-indol-1-yl]propanoyl}amino)-4-{[3-(trifluoromethyl)-1H-1,2,4-triazol-1-yl]methyl}phenyl]butanoic acid,

(14) 4-{2-({2-[3-methyl-5-(methylcarbamoyl)-1H-indol-1-yl]propanoyl}amino)-4-[(4-methyl-1H-pyrazol-1-yl)methyl]phenyl}butanoic acid,

(15) 4-{2-({2-[5-(isopropylcarbamoyl)-3-methyl-1H-indol-1-yl]propanoyl}amino)-4-[(4-methyl-1H-pyrazol-1-yl)methyl]phenyl}butanoic acid,

(16) 4-{2-[(2-{5-[(2-methoxyethyl)carbamoyl]-3-methyl-1H-indol-1-yl}propanoyl)amino]-4-[(4-methyl-1H-pyrazol-1-yl)methyl]phenyl}butanoic acid,

(17) 4-{2-({2-[3-cyclopropyl-6-(methylcarbamoyl)-1H-indol-1-yl]propanoyl}amino)-4-[(4-methyl-1H-pyrazol-1-yl)methyl]phenyl}butanoic acid,

(18) 4-{2-[(2-{3-cyclopropyl-6-[(2-methoxyethyl)carbamoyl]-1H-indol-1-yl}propanoyl)amino]-4-[(4-methyl-1H-pyrazol-1-yl)methyl]phenyl}butanoic acid,

(19) 4-{4-cyano-2-[(2-{6-[(2-methoxyethyl)carbamoyl]-1H-indol-1-yl}propanoyl)amino]phenyl}butanoic acid,

(20) 4-[4-cyano-2-({2-[6-(ethylcarbamoyl)-3-methyl-1H-indol-1-yl]propanoyl}amino)phenyl]butanoic acid,

(21) 4-[4-cyano-2-({2-[3-methyl-6-(methylcarbamoyl)-1H-indol-1-yl]propanoyl}amino)phenyl]butanoic acid,

(22) 4-{4-cyano-2-[(2-{3-methyl-6-[(2-methyl-2-propanyl)carbamoyl]-1H-indol-1-yl}propanoyl)amino]phenyl}butanoic acid,

(23) 4-{4-cyano-2-[(2-{6-([2-methoxyethyl)carbamoyl]-3-methyl-1H-indol-1-yl}propanoyl)amino]phenyl}butanoic acid,

(24) 4-[4-cyano-2-({2-[3-cyclopropyl-6-(methylcarbamoyl)-1H-indol-1-yl]propanoyl}amino)phenyl]butanoic acid,

(25) 4-{4-cyano-2-[(2-{3-cyclopropyl-6-[(2-methoxyethyl)carbamoyl]-1H-indol-1-yl}propanoyl)amino]phenyl}butanoic acid,

(26) 4-{2-({2-[3-methyl-6-(methylcarbamoyl)-1H-indol-1-yl]propanoyl}amino)-4-[(4-methyl-1H-pyrazol-1-yl)methyl]phenyl}butanoic acid,

(27) 4-[2-({2-[3-methyl-6-(methylcarbamoyl)-1H-indol-1-yl]propanoyl}amino)-4-phenoxyphenyl]butanoic acid, or

(28) 4-[2-({2-[3-methyl-6-(methylcarbamoyl)-1H-indol-1-yl]propanoyl}amino)-4-(5-methyl-1,3,4-oxadiazol-2-yl)phenyl]butanoic acid, or a pharmaceutically acceptable salt thereof.

[14] A pharmaceutical composition including the compound represented by the general formula (I), or a pharmaceutically acceptable salt thereof as an active ingredient.

[15] The pharmaceutical composition according to [14], being an $EP_4$ receptor antagonist.

[16] An agent for preventing and/or treating diseases caused by activation of $EP_4$ receptor, including the compound according to [1], or a pharmaceutically acceptable salt thereof, and further including a pharmaceutically acceptable carrier.

[17] The agent according to [16], wherein the disease caused by activation of $EP_4$ receptor is a bone disease, a cancer, a systemic granulomatous disease, an immune disease, an allergic disease, atopic dermatitis, asthma, alveolar pyorrhea, gingivitis, periodontitis, Alzheimer's, Kawasaki disease, burn, multiple organ failure, chronic headache, pain, vasculitis, venous incompetence, varicose veins, aneurysm, aortic aneurysm, anal fistula, diabetes insipidus, stress, endometriosis, uterine adenomyosis, patent ductus arteriosus in neonates, or cholelithiasis.

[18] The agent according to [17], wherein the cancer is breast cancer, ovarian cancer, large intestine cancer, lung cancer, prostate cancer, head and neck cancer, lymphoma, uveal malignant melanoma, thymoma, mesothelioma esophageal cancer, stomach cancer, duodenal cancer, hepatocellular cancer, bile duct cancer, gallbladder cancer, pancreatic cancer, renal cell cancer, renal pelvis and ureter cancer, bladder cancer, penile cancer, testicular cancer, uterine cancer, vaginal cancer, vulvar cancer, skin cancer, malignant bone tumor, soft tissue sarcoma, chondrosarcoma, leukemia, myelodysplastic syndrome, or multiple myeloma.

[19] A medicament including a combination of a compound represented by general formula (I), or a pharmaceutically acceptable salt thereof, and at least one or more agents selected from an alkylating agent, antimetabolites, anticancer antibiotics, plant-based preparations, hormones, platinum compounds, topoisomerase inhibitors, kinase inhibitors, an anti-CD 20 antibody, an anti-HER2 antibody, an anti-EGFR antibody, an anti-VEGF antibody, proteasome inhibitors, HDAC inhibitors, immune checkpoint inhibitors, and immunomodulators.

[20] A medicament including a combination of a compound represented by general formula (I), or a pharmaceutically acceptable salt thereof, and at least one or more agents selected from HMG-CoA reductase inhibitor, hypotensive agents, and tetracycline antibiotics.

[21] A medicament including a combination of a compound represented by general formula (I), a pharmaceutically acceptable salt thereof, and at least one or more agents selected from N-type calcium channel inhibitors, nitric oxide synthase (NOS) inhibitors, and cannabinoid-2 receptor stimulant.

[22] A method for preventing and/or treating a disease caused by activation of an $EP_4$ receptor, the method including: administering an effective amount of a compound represented by the general formula (I), or a pharmaceutically acceptable salt thereof, to a patient who needs prevention and/or treatment of the disease caused by activation of an $EP_4$ receptor.

[23] A compound represented by the general formula (I), or a pharmaceutically acceptable salt thereof, for preventing and/or treating the disease caused by activation of an $EP_4$ receptor.

[24] Use of the compound represented by the general formula (I), or a pharmaceutically acceptable salt thereof, for producing an agent for preventing and/or treating the disease caused by activation of an $EP_4$ receptor.

[25] An agent for preventing and/or treating diseases caused by activation of an $EP_4$ receptor, including the compound represented by the general formula (I), or a pharmaceutically acceptable salt thereof, which is administered in combination with at least one or more agents selected from an alkylating agent, antimetabolites, anticancer antibiotics, plant-based preparations, hormones, platinum compounds, topoisomerase inhibitors, kinase inhibitors, an anti-CD 20 antibody, an anti-HER2 antibody, an anti-EGFR antibody, an anti-VEGF antibody, proteasome inhibitors, HDAC inhibitors, immune checkpoint inhibitors, and immunomodulators.

[26] An agent for preventing and/or treating diseases caused by activation of an $EP_4$ receptor, including at least one or more agents selected from an alkylating agent, antimetabolites, anti cancer antibiotics, plant-based preparations, hormones, platinum compounds, topoisomerase inhibitors, kinase inhibitors, an anti-CD 20 antibody, an anti-HER2 antibody, an anti-EGFR antibody, an anti-VEGF antibody, proteasome inhibitors, HDAC inhibitors, immune checkpoint inhibitors, and immunomodulators, to be administered in combination with the compound represented by the general formula (I), or a pharmaceutically acceptable salt thereof.

Advantageous Effects of Invention

The compound of the present invention has a selective and strong antagonistic activity against an $EP_4$ receptor, and therefore is an agent for preventing and/or treating a disease caused by activation of the $EP_4$ receptor.

DESCRIPTION OF EMBODIMENTS

The present invention will be described in detail hereinafter.

In the present invention, examples of the "C1-4 alkyl" include methyl, ethyl, n-propyl, isopropyl, n-butyl, sec-butyl, tert-butyl, and isobutyl.

In the present invention, examples of the "C1-6 alkyl" include methyl, ethyl, n-propyl, isopropyl, n-butyl, sec-butyl, tert-butyl, isobutyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 1-methyl-1-ethylpropyl, 2-methyl-2-ethylpropyl, 1-ethylbutyl, 2-ethylbutyl, and the like.

In the present invention, examples of the "C2-4 alkenyl" include ethenyl, 1-propenyl, 2-propenyl, 1-butenyl, 2-butenyl, 3-butenyl, and the like.

In the present invention, examples of the "C2-6 alkenyl" include ethenyl, propenyl, butenyl, butadienyl, pentenyl, pentadienyl, hexenyl, hexadienyl, and isomers thereof, and the like.

In the present invention, examples of the "C2-4 alkynyl" include ethynyl, 1-propynyl, 2-propynyl, 1-butynyl, 2-butynyl, 3-butynyl, and the like.

In the present invention, examples of the "C2-6 alkynyl" include ethynyl, propynyl, propynyl, butynyl, butadiynyl, pentynyl, pentadiynyl, hexynyl, hexadiynyl, and isomers thereof, and the like.

In the present invention, examples of the "C1-3 alkylene" include methylene, ethylene, and propylene.

In the present invention, examples of the "C1-5 alkylene" include methylene, ethylene, propylene, butylene, and pentylene.

In the present invention, examples of the "C2-5 alkenylene" include ethenylene, 1-propenylene, 2-propenylene, 1-butenylene, 2-butenylene, 3-butenylene, 1-pentenylene, 2-pentenylene, 3-pentenylene, and 4-pentenylene.

In the present invention, examples of the "C2-5 alkynylene" include ethynylene, 1-propynylene, 2-propynylene, 1-buthynylene, 2-buthynylene, 3-buthynylene, 1-pentynylene, 2-pentynylene, 3-pentynylene, and 4-pentynylene.

In the present invention, examples of the "halogen atom" include fluorine, chlorine, bromine, and iodine.

In the present invention, examples of the "C1-4 alkoxy" include methoxy, ethoxy, propoxy, isopropoxy, butoxy, 1-methyl propoxy tert-butoxy, isobutoxy, and the like.

In the present invention, examples of the "C1-6 alkoxy" include methoxy, ethoxy, propoxy, butoxy, pentoxy, hexoxy, and isomers thereof, and the like.

In the present invention, examples of the "C1-4 alkylthio" include methylthio, ethylthio, propylthio, isopropylthio, butylthio, 1-methyl propylthio, tert-butylthio, isobutylthio, and the like.

In the present invention, examples of the "C1-6 alkylthio" include methylthio, ethylthio, propylthio, butylthio, pentylthio, hexylthio, and isomers thereof, and the like.

In the present invention, examples of the "C2-5 acyl" include ethanoyl, propanoyl, butanoyl, pentanoyl, and isomer thereof.

In the present invention, examples of the "5- to 6-membered aromatic ring" include benzene and the following "5- to 6-membered aromatic heterocycle."

In the present invention, examples of the "5- to 6-membered aromatic heterocycle" include pyrrole, imidazole, triazole, pyrazole, furan, thiophene, oxazole, isoxazole, thiazole, isothiazole, furazan, oxadiazole, thiadiazole, pyridine, pyrazine, pyrimidine, pyridazine, and the like.

In the present invention, examples of the "C3-8 saturated carbon ring" include cyclopropane, cyclobutane, cyclopentane, cyclohexane, cycloheptane, cyclooctane, and the like.

In the present invention, the "3- to 8-membered saturated heterocycle" means 3- to 8-membered saturated heterocycle including at least one nitrogen atom, and examples thereof include aziridine, azetidine, pyrrolidine, imidazolidine, triazolidine, pyrazolidine, tetrahydrooxazole, tetrahydroisoxazole, tetrahydrothiazole, tetrahydroisothiazole, tetrahydrofurazan, tetrahydrooxadiazole, tetrahydrothiadiazole, piperidine, piperazine, perhydropyrimidine, perhydropyridazine, tetrahydrooxazine, tetrahydrooxadiazine, tetrahydrothiazine, tetrahydrothiadiazine, morpholine, thiomorpholine, perhydroazepine, perhydrodiazepine, perhydrooxazepine, perhydrooxadiazepine, perhydrothiazepine, perhydrothiadiazepin, azabicyclo[3.2.1]octane, and the like.

In the present invention, examples of the "C3-6 carbon ring" include cyclopropane, cyclobutane, cyclopentane, cyclopentene, cyclepentadiene, cyclohexane, cyclohexene, cyclohexadlene, benzene, and the like.

In the present invention, examples of the "C3-10 carbon ring" means a C3-10 monocyclic or bicyclic carbon ring, and examples thereof include cyclopropane, cyclobutane, and the following "C5-10 carbon ring."

In the present invention, examples of the "3- to 10-membered heterocycle" means 3- to 10-membered monocyclic or bicyclic heterocycle including 1 to 5 heteroatoms selected from an oxygen atom, a nitrogen atom and a sulfur atom, and examples thereof include aziridine, oxirane, thiirane, oxetane, azetidine, thietane, and the following "5- to 10-membered heterocycle."

In the present invention, examples of the "C5-10 carbon ring" means, for example, a C5-10 monocyclic or bicyclic carbon ring, and examples thereof include cyclopentane, cyclohexane, cycloheptane, cyclooctane, cyclononane, cyclodecane, cyclopentene, cyclohexane, cycloheptene, cyclooctene, cyclononene, cyclodecene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene ring, and the like.

In the present invention, examples of the "5- to 10-membered heterocycle" means 5- to 10-membered monocyclic or bicyclic heterocycle including 1 to 5 heteroatoms selected from an oxygen atom, a nitrogen atom, and a sulfur atom, and examples thereof include pyrrolidine, pyrrole, imidazole, triazole, tetrazole, pyrazole, pyridine, piperidine, piperazine, pyrazine, pyrimidine, pyridazine, azepine, diazepine, furan, pyrane, oxepin, thiophene, thiopyrane, thiepin, oxazole, isoxazole, thiazole, isothiazole, furazan, oxadiazole, oxazine, oxadiazine, oxazepine, oxadiazepine, thiadiazole, thiazine, thiadiazine, thiazinane, thiazepine, thiadiazepine, indole, isoindole, indolizine, benzofuran, isobenzofuran, benzothiophene, isobenzothiophene, indazole, quinoline, isoquinoline, quinolizine, purine, phthalazine, pteridine, naphthyridine, quinoxaline, quinazoline, cinnoline, benzoxazole, benzothiazole, benzimidazole, benzodioxole, benzoxathiole, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyrane, dihydrothiepin, tetrahydrothiepin, perhydrothiepin, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, tetrahydrotriazolopyradine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydrisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomoipholine, dihydrobenzoxazole, perhydrobenzoxazole, dihydrobenzothiazole, perhydrobenzothiazole, dihydrobenzoimidazole, perhydrobenzoimidazole, dioxolane, dioxane, dioxaindan, benzodioxan, thiochroman, dihydrobenzodioxin, dihydrobenzoxathiin, chroman, pyrazolopyrimidine, imidazopyridazine, imidazopyridine, imidazopyrimidine, pyrrolopyridine, pyrrolopyrimidine, pyrrolopyridazine, imidazopyrazine, pyrazolopyridine, pyrazolopyrimidine, triazolopyridine, imidazo[1,2-B]pyridazine, 2,4,5,6-tetrahydro cyclopenta[C]pyrazole, 1,4,5,6-tetrahydrocyclepenta[C] pyrazole, dihydropyrido oxazine ring, and the like.

In the present invention, the "C6-10 aromatic carbon ring" is benzene and the following "bicyclic C9-10 aromatic carbon ring." The bicyclic C9-10 aromatic carbon ring is a bicyclic carbon ring having aromaticity, and a part of one ring may be saturated. Examples of the bicyclic C9-10 aromatic carbon ring include azulene, naphthalene, dihydronaphthalene, and tetrahydronaphthalene, and the like.

In the present invention, the "5- to 10-membered aromatic heterocycle" represents the above-mentioned "5- to 6-membered aromatic heterocycle" and the following "bicyclic 9- to 10-membered aromatic heterocycle," which include 1 to 5 heteroatoms selected from an oxygen atom, a nitrogen atom and a sulfur atom.

In the present invention, the "bicyclic 9- to 10-membered aromatic heterocycle" is a bicyclic heterocycle having aromaticity, and a part of one ring may be saturated. Examples of the "bicyclic 9- to 10-membered aromatic heterocycle" include benzothiophene, isobenzothiophene, dithianaphthalene, indazole, quinoline, isoquinoline, phthalazine, naphthyridine, quinoxaline, quinazoline, cinnoline, benzoxazole, benzothiazole, benzoimidazole, chromene, benzofurazan, benzothiadiazole, benzotriazole, indoline, isoindoline, dihydrobenzofuran, dihydro benzothiophene, dihydroisobenzothiophene, dihydroisobenzofuran, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazoic, dihydrobenzoimidazole, dioxaindan, benzodioxan, chroman, benzodithiolane, imidazo[1,2-B] pyridazine, 2,4,5,6-tetrahydrocyclopenta[C]pyrazole, 1,4,5, 6-tetrahydrocyclopenta[C]pyrazole, benzodithiane, and the like.

In the present invention, one of the two bond in -$L^1$- may be bonded to the ring B, or $L^2$, and, for example, —$NR^{33}C$(O)— represents (ring B)—$NR^{33}C(O)$-$L^2$, or (ring B)—$CONR^{33}$-$L^2$.

In the present invention, one of the two bond in -$L^3$- may be bound to the ring B, or $R^{11}$, and, for example, —C(O)$NR^{25}$— represents (ring B)—$NR^{25}$-$R^{11}$, or (ring B)—$NR^{25}C(O)$—$R^{11}$.

In the present invention, $R^1$ is preferably $COOR^5$.

In the present invention, $R^5$ is preferably a hydrogen atom or C1-4 alkyl, and more preferably a hydrogen atom.

In the present invention, A is preferably C1-5 alkylene, C2-5 alkenylene, or —O— (5- to 6-membered aromatic ring)-, more preferably C1-5 alkylene, and particularly preferably propylene.

In the present invention, $R^2$ is preferably a halogen atom, C1-4 alkyl, cyano, or -$L^3$-$R^{11}$, and more preferably a fluorine atom, cyano, or -$L^3$-$R^{11}$.

In the present invention, p is preferably 1 or 2, and more preferably 1.

In the present invention, $L^3$ is preferably a bond, —$CR^{12}R^{13}$—, —O—, —$CR^{14}(OR^{15})$—, —C(O)—, —$NR^{16}$—, —$CR^{17}R^{18}O$—, —$CR^{19}R^{20}NR^{21}$—, or —C(O)$NR^{25}$—, more preferably a bond, —$CH_2$—, —O—, —CH(OH)—, —C(O)—, —NH—, —$CH_2O$—, or —C(O)

NR$^{25}$—, further preferably —CH$_2$—, —O—, —CH$_2$O—, —C(O)NR$^{25}$—, and most preferably —CH$_2$—, or —CH$_2$O—. Another aspect of L$^3$, —C(O)NR$^{25}$— is preferable.

In the present invention, R$^{25}$ is preferably a hydrogen atom or methyl.

In the present invention, R$^{11}$ is preferably cyclopentane, cyclohexane, benzene, or 5-to 10-membered heterocycle, and more preferably 5- to 10-membered heterocycle. R$^{11}$ is further preferably benzene, pyridine, pyrazine, pyrazole, pyridazine, pyrimidine, oxadiazole, oxazole, imidazole, thiazole, isothiazole, 1,2,3-triazole, 1,2,4-triazole, tetrazole, tetrahydroisothiazole, morpholine, piperazine, pyrrolidine, thiazinane, thiazolidine, 2,4,5,6-tetrahydrocyclopenta[C]pyrazole, and 1,4,5,6-tetrahydrocyclopenta[C]pyrazole, and the most preferably pyrazole, pyridine, pyrimidine, imidazole, 1,2,3-triazole, 1,2,4-triazole, and tetrazole. Preferable R$^{11}$ is optionally substituted with R$^{26}$. Furthermore, another preferable aspect of R$^{11}$ is benzene substituted with R$^{26}$.

In the present invention, preferable L$^3$-R$^{11}$ is —CH$_2$— (5- to 10-membered heterocycle) or —CH$_2$O— (5- to 10-membered heterocycle). The 5-10-membered heterocycle is optionally substituted with R$^{26}$.

In the present invention, the ring B is preferably benzene or 5- to 6-membered aromatic heterocycle, further preferably benzene, pyridine, pyrazine, pyrimidine, or pyridazine, and most preferably benzene.

In the present invention, L$^1$ is preferably —NR$^{33}$CO—, and more preferably —NHCO—.

In the present invention, L$^2$ is preferably a bond, or —CR$^{35}$R$^{36}$—, more preferably —CR$^{35}$R$^{36}$—, further preferably —CH$_2$—, or —CH(CH$_3$)—, and most preferably —CH(CH$_3$)—.

In the present invention, u is preferably 1.

In the present invention, the ring C is preferably a bicyclic C9-10 aromatic carbon ring, or a bicyclic 9- to 10-membered aromatic heterocycle, more preferably naphthalene, indole, 1,2,3,4-tetrahydroquinoline, indoline, and chroman, and further preferably indole. The most preferable aspect of the ring C is indole bound to L$^2$ at a nitrogen atom.

In the present invention, R$^3$ is preferably a halogen atom, C1-4 alkyl, C1-4 alkoxy, a C3-8 saturated carbon ring, a 3- to 8-membered saturated heterocycle, more preferably C1-4 alkyl, and a C3-8 saturated carbon ring, further preferably methyl, ethyl, cyclobutyl, and cyclopropyl, and most preferably methyl and cyclopropyl.

In the present invention, preferably R$^3$ is preset on a C ring-constituting atom that is not bound to L$^2$.

In the present invention, n is preferably 0 or 1.

In the present invention, R$^4$ is preferably —CONR$^{41}$R$^{42}$, or —C(O)R$^{45}$, more preferably —CONR$^{41}$R$^{42}$, or —C(O)R$^{45-1}$, and further preferably —CON$^{41}$R$^{42}$.

In the present invention, R$^{41}$ is preferably a hydrogen atom, C1-6 alkyl, a C3-10 carbon ring, or a 3- to 10-membered heterocycle. The C1-6 alkyl, C3-10 carbon ring, and 3- to 10-membered heterocycle may be substituted with R$^{50}$, more preferable R$^{41}$ is methyl, ethyl, propyl, isopropyl, t-butyl, cyclopropyl, cyclobutyl, cyclopentyl, cyclohexyl, cyclopropylmethyl, benzyl, methoxyethyl, cyctopentyloxyethyl, and phenoxyethyl. Another preferable aspect of R$^{41}$ is C1-6 alkyl and a C3-8 saturated carbon ring, substituted with a substituent selected from the group consisting of (1) a halogen atom, (2) a hydroxyl group, (3) oxo, (4) thioxo, (5) cyano, (6) nitro, (7) —NR$^{51}$R$^{52}$, (8) C1-6 alkoxy, (9) C1-6 alkylthio, (10) a C6-10 aromatic carbon ring, (11) -G$^6$-(C3-10 carbon ring), (12) 3- to 10-membered heterocycle, and (13) -G$^6$-(3- to 10-membered heterocycle), more preferably C1-6 alkyl substituted with C1-4 alkoxy or —O—(C3-6 carbon ring), and further preferably methoxyethyl, cyclopentyloxyethyl, and phenoxyethyl.

In the present invention, R$^{42}$ is preferably a hydrogen atom, C1-6 alkyl, a C3-10 carbon ring, or a 3- to 10-membered heterocycle. The C1-6 alkyl, C3-10 carbon ring, and 3- to 10-membered heterocycle may be substituted with R$^{50}$, more preferable R$^{42}$ is methyl, ethyl, propyl, isopropyl, t-butyl, cyclopropyl, cyclobutyl, cyclopentyl, cyclohexyl, cyclopropylmethyl, benzyl, methoxyethyl, cyclopentyloxyethyl, and phenoxyethyl. Another preferable aspect of R$^{42}$ is a hydrogen atom, or C1-6 alkyl and a C3-8 saturated carbon ring, substituted with a substituent selected from the group consisting of (1) a halogen atom, (2) a hydroxyl group, (3) oxo, (4) thioxo, (5) cyano, (6) nitro, (7) —NR$^{51}$R$^{52}$, (8) C1-6 alkoxy, (9) C1-6 alkylthio, (10) a C6-10 aromatic carbon ring, (11) -G$^6$-(C3-10 carbon ring), (12) 3- to 10-membered heterocycle, and (13) -G$^6$-(3- to 10-membered heterocycle), more preferably C1-6 alkyl substituted with C1-4 alkoxy or —O— (C3-6 carbon ring), and further preferably methoxyethyl, cyclopentyloxyethyl, and phenoxyethyl.

In the present invention, another preferable aspect of R$^{41}$ and R$^{42}$ is 3- to 8-membered saturated heterocycle formed together with the bonded nitrogen atom.

In the present invention, preferable aspects of the 3- to 8-membered saturated heterocycle include azetidine, pyrrolidine, piperidine, and morpholine.

In the present invention, R$^{45}$ is preferably C1-6 alkyl, C2-6 alkenyl, or C2-6 alkynyl, and more preferably C1-6 alkyl.

In the present invention, m is preferably 0 or 1, and more preferably 1.

In the present invention, R$^{4-1}$ is preferably —CONR$^{41}$R$^{42}$.

In the present invention, X is preferably CR$^{2-2}$, and more preferably CH.

In the present invention, R$^{2-1}$ is preferably fluorine, cyano, or -L$^3$-R$^{11}$.

In the present invention, R$^{2-2}$ is preferably a hydrogen atom, C1-4 alkyl, or a halogen atom, and more preferably a hydrogen atom.

In the present invention, the ring C$^1$ is preferably naphthalene, indole, 1,2,3,4-tetrahydroquinoline, indoline, and chroman, further preferably indole, and the most preferable aspect of the ring C$^1$ is indole bound to —C(R$^{35}$)(R$^{36}$)— at a nitrogen atom.

In the present invention, the general formula (I) is preferably a combination of the respective preferable definitions of the above R$^1$, A, R$^2$, R$^3$, R$^4$, R$^5$, R$^{11}$, R$^{35}$, R$^{36}$, R$^{41}$, R$^{42}$, ring B, ring C, L$^1$, L$^2$, L$^3$, p, n, m, and u.

In the present invention, the general formula (I-0) is preferably a combination of the respective preferable definitions of the above R$^1$, A, X, R$^{2-0}$, R$^{2-2}$, R$^3$, R$^{35}$, R$^{36}$, R$^{4-1}$, ring C$^1$, L$^1$, and n.

In the present invention, the general formula (I-1) is preferably a combination of the respective preferable definitions of the above R$^1$, A, X, R$^{2-1}$, R$^{2-2}$, R$^3$, R$^{11}$, R$^{35}$, R$^{36}$, R$^{41}$, R$^{42}$, ring C$^1$, L$^1$, L$^3$, and n.

In the present invention, the preferable aspect is compounds described in Examples.

In the present invention, the compound represented by the general formula (I) preferably includes a compound represented by the general formula (I-0):

[Chem. 8]

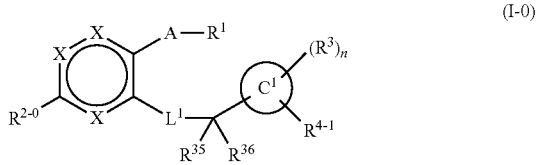

(I-0)

(wherein, in the formula, all the symbols have the same meanings as those described above).

In the present invention, another preferable aspect of the compound represented by the general formula (I) includes a compound represented by the general formula (I-1):

[Chem. 9]

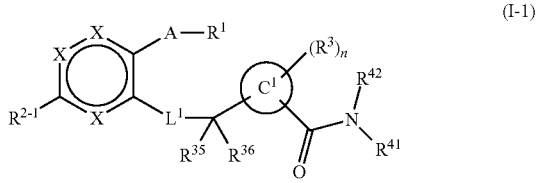

(I-1)

(wherein in the formula, all the symbols have the same meanings as those described above), or a pharmaceutically acceptable salt thereof.

In the present invention, a further preferable aspect of the compound represented by the general formula (I) includes a compound represented by general formula (I-a):

[Chem. 10]

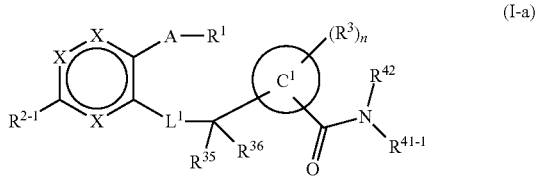

(I-a)

(wherein in the formula, $R^{41-1}$ is C1-6 alkyl, C1-6 alkenyl, C1-6 alkynyl, a C3-10 carbon ring, or a 3- to 10-membered heterocycle in which $R^{41-1}$ is substituted with one or more $R^{50}$'s (excluding $CHF_2$, $CF_3$, and benzyl), the other symbols have the same meanings as those described above), or a pharmaceutically acceptable salt thereof. A still further preferable aspect is a compound represented by the general formula (I-b):

[Chem. 11]

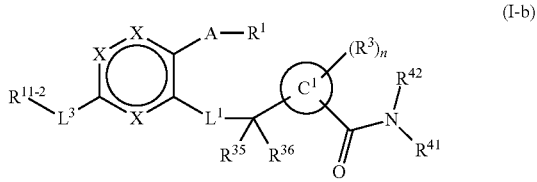

(I-b)

(wherein in the formula, $R^{11-2}$ represents 3- to 10-membered heterocycle which may be substituted with one to five $R^{26}$'s, and the other symbols have the same meanings as those described above), or a pharmaceutically acceptable salt thereof.

In the present invention, the preferable aspect of the general formula (I) is the general formula (I-2):

[Chem. 12]

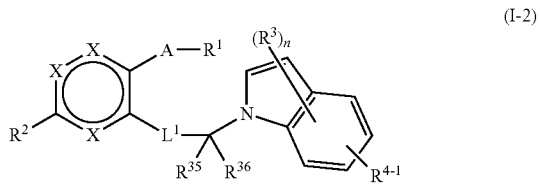

(I-2)

(wherein in the formula, $R^{4-1}$ represents $-CONR^{41}R^{42}$ or $-C(O)R^{45-1}$, $R^{45-1}$ represents C1-6 alkyl, C2-6 alkenyl, and C2-6 alkynyl, and the other symbols have the same meanings as those described above).

In the present invention, the most preferable other aspect of the general formula (I) is a general formula (I-3):

[Chem. 13]

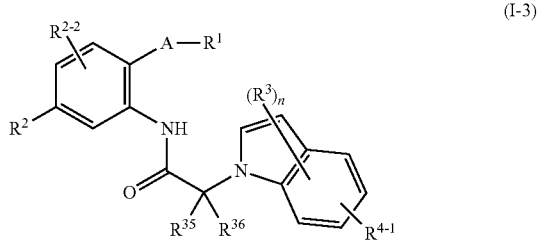

(I-3)

(wherein all the symbols have the same meanings as those described above), and in the present invention, the most preferable other aspect of the general formula (I) is a general formula (I-c):

[Chem. 14]

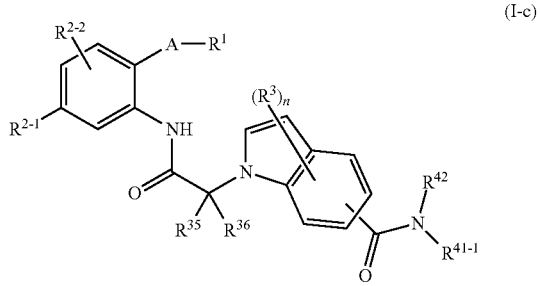

(I-c)

(wherein in the formula, all the symbols have the same meanings as those described above), and the most preferable other aspect of the general formula (I) is a compound represented by the general formula (I-d):

[Chem. 15]

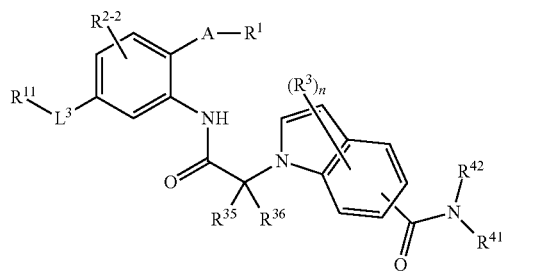

(I-d)

(wherein in the formula, all the symbols have the same meanings as those described above (excluding a compound in which $R^{11}$ is a C3-10 carbon ring)), or a pharmaceutically acceptable salt thereof.

In the present invention, another preferable aspect of the general formula (I) is a compound represented by the general formula (I-e):

[Chem. 16]

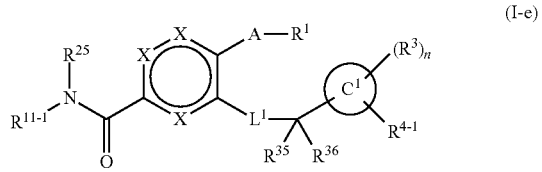

(I-e)

(wherein in the formula, $R^{11-1}$ is $R^{11}$ substituted with one or more $R^{26}$'s, the other symbols have the same meanings as those described in the above [1] or [5]), or a pharmaceutically acceptable salt thereof. The most preferable other aspect of the general formula (I) is a compound represented by the general formula (I-f):

[Chem. 17]

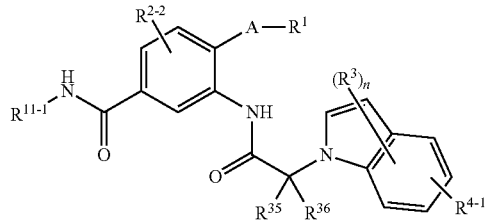

(I-f)

(wherein in the formula, all the symbols have the same meanings as those described above), or a pharmaceutically acceptable salt thereof.

In the present invention, in the above general formula (I-a), (I-b), (I-c), (I-d), (I-e), (I-f), (I-0), (I-1), (I-2) or (I-3), each independently and preferably, A is C1-5 alkylene, and more preferably propylene.

In the present invention, in the above general formula (I-a), (I-b), (I-0), (I-1), or (I-2), each independently and preferably, $L^1$ is —NHCO—.

In the present invention, $R^{35}$ and $R^{36}$ in the above general formula (I-a), (I-b), (I-c), (I-d), (I-e), (I-f), (I-0), (I-1), (I-2), or (I-3), are preferably that any one of $R^{35}$ and $R^{36}$ is a hydrogen atom. When one of $R^{35}$ and $R^{36}$ is a hydrogen atom, and the other is not a hydrogen atom, the steric configuration of an asymmetric carbon may be R or S, or a mixture of any rate of R and S.

In the present invention, the most preferable other aspect of the general formula (I) is preferably the compounds of the present invention described in Examples mentioned later, or a pharmaceutically acceptable salt thereof.

In the present invention, unless specifically directed, all of the isomers are included. For example, an alkyl group, an alkoxy group, in alkylene group, and the like, include linear and branched chain groups. In addition, all of geometrical isomers of double bonds, rings, and "fused rings (E-, Z-, cis-, trans-isomers), optical isomers by the presence of asymmetric carbon (R-, S-isomer, α-, β-isomer, enantiomers, diastereomers), optically active substances having optical rotation property (D, L, d, l-isomers), polar isomers according to chromatographic separation (more polar isomer, less polar isomer), equilibrium compound, retainers, mixtures thereof at any rate, and racemic mixtures are included in the present invention. Furthermore, the present invention also encompasses all isomers by tautomers.

In the present invention, unless otherwise noted, as apparent to a person skilled in the art, a symbol:

[Chem. 18]

represents binding toward the back side of the plane of the paper (that is, the α-configuration),

[Chem. 19]

represents binding toward the front side of the plane of the paper (that is, the β-configuration), and

[Chem. 20]

represents an arbitrary mixture of the α-configuration and the β-configuration.

[Salt]

The compound represented by the general formula (I) is converted into a salt by the well-known method.

A salt is a pharmaceutically acceptable salt.

A salt is preferably a water-soluble salt.

Examples of the pharmaceutically acceptable salt include acid addition salt, alkali metal salt, alkaline earth metal salt, ammonium salt, amine salt, or the like.

Examples of the acid addition salt include inorganic acid salt such as hydrochloride, hydrobromate, hydroiodide, sulfate, phosphate, nitrate, or organic acid salt such as acetate, lactate, tartrate, benzoate, citrate, methanesulfonate, ethanesulfonate, trifluoroacetate, benzenesulfonate, toluenesulfonate, isothionate, glucuronate, or gluconate.

Examples of the alkali metal salt include potassium salt, sodium salt, and the like.

Examples of the alkaline earth metal salt include calcium salt, magnesium salt, and the like.

Examples of the ammonium salt include tetramethylammonium salt or the like.

Examples of the amine salt include triethylamine salt, methylamine salt, dimethylamine salt, cyclopentylamine salt, benzylamine salt, phenethylamine salt, piperidine salt, monoethanolamine salt, diethanolamine salt, tris(hydroxymethyl)aminomethane salt, lysine salt, arginine salt, N-methyl-D-glucamine salt, and the like.

Furthermore, the compound of the present invention can be made into N-oxide by arbitrary methods. The N-oxide is the compound represented by the general formula (I) in which a nitrogen atom is oxidized.

The compound represented by the general formula (I) and a salt thereof can be converted into a solvate.

The solvate is preferably nontoxic and water-soluble. Suitable examples of the solvate include solvates like water, or alcohol solvent (for example, ethanol).

The compound represented by the general formula (I) can form a cocrystal with an appropriate cocrystal former. As the cocrystal, pharmaceutically acceptable cocrystal that is formed with a pharmaceutically acceptable cocrystal former is preferable. The cocrystal is typically defined as a crystal that is formed of wo or more different molecules by intermolecular interaction that is different from ionic bond. Furthermore, the cocrystal may be a composite of a neutral molecule and a salt. The cocrystal can be prepared by recrystallization from a solvent by a well-known method, for example, melting crystallization, recrystallization from solvent, or physically pulverizing the components together. Appropriate cocrystal formers include ones described in WO2006/007448.

[Prodrug]

The prodrug of the compound represented by the general formula (I) denotes a compound which is converted into the compound represented by the general formula (I) by a reaction with an enzyme, stomach acid, and the like, in a living body. Examples of the the prodrug of the compound represented by the general formula (I) include, when the compound represented by the general formula (I) includes an amino group, compounds in which the amino group is acylated, alkylated, and phosphorylated (for example, the compounds in which an amino group of the compound represented by the general formula (I) has been eicosanoylated, alanylated, pentylaminocarbonylated, (5-methyl-2-oxo-1,3-dioxolene-4-yl)methoxycarbonylated, tetrahydrofuranylated, pyrrolidinylmethylated, pivaloyloxymethylated, acetoxymethylated, tert-butylated, and the like); when the compound represented by the general formula (I) has a hydroxyl group, compounds in which the hydroxyl group is acylated, alkylated, phosphorylated, or borated (for example, the compounds represented by the general formula (I) in which the hydroxyl group is acetylated, palmitoylated, propanoylated, pivaloylated, succinylated, fumarylated, alanylated, or dimethyl aminomethyl carbonylated); and when the compound represented by the general formula (I) has a carboxyl group, compounds in which the carboxyl group is esterified or amidated (for example, compounds represented by the general formula (I) in which the carboxyl group is made into ethyl ester, phenyl ester, carboxymethyl ester, dimethylaminomethyl ester, pivaloyloxymethyl ester, 1-{(ethoxycarbonyl)oxy}ethyl ester, phthalidyl ester, (5-methyl-2-oxo-1,3-dioxolen-4-yl)methyl ester, 1-{[(cyclohexyloxy)carbonyl]oxy}ethyl ester, methylamide, and the like). These compounds, as it is, can be produced by well-known methods. Furthermore, the prodrug of the compound represented by the general formula (I) may be hydrate or non-hydrate. Furthermore, the prodrug of the compound represented by the general formula (I) may be a compound which is changed into the compound represented by the general formula (I) under the physiological condition, as described in "Development of Medicaments", vol. 7 "Molecular Design", p. 163-198, published by Hirokawa Shoten in 1990.

In addition, the compound represented by the general formula (I) may be labeled with an isotope thereof (for example, $^2H$, $^3H$, $^{11}C$, $^{13}C$, $^{14}C$, $^{15}N$, $^{16}N$, $^{17}O$, $^{18}O$, $^{18}F$, $^{35}S$, $^{36}Cl$, $^{77}Br$, and $^{125}I$), and the like.

[Process for Producing Compound of the Present Invention]

The compound of the present invention represented by the general formula (I) can be produced by the well-known methods, for example, the methods described below, the methods conforming to these methods, or the methods shown in Examples. Note here that in the following each production methods, each raw material compound may be used as a salt. Such a salt preferably include salts described as pharmaceutically acceptable salts of the compounds of the present invention represented by the general formula (I).

In the compound of the present invention represented by the general formula (I), the compound of the present invention represented by the general formula (IVa) in which $L^1$ is —$NR^{33}CO$—, or the compound of the present invention represented by the general formula (IVb) in which $L^1$ is —$CONR^{33}$— can be produced by the method shown in the following reaction scheme (Ia) or (Ib), respectively.

Reaction scheme (Ia)

[Chem. 21]

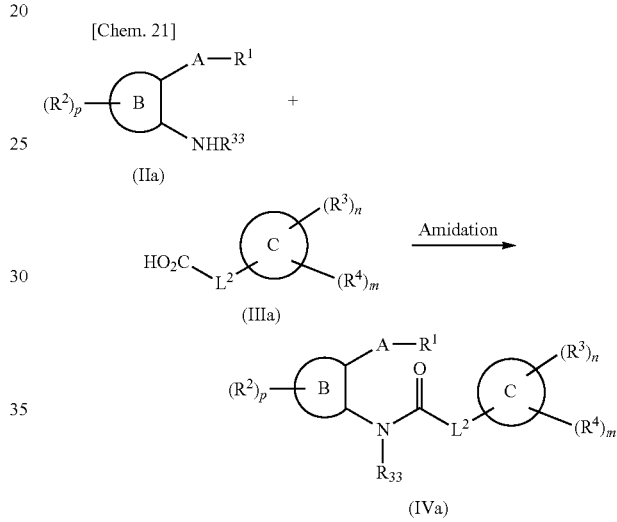

(wherein in the formula, all the symbols have the same meanings as defined in the above [1]), or Reaction scheme (Ib)

[Chem.22]

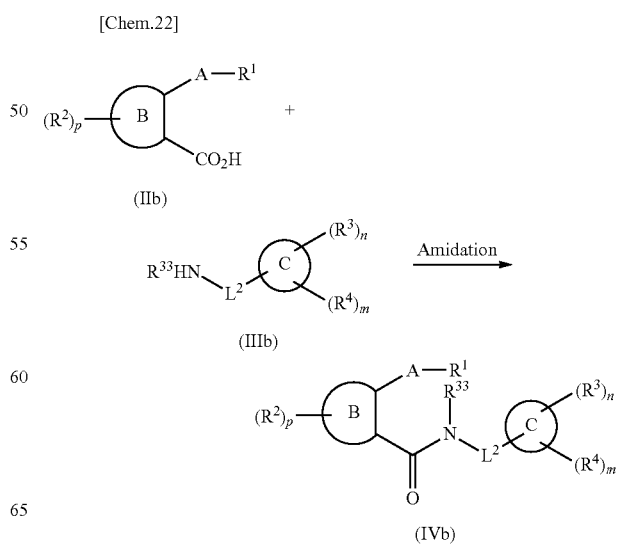

(wherein in the formula, all the symbols have the same meanings as defined in the above [1]).

In other words, the compound of the present invention represented by the general formula (IVa) can be produced by subjecting the compound represented by the general formula (IIa) and the compound represented by the general formula (IIIa) to an amidation reaction. Furthermore, the compound of the present invention represented by the general formula (IVb) can be produced by subjecting the compound represented by the general formula (IIb) and the compound represented by the general formula (IIIb) to an amidation reaction.

The amidation reaction is well known, and examples thereof include:
(1) a method using an acid halide,
(2) a method using a mixed acid anhydride, and
(3) a method using a condensing agent.

These methods are specifically described below:

(1) The method using an acid halide is carried out, for example, by reacting a carboxylic acid with an acid halogenating agent (oxalyl chloride, thionyl chloride, and the like) in an organic solvent (chloroform, dichloromethane, diethyl ether, tetrahydrofuran, and the like) or in the absence of any solvent at about −20° C. to reflux temperature, and then reacting the obtained acid halide in the presence of a base (pyridine, triethylamine, dimethylaniline, dimethylaminopyridine, diisopropylethylamine, and the like) with an amine in an organic solvent (chloroform, dichloromethane, diethyl ether, tetrahydrofuran, and the like) at about 0 to 40° C. Furthermore, the method can be also carried out by reacting the obtained acid halide with an amine at about 0 to 40° C. by using an alkaline aqueous solution (sodium bicarbonate water or a sodium hydroxide solution, and the like) in an organic solvent (dioxane, tetrahydrofuran, and the like).

(2) The method using a mixed acid anhydride is carried out, for example, by reacting carboxylic acid with an acid halide (pivaloyl chloride, tosyl chloride, mesyl chloride, and the like) or an acid derivative (ethyl chloroformate, isobutyl chloroformate, and the like) in an organic solvent (chloroform, dichloromethane, diethyl ether, tetrahydrofuran, and the like) or in the absence of any solvent in the presence of a base (pyridine, triethylamine, dimethylaniline, dimethylaminopyridine, diisopropylethylamine, and the like) at about 0 to 40° C., and then reacting the obtained mixed acid anhydride with amine in an organic solvent (chloroform, dichloromethane, diethyl ether, tetrahydrofuran, and the like) at about 0 to 40° C.

(3) The method using a condensing agent is carried out, for example, by reacting a carboxylic acid with an amine in an organic solvent (chloroform, dichloromethane, dimethyl formamide, dimethylacetamide, diethyl ether, tetrahydrofuran, and the like) or in the absence of any solvent, in the presence or absence of a base (pyridine, triethylamine, dimethylaniline, dimethylaminopyridine, and the like), using a condensing agent (1,3-dicyclohexylcarbodiimide (DCC), 1-ethyl-3-[3-(dimethylamino)propyl]carbodiimide (EDC), 1,1'-carbonyl diimidazole (CDI), 2-chloro-1-methylpyridinium iodine, 1-propylphosphonic acid cyclic anhydride (1-propanephosphonic acid cyclic anhydride, T3P), and the like), and in the presence or absence of 1-hydroxybenztriazole (HOBt) at about 0° C. to reflux temperature.

These reactions (1), (2), and (3) are desirably carried out under the atmosphere of an inert gas (argon, nitrogen, etc.) in anhydrous conditions.

In the compound of the present invention represented by the general formula (I), the compound of the present invention represented by the general formula (IVc) in which $L^1$ is $-NR^{34}SO_2-$, or the compound of the present invention represented by the general formula (IVd) in which $L^1$ is $-SO_2NR^{34}-$ can be produced by the method shown in the following reaction scheme (Ic) or (Id), respectively.

Reaction scheme (Ic)

[Chem. 23]

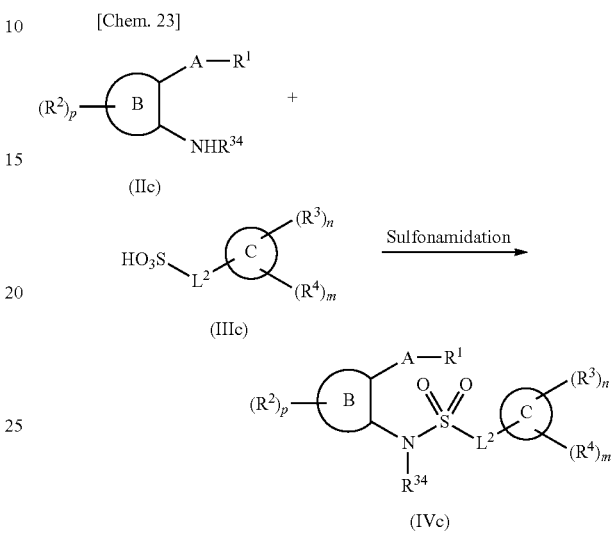

(wherein in the formula, all the symbols have the same meanings as defined in the above [1]) or Reaction scheme (Id)

[Chem. 24]

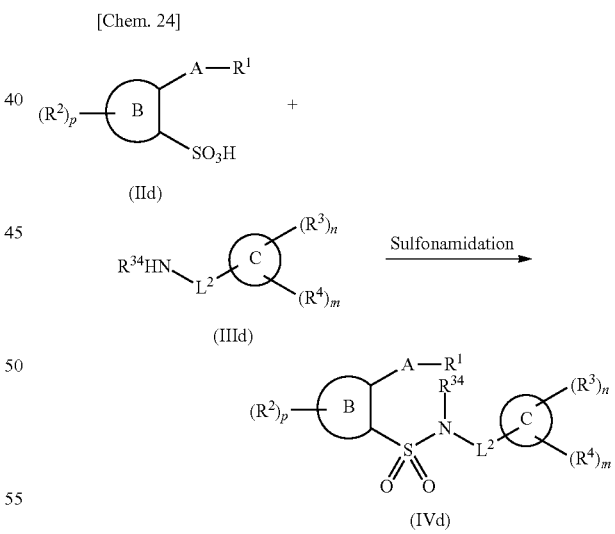

(wherein in the formula, all the symbols have the same meanings as defined in the above [1]).

In other words, the compound of the present invention represented by the general formula (IVc) can be produced by subjecting the compound represented by the general formula (IIc) and the compound represented by the general formula (IIIc) to a sulfoamidation reaction. Furthermore, the compound of the present invention represented by the general formula (IVd) can be produced by subjecting the compound represented by the general formula (IId) and the compound represented by the general formula (IId) to a sulfoamidation reaction.

The sulfoamidation reaction is well known, and carried out, for example, by reacting sulfonic acid with acid halide (oxalyl chloride, thionyl chloride, phosphorus pentachloride, phosphorus trichloride, and the like) in an organic solvent (chloroform, dichloromethane, dichloroethane, diethyl ether, tetrahydrofuran, methyl t-butyl ether, and the like) or in the absence of any solvent at −20° C. to reflux temperature to obtain sulfonyl halide, and reacting the obtained sulfonyl halide with amine in the presence of base (diisopropylethylamine, pyridine, triethylamine, dimethylaniline, dimethylaminopyridine, and the like) in an organic solvent (chloroform, dichloromethane, dichloroethane, diethyl ether, tetrahydrofuran, and the like) at a temperature of about 0 to 40° C.

In the compound of the present invention represented by the general formula (I), the compound of the present invention represented by the general formula (IVe) in which $L^1$ is —$NR^{32}CH_2$—, or the compound of the present invention represented by the general formula (IVf) in which $L^1$ is —$CH_2NR^{32}$— can be produced by the method shown in the following reaction scheme (Ie) or (If), respectively.

Reaction scheme (Ie)

[Chem. 25]

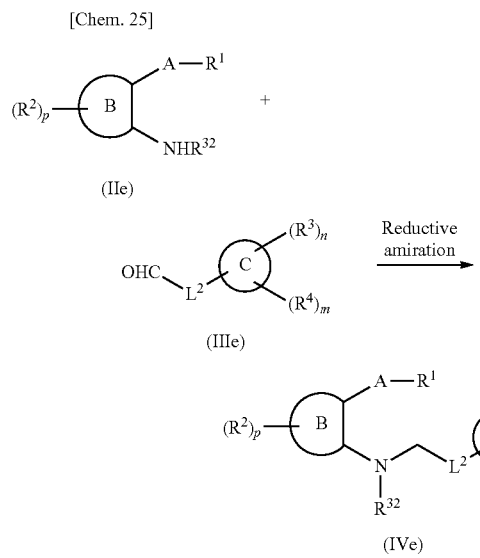

(wherein in the formula, all the symbols have the same meanings as defined in the above [1]), or Reaction scheme (If)

[Chem. 26]

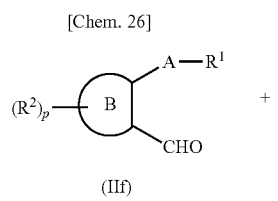

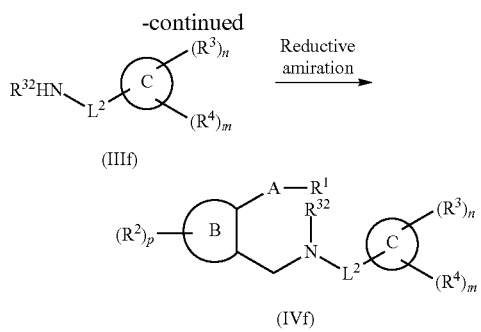

(wherein in the formula, all the symbols have the same meanings as defined in the above [1]).

In other words, the compound of the present invention represented by the general formula (IVe) can be produced by subjecting the compound represented by the general formula (IIe) and the compound represented by the general formula (IIIe) to a reductive amination reaction. Furthermore, the compound of the present invention represented by the general formula (IVf) can be produced by subjecting the compound represented by the general formula (IIf) and the compound represented by the general formula (IIIf) to a reductive amination reaction.

The reductive amination reaction is well known. For example, a reaction is carried out in an organic solvent (dichloroethane, dichloromethane, dimethylformamide, acetic acid, and a mixture thereof), and in the presence of a reducing agent (sodium triacetoxy borohydride, cyano sodium borohydride, sodium borohydride, and the like) at about 0 to 40° C.

In the compound of the present invention represented by the general formula (I), the compound of the present invention represented by the general formula (IVg) in which $L^1$ is —$OCH_2$—, or the compound of the present invention represented by the general formula (IVh) in which $L^1$ is —$CH_2O$— can be produced by the method shown in the following reaction scheme (Ig) or (Ih), respectively.

Reaction scheme (Ig)

[Chem. 27]

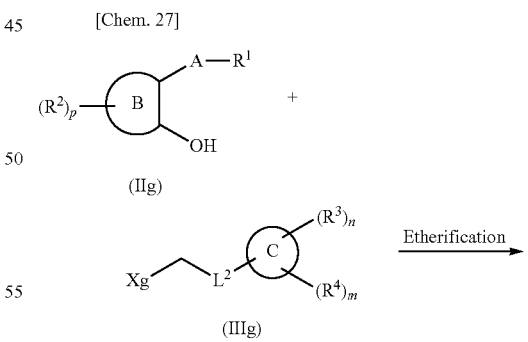

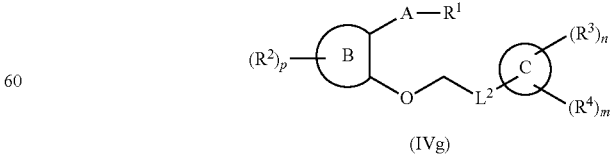

(wherein in the formula, Xg is a halogen atom, tosylate, or mesylate, and the other symbols have the same meanings as defined in the above [1])

Reaction scheme (Ih)

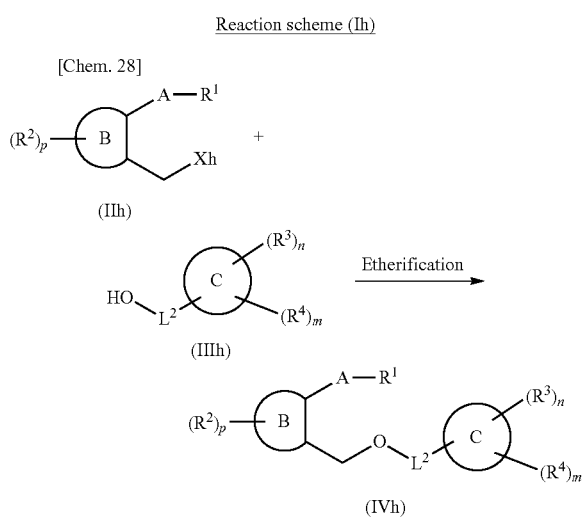

(wherein in the formula, Xh is a halogen atom, tosylate, or mesylate, and the other symbols have the same meanings as defined in the above [1]).

In other words, the compound of the present invention represented by the general formula (IVg) can be produced by subjecting the compound represented by the general formula (IIg) and the compound represented by the general formula (IIIg) to an etherification reaction. Furthermore, the compound of the present invention represented by the general formula (IVh) can be produced by subjecting the compound represented by the general formula (IIh) and the compound represented by the general formula (IIIh) to an etherification reaction.

The etherification reaction is well known. For example, a reaction is carried out in an organic solvent (dimethylformamide, dimethyl sulfoxide, chloroform, dichloromethane, diethyl ether, tetrahydrofuran, methyl t-butyl ether, and the like), in the presence of base (sodium hydroxide, potassium hydroxide, lithium hydroxide, barium oxide, calcium hydroxide, sodium hydride, potassium t-butoxide, sodium carbonate, potassium carbonate, and the like), or an aqueous solutions thereof or a mixture thereof at about 0 to 100° C.

In the compound of the present invention represented by the general formula (I), a compound of the present invention in which $L^1$ is —$SCH_2$— is produced by carrying out a reaction using a compound represented by the general formula (IIs):

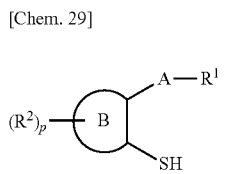

instead of the compound represented by the general formula (IIg) in reaction scheme (Ig).

In the compound of the present invention represented by the general formula (I), a compound of the present invention in which $L^1$ is —$CH_2S$— is produced by carrying out a reaction using a compound represented by the general formula (IIIs):

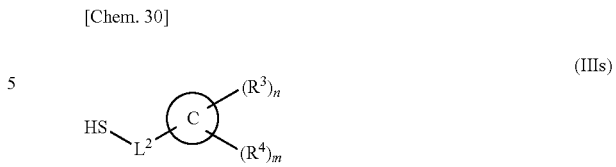

instead of the compound represented by the general formula (IIIh) in reaction scheme (Ih).

In the compound of the present invention represented by the general formula (I), the compound of the present invention in which $L^1$ is —$S(O)CH_2$— or $L^1$ is —$SO_2CH_2$— can be produced by appropriately subjecting a sulfur atom of the compound of the present invention in which L is —$SCH_2$— to oxidation reaction (sulfoxidation reaction, or sulfonation reaction).

The sulfoxidation reaction (—$SCH_2$—→—$S(O)CH_2$—, or —$CH_2S$—→—$CH_2S(O)$—) is well-known. For example, a reaction is carried out in an organic solvent (dichloromethane, chloroform, benzene, hexane, methanol, t-butyl alcohol, acetone, acetonitrile, tetrahydrofuran, acetic acid, N,N-dimethyl formamide, and the like), in water or a mixed solvent of these, in the presence of 1 to 1.2 equivalent oxidizing agents (hydrogen peroxide, sodium periodate, acyl nitrite, sodium perborate, sodium hypochlorite, peracid (3-chloroperbenzoic acid, peracetic acid, and the like), oxone (trade name, hereinafter abbreviated to oxon; potassium peroxymonosulfate), potassium permanganate, chromic acid, dimethyldioxolane, and the like) at a temperature of about −40 to 0° C.

The sulfonation reaction (—$SCH_2$—→—$SO_2CH_2$, or —$CH_2S$—→—$CH_2SO_2$—) is well-known. For example, a reaction is carried out in an appropriate organic solvent (dichloromethane, chloroform, benzene, hexane, methanol, t-butyl alcohol, acetone, acetonitrile, tetrahydrofuran, acetic acid, N,N-dimethylformamide, and the like), in water or a mixed solvent of these, and in the presence of excessive amount of oxidizing agents (hydrogen peroxide, sodium periodate, acyl nitrite, sodium perborate, sodium hypochlorite, peracid (3-chloroperbenzoic acid, peracetic acid, and the like), oxone (trade name; potassium peroxymonosulfate), potassium permanganate, chromic acid, dimethyldioxolane, and the like) at a temperature of about 20 to 60° C.

In the compound of the present invention represented by the general formula (I), the compound of the present invention represented by the general formula (IVi) in which $L^1$ is —CH=CH— can be produced by the method shown in the following reaction scheme (Ii).

Reaction scheme (Ii)

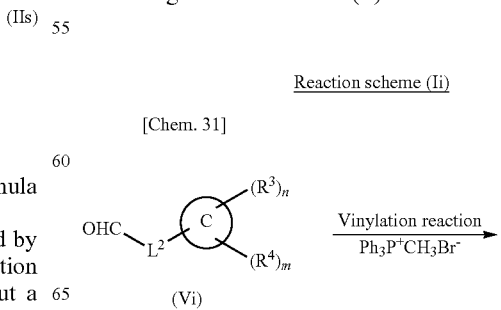

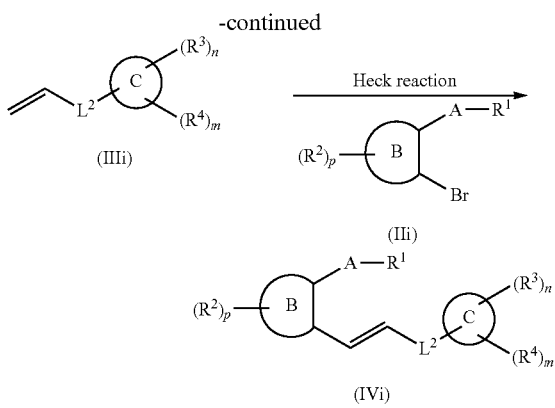

(wherein in the formula, all the symbols have the same meanings as defined in the above [1])

The compound represented by the general formula (IIIi) can be produced by subjecting the compound represented by the general formula (Vi) to vinylation reaction.

The vinylation reaction is well known. For example, a reaction is carried out by reacting a compound represented by the general formula (Vi) and methyl tirphenyl phosphonium bromide in an organic solvent (for example, acetonitrile, methylene chloride, tetrahydrofuran, toluene, benzene, a solvent in which these organic solvents are appropriately mixed, or the like), in the presence of base (for example, potassium carbonate, sodium hydride, potassium hydride, n-butyl lithium, tert-butoxy potassium, 1,8-diazabicyclo[5.4.0]undeca-7-entriethylamine (DBU), and the like) at a temperature of about 0 to 120° C.

The compound represented by the general formula (IVi) can be produced by subjecting a compound represented by the general formula (IIIi) and a compound represented by the general formula (IIi) to a Heck reaction.

The Heck reaction is well-known. For example, a reaction is carried out in an organic solvent (for example, toluene, diethyl ether, benzene, dichlorobenzene, dimethylformamide, a solvent in which these organic solvents are appropriately mixed, or the like) in the presence of base (for example, tripotassium phosphate, sodium hydrogencarbonate, trimethylamine, and the like), and a catalyst (for example, palladium catalyst (for example, palladium chloride, palladium acetate, tetrakis(triphenylphosphine)palladium (0), and the like), a nickel catalyst (for example, tetrakis(triphenylphosphine)nickel, bis(triphenylphosphine)nickel (II), and the like), a cobalt catalyst (for example, cobalt chloride and the like), a copper catalyst (for example, copper chloride and the like) a zinc catalyst (for example, zinc and the like), or catalyst in which these catalysts are appropriately mixed), and farther in the presence or absence of a phosphorus reagent (for example, 1,3-bis(diphenylphosphino)propane (dppp), $Ph_2P-(CH_2)_6-PPh_2$, and the like) at a temperature of about 0 to 120° C.

In the compounds of the present invention represented by the general formula (I), the compound of the present invention represented by the general formula (IVi) in which $L^2$ is $-CH_2CH_2-$ can be produced by appropriately substituting the "$-CH=CH-$" in the compound of the present invention represented by the general formula (IVi) to reduction reaction.

The reduction reaction is well-known. For example, a reaction is carried out in an organic solvent (for example, tetrahydrofuran, dioxane, dimethoxyethane, diethyl ether, methanol, ethanol, benzene, toluene, acetone, methyl ethyl ketone, acetonitrile, dimethylformamide, water, ethyl acetate, acetic acid, a solvent in which these organic solvents are appropriately mixed, or the like), in the presence of a hydrogenation catalyst (palladium carbon, palladium black, palladium, palladium hydroxide, platinum dioxide, platinum-carbon, nickel, Raney nickel, ruthenium chloride, and the like), in the presence or in the absence of acid (hydrochloric acid, sulfuric acid, hypochlorous acid, boric acid, tetrafluoroboric acid, acetic acid, p-toluenesulfonic acid, oxalic acid, trifluoroacetic acid, formic acid, and the like), in a hydrogen atmosphere under normal pressure or with pressure added, in the presence of formic acid ammonium or in the presence of hydrazine at a temperature of about 0 to 200° C.

The compound represented by the general formula (IIa) in the reaction scheme (Ia), when one $R^2$ is $-L^3-R^{11}$, is $-CH_2O-$, $R^{33}$ is a hydrogen atom, can be produced by the method represented by the reaction scheme (Ij).

Reaction scheme (Ij)

[Chem. 32]

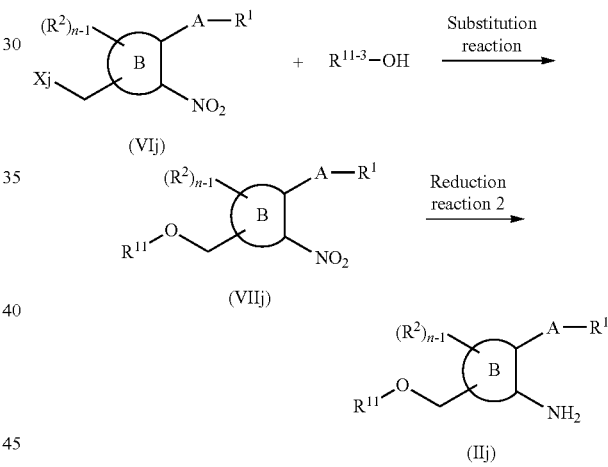

(wherein in the formula, $R^{11-3}-$ represents a C3-10 carbon ring-, or a 3- to 10-membered heterocycle-, the C3-10 carbon ring and 3- to 10-membered heterocycle may be substituted with one to five $R^{26}$'s, and a plurality of $R^{26}$'s may be the same as or different from each other, Xj is a halogen atom, tosylate, or mesylate, and the other symbols have the same meanings as defined in the above [1]).

In the reaction scheme (Ij), a compound represented by the general formula (VIIj) can be produced by substituting the compound represented by the general formula (VIj) with $R^{11-3}-OH$. This substituting reaction is well-known. For example, a reaction is carried out in an organic solvent (dimethylformamide, dimethyl sulfoxide, chloroform, dichloromethane, diethyl ether, tetrahydrofuran, methyl t-butyl ether, and the like), in the presence of hydroxide of alkali metal (sodium hydroxide, potassium hydroxide, lithium hydroxide, and the like), hydroxide of alkali earth metal (barium hydroxide, calcium hydroxide, and the like) or carbonate (sodium carbonate, potassium carbonate, cesium carbonate and the like), or an aqueous solution thereof or mixture of these at a temperature of about 0 to 100° C.

In the reaction scheme (Ij), a compound represented by the general formula (IIj) can be produced by subjecting a nitro group of the compound represented by the general formula (VIIj) to a reduction reaction. The reduction reaction 2 of a nitro group is well-known, and can be carried out by, for example, the following method.

1) For example, in a solvent [ethers (tetrahydrofuran, dioxane, dimethoxyethane, diethyl ether, and the like), alcohols (methanol, ethanol, and the like), benzenes (benzene, toluene, and the like), ketones (acetone, methyl ethyl ketone, and the like), nitriles (acetonitrile, and the like), amides (dimethylformamide, and the like), water, ethyl acetate, acetic acid, or a mixture of two or more thereof, etc.], in the presence of a hydrogenation catalyst (palladium carbon, palladium black, palladium, palladium hydroxide, platinum dioxide, platinum-carbon, nickel, Raney nickel, ruthenium chloride, and the like), in the presence or in the absence of acid (hydrochloric acid, sulfuric acid, hypochlorous acid, boric acid, tetrafluoroboric acid, acetic acid, p-toluenesulfonic acid, oxalic acid, triflucroacetic acid, formic acid, and the like), in a hydrogen atmosphere under normal pressure or with pressure added, in the presence of formic acid ammonium or in the presence of hydrazine at a temperature of about 0 to 200° C.

2) For example, the reaction is carried out using a metal reagent (zine, iron, tin, tin chloride, iron chloride, samarium, indium, sodium borohydride-nickel chloride and the like) in a water-miscible solvent (ethanol, methanol, tetrahydrofuran, and the like), in the presence or absence of acids (hydrochloric acid, hydrobromic acid, ammonium chloride, acetic acid, ammonium formate, and the like) at temperatures of about 0 to 150° C.

In a compound represented by the general formula (IIa) in the reaction scheme (Ia), when one $R^2$ is -$L^3$-$R^{11}$, $R^{11}$ is a 3- to 10-membered heterocycle, $L^3$ is —$CH_2$—, $R^{33}$ is a hydrogen atom, can be produced by replacing $R^{11-3}$—OH in the reaction scheme (Ij) into $R^{11-4}$—H ($R^{11-4}$ represents a 3- to 10-membered heterocycle-).

In the compound represented by the general formula (IIIa) in the reaction scheme (Ia), when a ring C is a compound represented by the general formula (IIIk):

[Chem. 33]

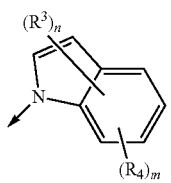

(wherein in the formula, an arrow represents a bonding site to $L^2$, and the other symbols are the same meaning as those in the [1]), the compound can be produced by the method shown in the following reaction scheme (Ik).

Reaction scheme (Ik)

[Chem. 34]

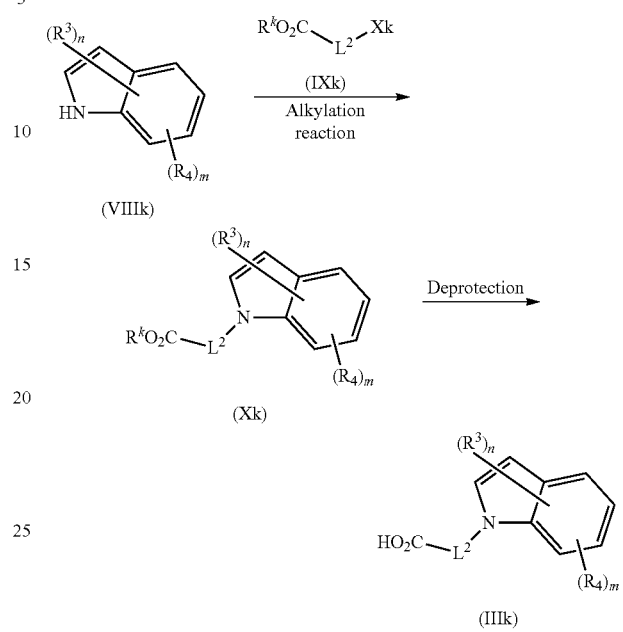

(wherein in the formula, Xk is a halogen atom, tosylate, or mesylate, $R^k$ is a protective group of a carboxy group, and the other symbols have the same meanings as defined in the above [1]).

Examples of the protective group for a carboxy group include a methyl group, an ethyl group, an allyl group, a t-butyl group, a trichloroethyl group, a benzyl (Bn) group, a phenacyl group, and the like.

In the reaction scheme (Ik), a compound represented by the general formula (Xk) is produced by substituting a compound represented by the general formula (VIIIk) and a compound represented by the general formula (IXk) to an alkylation reaction. The alkylation reaction is well-known. For example, a reaction is carried out in an organic solvent (dimethylformamide, dimethyl sulfoxide, chloroform, dichloromethane, diethyl ether, tetrahydrofuran, methyl t-butyl ether and the like) in the presence of base (sodium hydride and the like) at temperatures of about 0 to 100° C.

In the reaction scheme (Ik), a compound represented by the general formula (IIIk) is produced by subjecting a carboxy group of the compound represented by the general formula (Xk) to a deprotection reaction. The deprotection reaction of the carboxy group is well-known, and includes, for example:

(1) alkaline hydrolysis,
(2) deprotection reaction under acidic conditions,
(3) deprotection reaction by hydrogenolysis,
(4) deprotection reaction of silyl group,
(5) deprotection reaction using metal,
(6) deprotection reaction using a metal complex, and the like.

These methods will be specifically described:
(1) The deprotection reaction by alkaline hydrolysis condition is carried out, for example, in an organic solvent (methanol, tetrahydrofuran, dioxane, and the like) using hydroxide of alkaline metal (sodium hydroxide, potassium hydroxide, lithium hydroxide, and the like), hydroxide of alkaline earth metal (barium hydroxide, calcium hydroxide, and the like), or carbonate (sodium carbonate or potassium carbonate, and the like), or an aqueous solution thereof or a mixture thereof at temperatures of 0 to 40° C.

(2) The deprotection reaction in acidic conditions is carried out, for example, in an organic solvent (dichloromethane, chloroform, dioxane, ethyl acetate, anisole, and the like), organic acid (acetic acid, trifluoroacetic acid, methanesulfonic acid, p-tosyl acid, and the like), or in inorganic acid (hydrochloric acid, sulfuric acid, and the like) or a mixture thereof (hydrogen bromide/acetic acid, and the like) at temperatures of about 0 to 100° C.

(3) The deprotection reaction by hydrogenolysis is carried out, for example, in a solvent (ethers (tetrahydrofuran, dioxane, dimethoxyethane, diethyl ether, and the like), alcohols (methanol, ethanol, and the like), benzenes (benzene, toluene, and the like), ketones (acetone, methyl ethyl ketone, and the like), nitriles (acetonitrile, and the like), amides (dimethylformamide, and the like), water, ethyl acetate, acetic acid, or a mixture of two or more thereof, and the like) in the presence of a catalyst (palladium carbon, palladium black, palladium hydroxide, platinum oxide, Raney nickel, and the like), in a hydrogen atmosphere under normal pressure or with pressure added, or in the presence of ammonium formate at temperatures of 0 to 200° C.

(4) The deprotection reaction of a silyl group is carried out, for example, in a water-miscible organic solvent (tetrahydrofuran, acetonitrile, and the like), by using tetrabutylammonium fluoride at temperatures of 0 to 40° C.

(5) The deprotection reaction using metal is carried out, for example, in an acidic solvent (acetic acid, a buffer solution of pH 4.2 to 7.2, a mixed solution of the solution and an organic solvent such as tetrahydrofuran, and the like) in the presence of powder zinc with an ultrasonic wave applied, if necessary, at temperatures of 0 to 40° C.

(6) The deprotection reaction using a metal complex is carried out, for example, in an organic solvent (dichloromethane, dimethylformamide tetrahydrofuran, ethyl acetate, acetonitrile, dioxane, ethanol, and the like), water or a mixed solvent thereof in the presence of a trap reagent (tributyltin hydride, triethylsilane, dimedone, morpholine, diethylamine, pyrrolidine, and the like), an organic acid (acetic acid, formic acid, 2-ethylhexanic acid, and the like) and/or in the presence of an organic acid salt (sodium 2-ethylhexanate, potassium 2-ethylhexanate, and the like) in the presence or absence of a phosphine reagent (triphenylphosphine, and the like) using a metal complex (tetrakis(triphenylphosphine)palladium(O), dichlorobis (triphenylphosphine)palladium (II), palladium acetate (II), chlorotris(triphenylphosphine)rhodium (I), and the like) at temperatures of 0 to 40° C.

In addition to the above-described methods, the deprotection reaction can be carried out by, for example, the method described in T. W. Greene, Protective Groups in Organic Synthesis, Wiley, New York, 1999. Using property of these deprotection reactions can facilitate production of the objective compounds of the present invention, which can be easily understood by a person skilled in the art.

In the reaction scheme, compounds represented by the general formulae (IIa), (IIIa), (IIb), (IIIb), (IIc), (IIIc), (IId), (IIId), (IIe), (IIIe), (IIf), (IIIf), (IIg), (IIIg), (IIh), (IIIh), (IIi), (Vi), (VIj), (VIIIk), (IXk), (IIs) or (IIIs), which are used as a starting raw material, are well known, or can be easily produced by using methods described in, for example, a method described in Comprehensive Organic Transformations: A Guide to Functional Group Preparations 2nd Edition (Richard C. Larock, John Wiley & Sons Inc, 1999).

Furthermore, the compound of the present invention having an amino group, a carboxy group, or a hydroxyl group can be produced by carrying out a well-known deprotection reaction or a deprotection reaction as described in, for example, T. W. Greene, Protective Groups in Organic Synthesis, Wiley, New York, 1999, if necessary, after carrying out the reaction described in the above reaction scheme or after an appropriate reaction step using a compound protected by a protecting group commonly used for these groups, for example, a protecting group as described in T. W. Greene, Protective Groups in Organic Synthesis, Wiley, New York, 1999.

Among the compounds of the present invention represented by the general formula (I), compounds other than those described above can be produced by using Examples described in this specification or well-known methods, for example, the method described in Comprehensive Organic Transformations: A Guide to Functional Group Preparations 2nd Edition (Richard C. Larock, John Wiley & Sons Inc, 1999) in combination.

In the compounds of the present invention, compounds having an optical activity can also be produced by using optically active starting materials or reagents, or by optically resolving a racemic intermediate and then leading to a compound of the present invention, or by optically resolving a racemic compound of the present invention.

The optically resolving method is well-known, and includes, for example, forming a salt, complex or the like, with another optically active compound, carrying out recrystallization to isolate a target compound, or separate the target compound directly using a chiral column and the like.

In each reaction in the present specification, as is apparent to a skilled person in the art, the reactions involving heating can be carried out using a water bath, an oil bath, a sand bath or a microwave.

In each reaction in the present specification, a solid-supported reagent which is supported on a high molecular polymer (for example, polystyrene, polyacrylamide, polypropylene, polyethylene glycol, and the like) may be appropriately used.

In each reaction in the present specification, reaction products can be purified by usual purification methods, for example, by distillation at normal or reduced pressure, by high performance liquid chromatography using silica gel or magnesium silicate, thin layer chromatography, ion-exchange resin, scavenger resin, or column chromatography, or washing, recrystallization, or the like. The purification may be carried out after each reaction or after several reactions.

[Toxicity]

The compound of the present invention has sufficiently low toxicity, and can be safely used as pharmaceuticals.

[Application to Pharmaceuticals]

The problem of the present invention is to create a compound having selective and strong antagonistic activity against an $EP_4$ receptor and exhibit favorable pharmacodynamics, and to find a compound which is useful as an agent for preventing and/or treating diseases caused by activation of an $EP_4$ receptor.

Toxicity derived from unnecessary pharmacological action can be avoided by providing selectivity to other subtypes, which can be easily understood by a person skilled in the art.

Since the compound of the present invention exhibits selective and strong antagonistic activity against an $EP_4$ receptor, it is useful as an agent for preventing and/or treating the disease caused by activation of the $EP_4$ receptor, for example, a bone disease, a cancer, a systemic granulomatous disease, an immune disease, an allergic disease, atopic dermatitis, asthma, alveolar pyorrhea, gingivitis, periodontitis, Alzheimer's, Kawasaki disease, burn, multiple organ failure, chronic headache, pain, vasculitis, venous incompetence, varicose veins, aneurysm, aortic aneurysm, anal fistula, diabetes insipidus, stress, endometriosis, uterine adenomyosis, patent ductus arteriosus in neonates, cholelithiasis, or the like. A compound having further selective activation action of $EP_4$ receptor is preferable.

More specifically, examples of the bene diseases include osteoporosis, rheumatoid arthritis, osteoarthritis, and bone dysplasia. Examples of the cancer include breast cancer, ovarian cancer, large intestine cancer (for example, colon cancer), lung cancer (for example, non-small cell lung cancer), prostate cancer, head and neck cancer (for example, oral squamous cell carcinoma, head and neck squamous cell carcinoma, pharyngeal cancer, laryngeal cancer, tongue cancer, thyroid cancer, and acoustic nerve tumor), lymphoma (for example, B-cell lymphoma, and T-cell lymphoma), uveal malignant melanoma, thymoma, mesothelioma, esophagus cancer, stomach cancer, duodenal cancer, hepatocellular cancer, bile duct cancer, gallbladder cancer, pancreatic cancer, renal cell cancer, renal pelvis and ureter cancer, bladder cancer, penile cancer, testicular cancer, uterine cancer, vaginal cancer, vulvar cancer, skin cancer (for example, malignant melanoma), malignant bone tumor, soft tissue sarcoma, chondrosarcoma, leukemia, (for example, acute myeloid leukemia, acute lymphatic leukemia, chronic myeloid leukemia, and chronic lymphatic leukemia), osteomyelodysplasia syndrome, glioblastoma, multiple myeloma, and the like. Examples of the immunization disease include amyotrophic lateral sclerosis (ALS), multiple sclerosis, Sjoegren's syndrome, systemic lupus erythematosus, AIDS, and the like. Examples of the allergic disease include allergic conjunctivitis, allergic rhinitis, contact dermatitis, psoriasis, and the like. Examples of the chronic headaches include migraine, tension headache or a combination of these, or cluster headache, and the like.

The metabolic stability of the compound of the present invention can be measured by the in vitro metabolic stability test mentioned below. For the metabolic stability of the compound of the present invention, it is preferable to select a compound which exhibits appropriate kinetics by disease.

In one embodiment, for sustaining and enhancing the effect of medicine, a compound having high stability is selected. In one embodiment, for appropriately terminating the effect of medicine, a compound having low stability is selected.

[In Vitro Metabolic Stability Test]

The in vitro metabolic stability in liver microsomes or hepatocytes of a plurality of animal species including humans (for example, humans, mice, rats, dogs, and monkeys) can be evaluated as an indicator for selecting compounds having appropriate metabolic clearance. The compound of the present invention is added to the liver micro some reaction solution or hepatocyte suspension to carry out metabolic reaction at 37° C. Note here that to the liver microsome reaction solution, as a coenzyme, NADPH (oxidization metabolism) or UDPGA (glucuronidation) is added. To 60 minutes after the reaction is started, the reaction solution is collected over time, and added to a mixture solution of acetonitrile:ethanol (7:3) to stop the reaction. Then, treatment of removing protein by centrifugation is carried out. The obtained centrifugation supernatant is diluted with water, quantification of the compound of the present invention using LC-MS is carried out. The metabolic intrinsic clearance (CLint) is calculated from the concentration of the compound of the present invention at each time point.

Among the preventive and/or therapeutic effects of the compound of the present invention on diseases caused by activation of an $EP_4$ receptor, the antitumor effect can be evaluated by the in vivo pharmacological test mentioned below.

[In Vivo Pharmacological Test: Antitumor Effect in Allograft Model of Mouse Cancer Cell Tumor]

(1) Anti tumor effect of single use of compound of the present invention or effect of combination use with anti-mouse PD-1 antibody in allograft model of mouse large intestine cancer cell line MC38

In an allograft model of the mouse large intestine cancer cell line MC38 (Cancer Res. (1975), 35(9), p 2434-9), the antitumor effect of single use of the compound of the present invention or effect of combination use with anti-mouse PD-1 antibody are evaluated. MC38 is cultured in a DMEM medium including 10 vol % FBS, 100 units/mL Penicillin and 100 µg/mL of Streptomycin in a $CO_2$ incubator. On the day of transplantation, the culture supernatant is removed, and then the MC38 is washed with PBS and collected. The collected MC38 is suspended in PBS and used as cells for transplant. Under anesthesia, cells for transplant are subcutaneously transplanted into the right lateral abdominal regions of female C57BL/6 mice. To mice in the single use group and the combination use group of the compound of the present invention, the compound of the present invention is orally administered repeatedly. The anti-mouse PD-1 antibody is intraperitoneally administered to mice in the single use group and the combination use group of the anti-mouse PD-1 antibody. Note here that to the mice of the vehicle group and the anti-mouse PD-1 antibody group, a vehicle is orally administered repeatedly for the same time as that of the compound of the present invention. Furthermore, to mice of the vehicle group and the compound of the present invention group, PBS or mouse IgG1 antibody is intraperitoneally administered at the same time as that of the anti-mouse PD-1 antibody. The tumor volumes ($mm^3$) are calculated by the following mathematical formula 1 from the minor axis and the major axis of the tumor measured using a digital caliper. The effectiveness of the compound of the present invention is estimated by the tumor volumes.

$$\text{Tumor Volume}=[(\text{Minor Axis})^2 \times \text{Major Axis}]/2 \quad \text{[Math. 1]}$$

(2) Antitumor effect of single use of compound of the present invention and effect of combination use with anti-mouse PD-1 antibody in allograft model of mouse large intestine cancer cells CT26

In an allograft model of the mouse large intestine cancer cells CT26 (Cancer Res. (2013), 73(12), p 3591-603), the antitumor effect of single use of the compound of the present invention and effect of combination use of the compound of the present invention with anti-mouse PD-1 antibody are evaluated. CT26 is cultured in a RPMI medium including 10 vol % FBS, 2 mmol/L Glutamax, 100 units/mL Penicillin and 100 µg/mL of Streptomycin in a $CO_2$ incubator. On the day of transplantation, the culture supernatant is removed, and then the CT26 is washed with PBS and collected. The collected CT26 is suspended in PBS and used as cells for transplant. Under anesthesia, the cells for transplant are subcutaneously transplanted into the right lateral abdominal regions of female BALB/c mice. To mice in the single use group and the combination use group, the compound of the present invention is orally administered repeatedly. The anti-mouse PD-1 antibody is intraperitoneally administered to mice in the single use group and the combination use group of the anti-mouse PD-1 antibody. Note here that to mice of the vehicle group and the anti-mouse PD-1 antibody group, a vehicle is orally administered repeatedly for the same time as that of the compound of the present invention. Furthermore, to mice of the vehicle group and the compound of the present invention group, PBS or mouse IgG1 antibody is intraperitoneally administered at the same time as that of the anti-mouse PD-1 antibody. The tumor volumes (mm$^3$) are calculated by the following mathematical formula 2 from the minor axis and the major axis of the tumor measured using a digital caliper. The effectiveness of the compound of the present invention is estimated by the tumor volumes.

$$\text{Tumor Volume} = [(\text{Minor Axis})^2 \times \text{Major Axis}]/2 \qquad [\text{Math. 2}]$$

[Combination Drug]

The compound of the present invention may be administered as a combination drug in combination with other drugs in order to achieve the following purposes:

1) to complement and/or enhance the preventive and/or therapeutic effect of the compound,
2) to improve the kinetics and absorption of the compound, and reduce the dose of the compound, and/or
3) to reduce the side effects of the compound.

A combination drug of the compound of the present invention and other drugs may be administered in the form of a compounding agent including these components mixed into one formulation, or may be administered in separate formulations. The administration as separate formulations includes simultaneous administration and administration at different times. In the administration at different times, the compound of the present invention may be administered before the other drug. Alternatively, the other drug may be administered before the compound of the present invention. The method for the administration of these drugs may be the same as each other or different from each other.

Diseases on which the preventive and/or therapeutic effect of the above-mentioned combination drug works are not particularly limited and may be those in which the preventive and/or therapeutic effect of the compound of the present invention is complemented and/or enhanced.

Examples of the other drugs for complementing and/or enhancing the preventive and/or therapeutic effect of the compound of the present invention against aortic aneurysm include an HMG-CoA reductase inhibitor, a hypotensive agent, tetracycline antibiotics, and the like.

Examples of the HMG-CoA reductase inhibitor include pravastatin (sodium), simvastatin, fluvastatin (sodium), cerivastatin (sodium), itavastatin, atorvastatin (calcium hydrate), lovastatin, pitavastatin (calcium), and the like.

Examples of the hypotensive agents include calcium antagonists, angiotensin II antagonists, angiotensin converting enzyme inhibitors, phosphodiesterase 4 inhibitors, diuretics, prostaglandins, aldosterone antagonists, sympatholytic agents, and the like.

Examples of the calcium antagonist include nifedipine, benidipine hydrochloride, diltiazem hydrochloride, verapamil hydrochloride, nisoldipine, nitrendipine, bepridil hydrochloride, amlodipine besilate, lomerizine hydrochloride, efonidipine hydrochloride, and the like.

Examples of the angiotensin II antagonists include losartan (potassium), candesartan (cilexetil), valsartan, irbesartan, olmesartan (medoxomil), telmisartan, and the like.

Examples of the angiotensin-converting enzyme inhibitor include alacepril, imidapril hydrochloride, quinapril hydrochloride, temocapril hydrochloride, delapril hydrochloride, benazepril hydrochloride, captopril, trandolapril, perindopril, erbumine, enalapril maleate, and lisinopril.

Examples of the phosphodiesterase 4 inhibitors include silomilast, roflumilast, allofilin, atizoram, sipamfilin, and rolipram.

Examples of the diuretics include acetazolamide, aminophylline, isosorbide, dichlorophenamide, spironolactone, trichlormethiazide, furosemide, mannitol, methazolamide, mefruside, and the like.

Examples of the aldosterone antagonists include drospirenone, mertirapone, potassium canrenoate, canrenone, eplerenone, and the like.

Examples of the tetracycline antibiotics include doxycycline and the like.

Examples of the other drugs for complementing and/or enhancing the preventive and/or therapeutic effects on cancer of the compounds of the present invention include alkylating agents, antimetabolites, anticancer antibiotics, plant-based preparations, hormones, platinum compounds, topoisomerase inhibitors, kinase inhibitors, anti-CD 20 antibodies, anti-HER2 antibodies, anti-EGFR antibodies, anti-VEGF antibodies, proteasome inhibitors, HDAC inhibitors, immune checkpoint inhibitors, and immunomodulators.

Examples of the alkylating agent include cyclophosphamide, ifosfamide, dacarbazine, temozolomide, nimustine hydrochloride, ranimustine, bendamustine, thiotepa, and carbocone.

Examples of the antimetabolites include methotrexate, pemetrexed, fluorouracil, tegafur, tegafur uracil, tegafur gimestat otastat potassium, doxifluridine, capecitabine, cytarabine, gemcitabine hydrochloride, fludarabine, nelarabine, carmofur, and procarbazine hydrochloride, and the like.

Examples of the anticancer antibiotics include mitomycin C, doxorubicin hydrochloride, aclarubicin hydrochloride, pirarubicin hydrochloride, epirubicin, chromomycin A3, bleomycin, peplomycin sulfate, telarubicin, and the like.

Examples of the plant-based preparations include irinotecan hydrochloride, etoposide, vincristine sulfate, vinblastine sulfate, vindesine sulfate, vinorelbine tartrate, docetaxel hydrate, eribulin mesylate, paclitaxel, and the like.

Examples of the hormones include estramustine phosphate sodium, flutamide, bicalutamide, goserelin acetate, leuprorelin acetate, tamoxifen citrate, tremifene citrate, anastrozole, letrozole, exemestane, mepithiostane, medroxyprogesterone acetate, epitiostanol, fosfestrol, fadrozole hydrochloride hydrate, abiraterone, fulvestrant, aminoglutethimide, and the like.

Examples of the platinum compounds include carboplatin, cisplatin, nedaplatin, oxaliplatin, and the like.

Examples of the topoisomerase inhibitor include topotecan, sobuzoxane, and the like.

Examples of the kinase inhibitor include EGFR inhibitors such as erlotinib, gefitinib, and afatinib, HER2 inhibitors such as lapatinib, BCR-ABL inhibitors such as imatinib, ALK inhibitors such as crizotinib, multi-kinase inhibitors such as regorafenib, and dasatinib, and the like.

Examples of the anti-CD 20 antibodies include rituximab, ibritumomab, ibritumomab tiuxetan, ocrelizumab, and the like.

Examples of the anti-HER2 antibody include trastuzumab, trastuzumab emtansine, pertuzumab, and the like.

Examples of the anti-EGFR antibody include cetuximab, panitumumab, and the like.

Examples of the anti-VEGF antibody include bevacizumab and the like.

Examples of the proteasome inhibitor include bortezomib and the like.

Examples of the HDAC inhibitor include vorinostat.

Examples of the immune checkpoint inhibitor include anti-CTLA-4 antibodies such as ipilimumab, Tremelimumab, anti-PD-1 antibody (for example, human anti-human PD-1 monoclonal (neutralizing) antibody such as nivolumab, REGN-2810, humanized anti-human PD-1 monoclonal (neutralizing) antibodies such as Pembrolizumab, PDR-001, BGB-A317, and AMP-514 (MEDI0680)), anti-PD-L1 antibodies such as Atezolizumab (RG7446, MPDL3280A), Avelumab (PF-06834635, MSB0010718C), Durvalumab (MEDI4736), BMS-936559), anti-PD-L2 antibody, PD-L1 fusion protein, PD-L2 fusion protein such as AMP-224, anti-Tim-3 antibodies such as MBG453, anti-LAG-3 antibodies such as BMS-986016, and LAG525, anti-KIR antibodies such as Lirilumab, IDO1 inhibitors such as Epacadpstat and BMS-986205, and the like.

Examples of the immunomodulators include thalidomide, lenalidomide, pomalidomide, and the like.

Examples of the other drugs to complement and/or enhance the preventive and/or therapeutic effect of the compound of the present invention on pain include N-type calcium channel inhibitor, nitric oxide synthase (NOS) inhibitor, and cannabinoid-2 receptor stimulant, and the like.

Examples of the N-type calcium channel inhibitor include cilnidipine and the like.

Examples of the nitric oxide synthase (NOS) inhibitors include D-arginine, $N^G$-monomethyl-L-arginine, and the like.

The mass ratio of the compound of the present invention to other drugs is not particularly limited.

Any two or more other drugs may be administered in combination.

Furthermore, the other drugs to complement and/or enhance the preventive and/or therapeutic effect of the compound of the present invention include not only drugs which have been found to date but also drugs that will be found in the future based on the mechanism mentioned above.

[Formulation]

When the compound of the present invention is used, as a single agent or a combination drug used together with other drugs, for preventing and/or treating the above diseases, preparations are usually formed using the substance as the active ingredient and various additives or pharmaceutically acceptable carriers such as solvents and are administered as oral or parenteral preparation systemically or locally. The pharmaceutically acceptable carriers herein mean materials which are generally used for the preparation of drugs except for the active ingredients. The pharmaceutically acceptable carriers are preferably harmless carriers which do not show any pharmacological effect at the dosage of the preparation and which do not inhibit the treatment effect of the active ingredients. Furthermore, the pharmaceutically acceptable carriers can also be used to enhance effectiveness of the active ingredients and the preparations, make production of the drugs easy, stabilize quality or improve usability. Specifically, the materials described in "Japanese Pharmaceutical Excipients directory" (Yakuji Nippo, Limited, 2000) (edited by International Pharmaceutical Excipients Council Japan)", etc. may be appropriately selected according to intentions.

Examples of the dosage forms for administration include oral preparations (for example, tablets, capsules, granules, powders, oral solutions, syrups, and oral jelly agents), oro-mucosal preparations (for example, tablets for oro-mucosal application, sprays for oro-mucosal application, semi-solid preparations for oro-mucosal application, and gargles), preparations for injection (for example, injections), preparations for dialysis (for example, dialysis agents), preparations for inhalation (for example, and inhalations), preparations for ophthalmic application (for example, eye drop, and ophthalmic ointments), preparations for otorhinologic application (for example, ear drop), preparations for nasal application (for example, nasal drop), preparations for recta (for example, suppositories, semi-solid preparations for rectal application, enemas), preparations for vaginal application (for example, tablets for vaginal use, and suppositories for vaginal use), preparations for cutaneous application (for example, solid preparations for external use, liquids and solutions for external use, sprays, ointment, creams, gels, and patches), and the like.

Unless otherwise defined, all the technical and scientific terms and all the abbreviations used in this specification have the meaning as normally understood by a person skilled in the art of the present invention.

The contents of all the patent literatures and the non-patent literatures and the contents of the reference documents explicitly cited in this specification are incorporated herein as a part of the specification.

EXAMPLES

Hereinafter, the present invention is described in detail with reference to Examples, but the present invention is not limited thereto.

Solvents given in parentheses shown in chromatographic separation and TLC each indicate the elution solvent or the developing solvent used, and the ratio is expressed in ratio by volume.

The description of a solvent in a parenthesis in the NMR data shows a solvent used for measurement.

The compound names used in this specification are based on the computer program ACD/Name (registered trademark), the Chemdraw Ultra (version 12.0, manufactured by Cambridge Soft), or Lexichem Toolkit (version 1.4.2, manufactured by OpenEye Scientific Software), which generally generate chemical names according to IUPAC rules, or based on the IUPAC nomenclature.

LC-MS/ELSD was carried out in the following conditions. [column: YMC-Triart $C_{18}$ (particle diameter: $5 \times 10^{-6}$ m; column length: 50×4.6 mm I.D.); flow rate: 3.0 mL/min; column temperature: 30° C.; mobile phase (A): 0.05% trifluoroacetic acid aqueous solution; mobile phase (B): 0.05% trifluoroacetic acid-acetonitrile solution; gradient (ratio of mobile phase (A): mobile phase (B) is described): [0 min] 90:10; [1.0 min] 90:10; [1.5 min] 70:30; [4.5 min] 30:70; [5.0 min] 10:90; [6.0 min] 10:90; [6.2 min] 90:10; [7.0 min] 90:10; detector: UV (PDA), ELSD, MS]

HPLC retention time shows retention time in the conditions described in the LC-MS/ELSD.

Abbreviation symbols in the specification will be shown as follows.

THF: tetrahydrofuran

DMF: N,N-dimethylformamide

SFC: Supercritical fluid chromatography

Reference Example 1

N,3-dimethyl-1H-indole-6-carboxamide

Under a stream of nitrogen, a solution of 3-methylindole-6-carboxylic acid (CAS No., 201286-69-3, 50.0 g), methylamine hydrochloride (154 g), triethylamine (476 mL), 1-ethyl-3-[3-(dimethylamino) propyl]carbodiimide (54.6 g) and 1-hydroxybenzotriazole (43.6 g) in acetonitrile (1300 mL) was stirred overnight at 40° C. The solvent was removed by evaporation under reduced pressure, and then saturated brine was added to thereto, followed by extraction with ethyl acetate. The organic layer was washed with an aqueous solution of sodium hydroxide (1 mol/L), water, and saturated brine, dried over sodium sulfate, followed by concentration under reduced pressure. The resulting residue was washed with an ethyl acetate/hexane solution, and then dried under reduced pressure to obtain the title compound (46.7 g) having the following physical property values.

$^1$H-NMR (DMSO-$d_6$): δ 1.71, 2.26, 2.79, 5.27, 7.36, 7.45-7.57, 7.91, 8.29, 12.97.

Reference Example 2

Methyl 2-[3-methyl-6-(methylcarbamoyl)-1H-indol-1-yl]propanoate

Under a stream of nitrogen, to a solution of the compound (41.8 g) produced in Reference Example 1 in anhydrous THF (1000 mL), sodium hydride (10.7 g, 60%) was added in a divided manner over 10 minutes under ice cooling. The resulting mixture was stirred at room temperature for 30 minutes. Under ice cooling, solution of methyl 2-bromopropionate (40.8 g) in anhydrous tetrahydrofuran (100 mL) was added dropwise over 10 minutes, and then the resulting mixture was stirred at room temperature for two hours. Under ice cooling, water was added dropwise, and then saturated brine was added, followed by extraction with ethyl acetate. The organic layer was washed with saturated brine, and dried over sodium sulfate, followed by concentration under reduced pressure. The resulting residue was washed with tert-butylmethyl ether, and dried under reduced pressure to obtain the title compound (50.5 g) having the following physical property values.

$^1$H-NMR (CDCl$_3$): δ 1.79, 2.33, 3.04, 3.70, 5.21, 6.20, 7.15, 7.38, 7.54, 7.87.

Reference Example 3

2-[3-methyl-6-(methylcarbamoyl)-1H-indol-1-yl]propanoic acid

To a solution of the compound (50.5 g) produced in Reference Example 2 in methanol (250 mL) and THF (250 mL), an aqueous solution of sodium hydroxide (6 mol/L, 46 mL) was added, and the resulting mixture was stirred at room temperature for one hour. The solvent was removed by evaporation under reduced pressure, and then water and 6 mol/L hydrochloric acid were added to the resulting residue, followed by extraction with ethyl acetate. The resulting organic layer was washed with saturated brine, dried over anhydrous sodium sulfate, and then concentrated under reduced pressure to obtain the title compound (47.9 g) having the following physical property values.

$^1$H-NMR (CDCl$_3$): δ 1.88, 2.29, 2.98, 5.30, 6.33, 7.11-7.22, 7.41, 8.08.

Reference Example 4

Ethyl 4-[4-(hydroxymethyl)-2-nitrophenyl]butanoate

To a solution of ethyl 4-(4-formyl-2-nitrophenyl)butanoate (Reference Example 7 of WO 2016/111347, 18.3 g) in ethanol (180 mL), sodium borohydride (1.31 g) was added under ice cooling, and the resulting mixture was stirred for 30 minutes. To the reaction mixture, a saturated ammonium chloride aqueous solution was added. Then, the solvent was removed by evaporation under reduced pressure. Water was added to the resulting residue, followed by extraction with ethyl acetate. The organic layer was washed with saturated brine, dried over anhydrous sodium sulfate, and concentrated under reduced pressure to obtain the title compound (18.6 g) having the following physical property values.

$^1$H-NMR (CDCl$_3$): δ 1.27, 1.93-2.06, 2.38, 2.92, 4.14, 4.76, 7.36, 7.53, 7.92.

Reference Example 5

Ethyl 4-[2-amino-4-(hydroxymethyl)phenyl]butanoate

To a solution of the compound (18.6 g) produced in Reference Example 4 in ethanol (180 mL), palladium carbon (10% wet, 1.8 g) was added. The resulting mixture was stirred overnight under the hydrogen atmosphere at room temperature. The reaction mixture was filtered through celite (trade name), and the filtrate was concentrated under reduced pressure to obtain the title compound (16.1 g) having the following physical property values.

$^1$H-NMR (CDCl$_3$): δ 1.27, 1.83-1.96, 2.40, 2.45-2.57, 3.93, 4.16, 4.60, 6.66-6.75, 7.02.

Reference Example 6

Ethyl 4-[4-(hydroxymethyl)-2-{-[3-methyl-6-(methylcarbamoyl)-1H-indol-1-yl]propanamido}phenyl]butanoate To a solution of the compound (15.1 g) produced in Reference Example 5 and the compound (16.5 g) produced in Reference Example 3 in DMF (150 mL) and water (15 mL), 4-(4,6-dimethoxy-1,3,5-triazin-2-yl)-4-methylmorpholinium chloride n-hydrate (DMT-MM) (17.6 g) was added, and the resulting mixture was stirred at room temperature for three hours. Water was added to the reaction mixture, followed by extraction with ethyl acetate. The organic layer was washed with saturated brine, concentrated under reduced pressure to purify the resulting residue by silica gel column chromatography (NH silica gel, ethyl acetate→ethyl acetate:methanol=10:1) to obtain the title compound (16.1 g) having the following physical property values.

$^1$H-NMR (CDCl$_3$): δ 1.27, 1.42-1.54, 1.90, 1.96, 2.08-2.26, 2.36, 3.01, 4.17, 4.61, 5.44, 6.35, 7.00-7.10, 7.33, 7.45, 7.59, 7.91, 7.99.

Reference Example 7

Ethyl 4-(4-{[(methanesulfonyl)oxy]methyl}-2-{2-[3-methyl-6-(methylcarbamoyl)-1H-indol-1-yl]propanamido}phenyl)butanoate To a solution of the compound (600 mg) produced in Reference Example 6 and triethylamine (349 μL) in anhydrous THF (5 mL), methane sulfonyl chloride (145 μL) was added dropwise in the ice bath, and stirred as it is for three hours. Water was added to a reaction mixture, followed by extraction with ethyl acetate. The organic layer was washed with saturated brine, dried over anhydrous sodium sulfate, and then concentrated under reduced pressure. Then, the resulting residue as it is was used for the following reaction.

Example 1

4-{4-[(1,1-dioxide-1,2-thiazolidin-2-yl)methyl]-2-({2-[3-methyl-6-(methylcarbamoyl)-1H-indol-1-yl]propanoyl}amino)phenyl}butanoic acid

[Chem. 35]

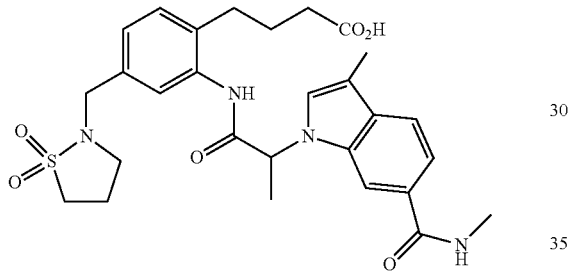

To a solution of the compound (58 mg) produced in Reference Example 7 in DMF (1 mL), cesium carbonate (51 mg) and 1,3-propanesultam (20 mg) were added, and the resulting mixture was stirred overnight at 50° C. The reaction mixture was filtered, and then the filtrate was concentrated under reduced pressure, and the resulting residue was purified by Biotage SNAP KP-NH (hexane:ethyl acetate). The resulting purified product was dissolved in dimethoxyethane (1 mL) and methanol (1 mL), then an aqueous solution of sodium hydroxide (2 mol/L, 130 μL) was added, and the resulting mixture was stirred overnight at room temperature. The reaction mixture was neutralized with a hydrochloric acid aqueous solution, followed by concentration under reduced pressure. The resulting residue was washed with water in slurry, and washed with acetonitrile in slurry to obtain the compound (46 mg) of the present invention having the following physical property values.

HPLC retention time (min): 2.90;
MS (ESI, Pos.): 555.23 (M+H)$^+$;
$^1$H-NMR (CDCl$_3$): δ 1.65-1.83, 2.24-2.61, 3.38, 3.13-3.25, 4.10-4.23, 5.78, 6.45, 7.03-7.13, 7.26, 7.51, 7.63, 8.19, 8.89, 9.41.

Examples 1-1 to 1-22

The same procedure as in Example 1 was carried out using the corresponding amine compounds or alcohol compounds instead of 1,3-propanesultam to obtain compounds of the present invention having the following physical property values.

Example 1-1

4-[2-({2-[3-methyl-6-(methylcarbamoyl)-1H-indol-1-yl]propanoyl}amino)-4-(4-morpholinylmethyl)phenyl]butanoic acid

[Chem. 36]

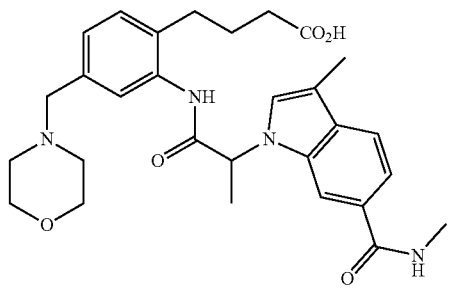

HPLC retention time (min): 2.30;
MS (ESI, Pos.): 521.33 (M+H)$^+$.

Example 1-2

4-{4-[(4-acetyl-1-piperazinyl)methyl]-2-({2-[3-methyl-6-(methylcarbamoyl)-1H-indol-1-yl]propanoyl}amino)phenyl}butanoic acid

[Chem. 37]

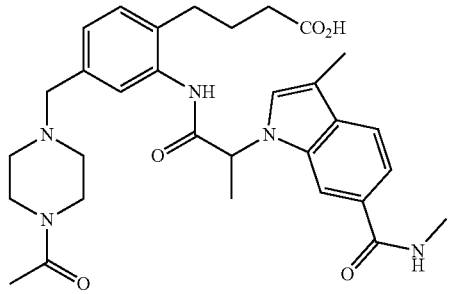

HPLC retention time (min): 2.25;
MS (ESI, Pos.): 562.42 (M+H)$^+$.

Example 1-3

4-{4-[(3,3-difluoro-1-pyrrolidinyl)methyl]-2-({2-[3-methyl-6-(methylcarbamoyl)-1H-indol-1-yl]propanoyl}amino)phenyl}butanoic acid HPLC retention time (min): 2.42;
MS (ESI, Pos.): 541.28 (M+H)$^+$.

Example 1-4

4-{2-({2-[3-methyl-6-(methylcarbamoyl)-1H-indol-1-yl]propanoyl}amino)-4-[(4-pyridinyloxy)methyl]phenyl}butanoic acid HPLC retention time (min): 2.37;
MS (ESI, Pos.): 529.27 (M+H)$^+$.

Example 1-5

4-[4-{[(2,6-dimethyl-4-pyridinyl)oxy]methyl}-2-({2-[3-methyl-6-(methylcarbamoyl)-1H-indol-1-yl]propanoyl}amino)phenyl]butanoic acid

[Chem. 38]

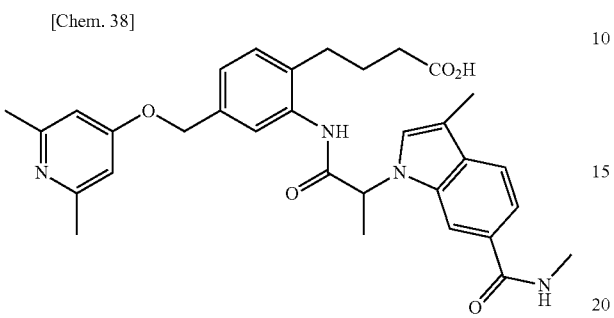

HPLC retention time (min): 2.57;
MS (ESI, Pos.): 557.29 (M+H)$^+$.
$^1$H-NMR (CDCl$_3$): δ 1.66-1.85, 2.31, 2.34-2.63, 3.10, 5.00-5.15, 5.81, 6.46, 6.64, 7.04-7.17, 7.22, 7.53, 7.62, 8.37, 8.89, 9.49.

Example 1-6

4-{2-({2-[3-methyl-6-(methylcarbamoyl)-1H-indol-1-yl]propanoyl}amino)-4-[(3-pyridinyloxy)methyl]phenyl}butanoic acid HPLC retention time (min): 2.45;
MS (ESI, Pos.): 529.34 (M+H)$^+$.

Example 1-7

4-[2-({2-[3-methyl-6-(methylcarbamoyl)-1H-indol-1-yl]propanoyl}amino)-4-{[(2-methyl-3-pyridinyl)oxy]methyl}phenyl]butanoic acid HPLC retention time (min): 2.45;
MS (ESI, Pos.): 543.28 (M+H)$^+$.

Example 1-8

4-[2-({2-[3-methyl-6-(methylcarbamoyl)-1H-indol-1-yl]propanoyl}amino)-4-{[(6-methyl-3-pyridinyl)oxy]methyl}phenyl]butanoic acid HPLC retention time (min): 2.47;
MS (ESI, Pos.): 543.28 (M+H)$^+$.

Example 1-9

4-[4-{[(2,6-dimethyl-3-pyridinyl)oxy]methyl}-2-({2-[3-methyl-6-(methylcarbamoyl)-1H-indol-1-yl]propanoyl}amino)phenyl]butanoic acid HPLC retention time (min): 2.54;
MS (ESI, Pos.): 557.29 (M+H)$^+$.

Example 1-10

4-{2-({2-[3-methyl-6-(methylcarbamoyl)-1H-indol-1-yl]propanoyl}amino)-4-[(5-pyrimidinyloxy)methyl]phenyl}butanoic acid HPLC retention time (min): 2.90;
MS (ESI, Pos.): 530.28 (M+H)$^+$.

Example 1-11

4-{2-({2-[3-methyl-6-(methylcarbamoyl)-1H-indol-1-yl]propanoyl}amino)-4-[(2-pyridinyloxy)methyl]phenyl}butanoic acid HPLC retention time (min): 2.74;
MS (ESI, Pos.): 529.27 (M+H)$^+$.

Example 1-12

4-[2-({2-[3-methyl-6-(methylcarbamoyl)-1H-indol-1-yl]propanoyl}amino)-4-{[(2-methyl-4-pyridinyl)oxy]methyl}phenyl]butanoic acid HPLC retention time (min): 2.50;
MS (ESI, Pos.): 543.22 (M+H)$^+$.

Example 1-13

4-{4-[(4-isopropyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.65;
MS (ESI, Pos.): 544.28 (M+H)$^+$.

Example 1-14

4-{4-[(4-chloro-1H-pyrazol-1-yl)methyl]-2-({2-[3-methyl-6-(methylcarbamoyl)-1H-indol-1-yl]propanoyl}amino)phenyl}butanoic acid

[Chem. 39]

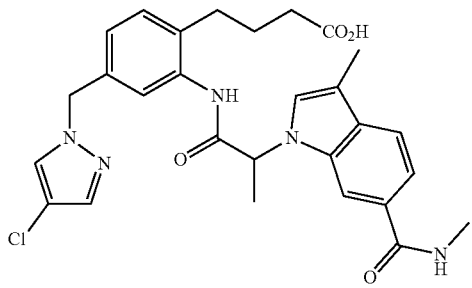

HPLC retention time (min): 3.47;
MS (ESI, Pos.): 536.28 (M+H)$^+$;

$^1$H-NMR (CDCl$_3$): δ 1.65-1.81, 2.29-2.60, 3.09, 5.15-5.29, 5.80, 6.45, 6.86, 7.06, 7.22, 7.37, 7.45, 7.54, 7.63, 8.29, 8.89, 9.46.

Example 1-15

4-{4-[(4-acetyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 2.88;
MS (ESI, Pos.): 544.67 (M+H)$^+$.

Example 1-16

4-{2-({2-[3-methyl-6-(methylcarbamoyl)-1H-indol-1-yl]propanoyl}amino)-4-[(4-propyl-1H-pyrazol-1-yl)methyl]phenyl}butanoic acid HPLC retention time (min): 3.69;
MS (ESI, Pos.): 544.28 (M+H)$^+$.

Example 1-17

4-[2-({2-[3-methyl-6-(methylcarbamoyl)-1H-indol-1-yl]propanoyl}amino)-4-{[4-(trifluoromethyl)-1H-pyrazol-1-yl]methyl}phenyl]butanoic acid HPLC retention time (min): 3.74;
MS (ESI, Pos.): 570.24 (M+H)$^+$.

Example 1-18

4-{4-[(3,5-dimethyl-1H-1,2,4-triazol-1-yl)methyl]-2-({2-[3-methyl-6-(methylcarbamoyl)-1H-indol-1-yl]propanoyl}amino)phenyl}butanoic acid HPLC retention time (min): 2.40;
MS (ESI, Pos.): 531.34 (M+H)$^+$.

Example 1-19

4-{4-[(3,5-dimethyl-4H-1,2,4-triazol-4-yl)methyl]-2-({2-[3-methyl-6-(methylcarbamoyl)-1H-indol-1-yl]propanoyl}amino)phenyl}butanoic acid HPLC retention time (min): 2.34;
MS (ESI, Pos.): 531.28 (M+H)$^+$.

Example 1-20

4-{4-[(2-methyl-1H-imidazol-1-yl)methyl]-2-({2-[3-methyl-6-(methylcarbamoyl)-1H-indol-1-yl]propanoyl}amino)phenyl}butanoic acid HPLC retention time (min): 2.34;
MS (ESI, Pos.): 516.27 (M+H)$^+$.

Example 1-21

4-[2-({2-[3-methyl-6-(methylcarbamoyl)-1H-indol-1-yl]propanoyl}amino)-4-{[(1-propyl-1H-pyrazol-4-yl)oxy]methyl}phenyl]butanoic acid HPLC retention time (min): 3.44;
MS (ESI, Pos.): 560.30 (M+H)$^+$.

Example 1-22

4-{4-[(4-ethyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.40;
MS (ESI, Pos.): 530.28 (M+H)$^+$.

Reference Example 8

Ethyl 4-[4-(chloromethyl)-2-{2-[3-methyl-6-(methylcarbamoyl)-1H-indol-1-yl]propanamido}phenyl]butanoate To a THF (10 mL) suspension of the compound (1 g) produced in Reference Example 6, triethylamine (0.58 mL) and methanesulfonyl chloride (0.24 mL) were added under ice cooling, and the resulting solution was stirred at room temperature for 90 minutes. To the reaction solution, lithium chloride (177 mL) was added and the resulting solution was stirred at room temperature for three hours. Furthermore, triethylamine (0.3 mL) and methanesulfonyl chloride (0.12 mL) were added thereto, and the resulting solution was stirred overnight at room temperature. The reaction solution was diluted with ethyl acetate, and the solution was washed with a saturated sodium hydrogencarbonate aqueous solution and saturated brine, dried over anhydrous sodium sulfate, and concentrated under reduced pressure to obtain the title compound (1.2 g) having the following physical property values.
TLC: Rf 0.77 (ethyl acetate);
$^1$H-NMR (CDCl$_3$): δ1.27, 1.44-1.62, 1.92, 2.11-2.25, 2.37, 3.02, 4.18, 4.52, 5.48, 6.27, 6.99-7.11, 7.32-7.37, 7.45, 7.59, 7.94-8.02, 8.15.

Example 2

4-{4-[(1,1-dioxide-1,2-thiazinan-2-yl)methyl]-2-({2-[3-methyl-6-(methylcarbamoyl)-1H-indol-1-yl]propanoyl}amino)phenyl}butanoic acid

[Chem. 40]

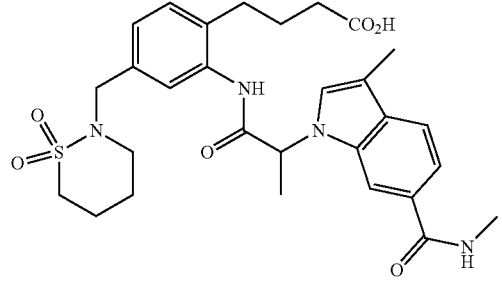

The same procedure as in Example 1 was carried out using the compound (52 mg) produced in Reference Example 8 instead of the compound produced in Reference Example 7, and using 4-butane sultam (21 mg) instead of 1,3-propanesultam to obtain compound (36.6 mg) of the present invention having the following physical property values.
HPLC retention time (min): 3.12;
MS (ESI, Pos.): 569.30 (M+H)$^+$;

$^1$H-NMR (CDCl$_3$): δ 1.59-1.67, 1.69-1.84, 2.14-2.28, 2.29-2.61, 3.03-3.14, 3.21-3.31, 4.24-4.32, 5.79, 6.45, 7.05-7.13, 7.22, 7.52, 7.62, 8.18, 8.90, 9.40.

Examples 2-1 to 2-27 (4)

The same procedure as in Example 1 was carried out using the compound produced in Reference Example 8 instead of the compound produced in Reference Example 7, using the corresponding cyclic compounds instead of 1,3-propanesultam, and using sodium hydride instead of cesium carbonate to obtain the compounds of the present invention having the following physical property values.

Example 2-1

4-[2-({2-[3-methyl-6-(methylcarbamoyl)-1H-indol-1-yl]propanoyl}amino)-4-{[(2H)-2-(trifluoromethyl)-1-pyrrolidinyl]methyl}phenyl]butanoic acid

[Chem. 41]

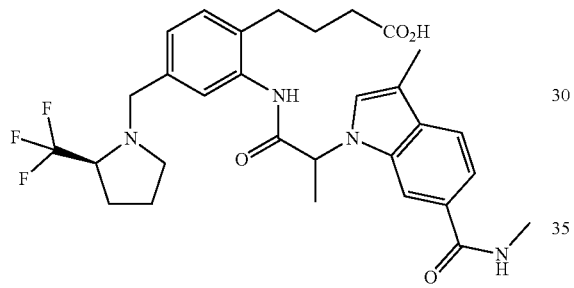

HPLC retention time (min): 2.94;
MS (ESI, Pos): 573.18 (M+H)$^+$.

Example 2-2

4-[2-({2-[3-methyl-6-(methylcarbamoyl)-1H-indol-1-yl]propanoyl}amino-4-{[(2R)-2-(trifluoromethyl)-1-pyrrolidinyl]methyl}phenyl]butanoic acid

[Chem. 42]

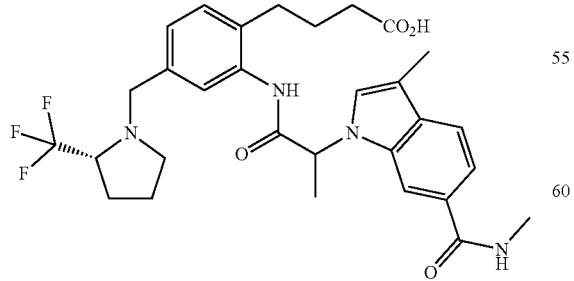

HPLC retention time (min): 2.97;
MS (ESI, Pos.): 573.18 (M+H)$^+$.

Example 2-3

4-{2-({2-[3-methyl-6-(methylcarbamoyl)-1H-indol-1-yl]propanoyl}amino)-4-[(4-pyridazinyloxy)methyl]phenyl}butanoic acid HPLC retention time (min): 2.52;
MS (ESI, Pos.): 530.09 (M+H)$^+$.

Example 2-4

4-{4-[(3,4-dimethyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.05;
MS (ESI, Pos.): 530.28 (M+H)$^+$.

Example 2-5

4-{4-[(3,4-dimethyl-1H-pyrazol-1-yl)methyl]-2-({2-[3-methyl-6-(methylcarbamoyl)-1H-indol-1-yl]propanoyl}amino)phenyl}butanoic acid

[Chem. 43]

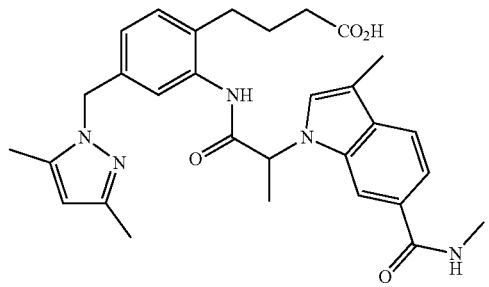

HPLC retention time (min): 2.84;
MS (ESI, Pos.): 530.21 (M+H)$^+$;
$^1$H-NMR (CDCl$_3$): δ 1.66-1.83, 2.18, 2.24, 2.30-2.58, 3.09, 5.18, 5.72-5.87, 6.46, 6.60, 7.00, 7.21, 7.52, 7.63, 8.17, 8.88, 9.38.

Example 2-6

The compound (23 mg) produced in Example 2-5 was subjected to optical resolution by SFC to obtain the compounds of the present invention having the following physical property values (Example 2-6 (1): 11.6 mg and Example 2-6 (2): 10.8 mg).

Example 2-6(1)

4-{4-[(3,4-dimethyl-1H-pyrazol-1-yl)methyl]-2-({2-[3-methyl-6-(methylcarbamoyl)-1H-indol-1-yl]propanoyl}amino)phenyl}butanoic acid (First Peak)

SFC retention time (min): 2.18 (CHIRALPAK IA 5 μm, 20 mm×250 (manufactured by Daicel Corporation); carbon dioxide:methanol=70:30).

Example 2-6(2)

4-{4-[(3,4-dimethyl-1H-pyrazol-1-yl)methyl]-2-({2-[3-methyl-6-(methylcarbamoyl)-1H-indol-1-yl]propanoyl}amino)phenyl}butanoic acid (Second Peak)

SFC retention time (min): 4.17 (CHIRALPAK IA 5 μm, 20 mm×250 (manufactured by Daicel Corporation); carbon dioxide:methanol=70:30).

Example 2-7

4-{2-({2-[3-methyl-6-(methylcarbamoyl)-1H-indol-1-yl]propanoyl}amino)-4-[(2-oxo-1-pyrrolidinyl)methyl]phenyl}butanoic acid HPLC retention time (min): 2.74;
MS (ESI, Pos.): 519.21 (M+H)$^+$.

Example 2-8

4-{2-({2-[3-methyl-6-(methylcarbamoyl)-1H-indol-1-yl]propanoyl}amino)-4-[(6-methyl-2-oxo-1(2H)pyridinyl)methyl]phenyl}butanoic acid HPLC retention time (min): 2.85;
MS (ESI, Pos.): 543.22 (M+H)$^+$.

Example 2-9

4-[2-({2-[3-methyl-6-(methylcarbamoyl)-1H-indol-1-yl]propanoyl}amino)-4-{[(6-methyl-2-pyridinyl)oxy]methyl}phenyl]butanoic acid HPLC retention time (min): 2.92;
MS (ESI, Pos.): 543.22 (M+H)$^+$.

Example 2-10

4-{2-({2-[3-methyl-6-(methylcarbamoyl)-1H-indol-1-yl]propanoyl}amino)-4-[(3-methyl-1H-pyrazol-1-yl)methyl]phenyl}butanoic acid HPLC retention time (min): 3.00;
MS (ESI, Pos.): 516.33 (M+H)$^+$.

Example 2-11

4-{4-[(3-ethyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.25;
MS (ESI, Pos.): 530.28 (M+H)$^+$.

Example 2-12

4-{4-[(3-cyclopropyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.32;
MS (ESI, Pos.): 542.28 (M+H)$^+$.

Example 2-13

4-{4-[(3-isopropyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.47;
MS (ESI, Pos.): 544.28 (M+H)$^+$.

Example 2-14

4-{4-[(4-chloro-3-methyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.62;
MS (ESI, Pos.): 550.16 (M+H)$^+$.

Example 2-15

4-{4-[(3-chloro-5-methyl-1H-pyrazol-1-yl)methyl]-2-({2-[3-methyl-6-(methylcarbamoyl)-1H-indol-1-yl]propanoyl}amino)phenyl}butanoic acid HPLC retention time (min): 3.59;
MS (ESI, Pos.): 550.23 (M+H)$^+$.

Example 2-16

4-[2-({2-[3-methyl-6-(methylcarbamoyl)-1H-indol-1-yl]propanoyl}amino)-4-{[3-(trifluoromethyl)-1H-pyrazol-1-yl}methyl]phenyl]butanoic acid

[Chem. 44]

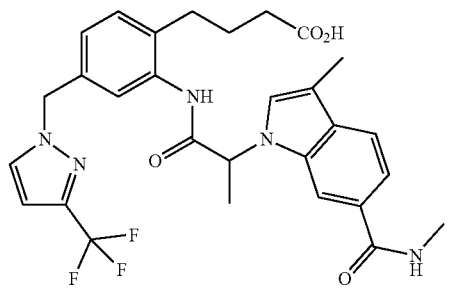

HPLC retention time (min): 3.80;
MS (ESI, Pos.): 570.18 (M+H)$^+$.

Example 2-17

The compound produced by Example 2-16 was subjected to optical resolution by SFC (CHIRALPAK IA 5 μm, 20 mm×250 (manufactured by Daicel Corporation); carbon dioxide:methanol=80:20) to obtain an optically active substance of the compound of the present invention having the following physical property values.

Example 2-17(1)

4-[2-({2-[3-methyl-6-(methylcarbamoyl)-1H-indol-1-yl]propanoyl}amino-4-{[3-(trifluoromethyl)-1H-pyrazol-1-yl}methyl]phenyl]butanoic acid (First Peak)

SFC retention time (min): 3.57 (CHIRALPAK IA 5 μm, 20 mm×250 (manufactured by Daicel Corporation); carbon dioxide:methanol=80:20).

Example 2-17 (2)

4-[2-({2-[3-methyl-6-(methylcarbamoyl)-1H-indol-1-yl]propanoyl}amino-4-{[3-(trifluoromethyl)-1H-pyrazol-1-yl}methyl]phenyl]butanoic acid (Second Peak)

SFC retention time (min): 4.97 (CHIRALPAK IA 5 μm, 20 mm×250 (manufactured by Daicel Corporation); carbon dioxide:methanol=80:20).
TLC: Rf 0.52 (chloroform:methanol=9:1);
$^1$H-NMR (CDCl$_3$): δ 1.50-1.66, 1.85, 2.07, 2.33, 2.34-2.44, 2.94, 5.31, 5.54, 6.57, 7.03, 7.18, 7.43, 7.49, 7.51-7.60, 7.74, 8.10.

Example 2-18

4-[4-(5,6-dihydrocyclopenta[c]pyrazol-2(4H)-ylmethyl)-2-({2-[3-methyl-6-(methylcarbamoyl)-1H-indol-1-yl]propanoyl}amino)phenyl]butanoic acid

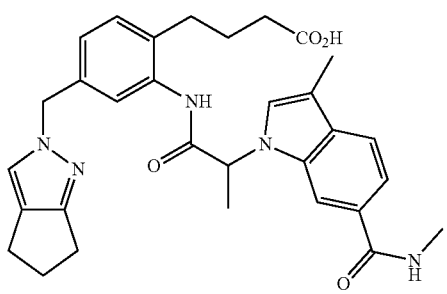

[Chem. 45]

HPLC retention time (min): 3.30;
MS (ESI, Pos.): 542.22 (M+H)$^+$;
$^1$H-NMR (CDCl$_3$): δ 1.66-1.81, 2.28-2.57, 2.61, 2.71, 3.09, 5.12-5.26, 5.79, 6.46, 6.88, 6.99-7.09, 7.22, 7.52, 7.64, 8.24, 8.90, 9.39.

Example 2-19

4-[4-(5,6-dihydrocyclopenta[c]pyrazol-1(4H)-ylmethyl)-2-({2-[3-methyl-6-(methylcarbamoyl)-1H-indol-1-yl]propanoyl}amino)phenyl]butanoic acid HPLC retention time (min): 3.02;
MS (ESI, Pos.): 542.22 (M+H)$^+$.

Example 2-20

4-[2-({2-[3-methyl-6-(methylcarbamoyl)-1H-indol-1-yl]propanoyl}amino)-4-(1H-1,2,3-triazol-1-ylmethyl)phenyl]butanoic acid HPLC retention time (min): 2.72;
MS (ESI, Pos.): 503.20 (M+H)$^+$.

Example 2-21

4-[2-({2-[3-methyl-6-(methylcarbamoyl)-1H-indol-1-yl]propanoyl}amino)-4-(2H-1,2,3-triazol-2-ylmethyl)phenyl]butanoic acid HPLC retention time (min): 3.04;
MS (ESI, Pos.): 503.26 (M+H)$^+$.

Example 2-22

4-[2-({2-[3-methyl-6-(methylcarbamoyl)-1H-indol-1-yl]propanoyl}amino)-4-(1H-1,2,4-triazol-1-ylmethyl)phenyl]butanoic acid HPLC retention time (min): 2.55;
MS (ESI, Pos.): 503.20 (M+H)$^+$.

Example 2-23

4-[2-({2-[3-methyl-6-(methylcarbamoyl)-1H-indol-1-yl]propanoyl}amino)-4-(4H-1,2,4-triazol-4-ylmethyl)phenyl]butanoic acid HPLC retention time (min): 2.35;
MS (ESI, Pos.): 503.20 (M+H)$^+$.

Example 2-24

4-{2-({2-[3-methyl-6-(methylcarbamoyl)-1H-indol-1-yl]propanoyl}amino)-4-[3-methyl-1H-1,2,4-triazol-1-yl)methyl]phenyl}butanoic acid HPLC retention time (min): 2.49;
MS (ESI, Pos.): 517.27 (M+H)$^+$.

Example 2-25

4-{2-({2-[3-methyl-6-(methylcarbamoyl)-1H-indol-1-yl]propanoyl}amino)-4-[3-methyl-4H-1,2,4-triazol-1-yl)methyl]phenyl}butanoic acid HPLC retention time (min): 2.32;
MS (ESI, Pos.): 517.27 (M+H)$^+$.

Example 2-26

The compound of Example 2-26(1) and the compound of Example 2-26(2) were obtained as a mixture.

Example 2-26(1)

4-[2-({2-[3-methyl-6-(methylcarbamoyl)-1H-indol-1-yl]propanoyl}amino)-4-{[5-methyl-3-(trifluoromethyl)-1H-pyrazol-1-yl]methyl}phenyl]butanoic acid

[Chem. 46]

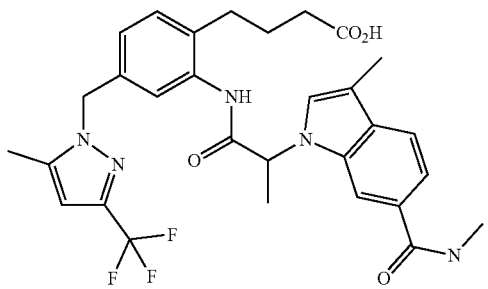

Example 2-26(2)

4-[2-({2-[3-methyl-6-(methylcarbamoyl)-1H-indol-1-yl]propanoyl}amino)-4-{[3-methyl-5-(trifluoromethyl)-1H-pyrazol-1-yl]methyl}phenyl]butanoic acid

[Chem. 47]

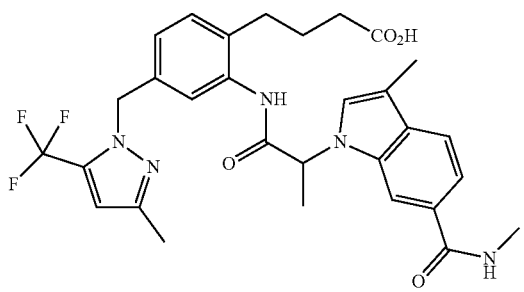

HPLC retention time (min): 3.90;
MS (ESI, Pos.): 584.19 (M+H)$^+$.

Example 2-27

The mixture produced in Example 2-26 was subjected to optical resolution by SFC to obtain an optically active substance of the compound of the present invention having the following physical property values.

Example 2-27(1)

4-[2-({2-[3-methyl-6-(methylcarbamoyl)-1H-indol-1-yl]propanoyl}amino)-4-{[3-methyl-5-(trifluoromethyl)-1H-pyrazol-1-yl]methyl}phenyl]butanoic acid
(First Peak)

SFC retention time (min): 1.82 (CHIRALPAK IA 5 μm, 20 mm×250 (manufactured by Daicel Corporation); carbon dioxide:methanol=70:30).

Example 2-27(2)

4-[2-({2-[3-methyl-6-(methylcarbamoyl)-1H-indol-1-yl]propanoyl}amino)-4-{[3-methyl-5-(trifluoromethyl)-1H-pyrazol-1-yl]methyl}phenyl]butanoic acid
(Second Peak)

SFC retention time (min): 2.25 (CHIRALPAK IA 5 μm, 20 mm×250 (manufactured by Daicel Corporation); carbon dioxide:methanol=70:30);
$^1$H-NMR (CDCl$_3$): δ 1.65-1.81, 2.25, 2.30-2.61, 3.09, 5.30, 5.79, 6.29, 6.46, 6.66, 7.03, 7.21, 7.54, 7.63, 8.22, 8.90, 9.45.

Example 2-27(3)

4-[2-({2-[3-methyl-6-(methylcarbamoyl)-1H-indol-1-yl]propanoyl}amino)-4-{[3-methyl-5-(trifluoromethyl)-1H-pyrazol-1-yl]methyl}phenyl]butanoic acid
(Third Peak)

SFC retention time (min): 2.87 (CHIRALPAK IA 5 μm, 20 mm×250 (manufactured by Daicel Corporation); carbon dioxide:methanol=70:30).

Example 2-27(4)

4-[2-({2-[3-methyl-6-(methylcarbamoyl)-1H-indol-1-yl]propanoyl}amino)-4-{[3-methyl-5-(trifluoromethyl)-1H-pyrazol-1-yl]methyl}phenyl]butanoic acid
(First Peak)

SFC retention time (min): 3.77 (CHIRALPAK IA 5 μm, 20 mm×250 (manufactured by Daicel Corporation); carbon dioxide:methanol=70:30);
$^1$H-NMR (CDCl$_3$): δ 1.65-1.81, 2.25, 2.30-2.61, 3.09, 5.30, 5.79, 6.29, 6.46, 6.66, 7.03, 7.21, 7.54, 7.63, 8.22, 8.90, 9.45.

Reference Example 9 tert-butyl 3-methyl-1H-indole-6-carboxylate

To a solution of 3-methyl-1H-indole-6-carboxylic acid (CASNo., 201286-69-3, 3 g) in toluene (30 mL), N,N-dimethylformamide di-tert-butyl acetal (20 mL) was added, and the resulting mixture was stirred at 120° C. for three hours. A saturated sodium dihydrogen phosphate aqueous solution was added to the reaction mixture, followed by extraction with hexane-ethyl acetate mixed solution. The organic layer was washed with water and saturated brine, dried over anhydrous sodium sulfate, and the resulting residue was purified by silica gel column chromatography to obtain the title compound (3.3 g) having the following physical property values.
TLC: Rf 0.48 (hexane:ethyl acetate=1:1);
$^1$H-NMR (CDCl$_3$): δ 1.62, 2.34, 7.09-7.13, 7.56, 8.05, 8.16.

Reference Example 10 tert-butyl 1-(1-methoxy-1-oxopropan-2-yl)-3-methyl-1H-indole-6-carboxylate

To a solution of the compound (1.1 g) produced in Reference Example 9 in DMF (10 mL), sodium hydride (213 mg) was added. The resulting mixture was stirred at 0° C. for 30 minutes, 2-bromomethyl propionate (0.8 mL) was added thereto, and the resulting mixture was stirred at room temperature for 16 hours. To the reaction mixture, a saturated ammonium chloride aqueous solution was added, followed by extraction with a hexane-ethyl acetate mixed solution. The organic layer was washed with water and saturated brine, dried over anhydrous sodium sulfate, and the resulting residue was purified by silica gel column chromatography to obtain the title compound (1.32 g) having the following physical property values.

TLC: Rf 0.54 (hexane:ethyl acetate=1:1);
$^1$H-NMR (CDCl$_3$): δ 1.62, 1.79, 2.31-2.36, 3.72, 5.20, 7.18, 7.54, 7.75, 7.98.

Reference Example 11

2-[6-(tert-butoxycarbonyl)-3-methyl-1H-indol-1-yl]propanoic acid

To a solution of the compound (1.9 g) produced in Reference Example 10 in methanol (5 mL) and 1,2-dimethoxyethane (5 mL), an aqueous solution of sodium hydroxide (2 mol/L, 5.9 mL) was added, and the resulting mixture was stirred at room temperature for 30 minutes. To the resulting mixture, hydrochloric acid was added, followed by extraction with ethyl acetate. The resulting organic layer was washed with water and saturated brine, dried over anhydrous sodium sulfate, and concentrated under reduced pressure to obtain the title compound (1.8 g) having the following physical property values.

TLC: Rf 0.26 (dichloromethane:methanol=9:1);
$^1$H-NMR (CDCl$_3$): δ 1.62, 1.85, 2.32-2.35, 5.24, 7.17, 7.54, 7.76, 7.99.

Reference Example 12

Ethyl 4-{4-[(4-methyl-1H-pyrazol-1-yl)methyl]-2-nitrophenyl}butanoate

The same procedure as in Reference Example 7 was carried out using the compound produced in Reference Example 4. To a solution of the resulting compound (54.4 g) in DMF (250 mL), cesium carbonate (76.7 g) and 4-methylpyrazole (14.2 g) were added. The resulting mixture was stirred overnight at room temperature. To the reaction mixture, water was added, followed by extraction with ethyl acetate. The organic layer was washed with saturated brine, dried over anhydrous sodium sulfate, and the resulting residue was purified by silica gel column chromatography (hexane:ethyl acetate=4:1 to 3:1) to obtain the title compound (44.9 g) having the following physical property values.

$^1$H-NMR (CDCl$_3$): δ 1.26, 1.88-2.02, 2.08, 2.37, 2.89, 4.13, 5.26, 7.19, 7.30-7.38, 7.71.

Reference Example 13

Ethyl 4-{2-amino-4-[(4-methyl-1H-pyrazol-1-yl)methyl]phenyl}butanoate

The same procedure as in Reference Example 5 was carried out using the compound (44.9 g) produced in Reference Example 12 to obtain the title compound (39.1 g) having the following physical property values.

$^1$H-NMR (CDCl$_3$): δ 1.27, 1.79-1.92, 2.05, 2.38, 2.49, 3.87, 4.15, 5.12, 6.50, 6.56, 6.97, 7.13, 7.32.

Reference Example 14 tert-butyl 1-(1-{2-(4-ethoxy-4-oxobutyl)-5-[(4-methyl-1H-pyrazol-1-yl)methyl]anilino}-1-oxopropan-2-yl)-3-methyl-1H-indole-6-carboxylate To an solution of the compound (1.5 g) produced in Reference Example 13 and the compound (1.7 g) produced in Reference Example 11 in acetonitrile (10 mL), triethylamine (1.4 mL), 1-hydroxy-7-azabenzotriazole (1.0 g), and 1-ethyl-3-[3-(dimethylamino)propyl]carbodiimide (EDC) (1.4 g) were added at room temperature. The reaction mixture was stirred at room temperature for 15 hours, and a saturated sodium hydrogen carbonate aqueous solution was added, followed by extraction with ethyl acetate. The organic layer was washed with saturated brine, and dried over anhydrous magnesium sulfate, followed by concentration under reduced pressure. The resulting residue was purified by silica gel column chromatography to obtain the title compound (2.4 g) having the following physical property values.

TLC: Rf 0.68 (hexane:ethyl acetate=1:2);
$^1$H-NMR (CDCl$_3$): δ 1.26, 1.45-1.58, 1.60, 1.90, 2.03, 2.13-2.28, 2.35-2.39, 4.17, 5.16, 5.51, 6.85, 7.01, 7.14, 7.30, 7.34-7.38, 7.57, 7.78, 8.01-8.11, 8.13.

Reference Example 15

1-(1-{2-(4-ethoxy-4-oxobutyl)-5-[(4-methyl-1H-pyrazol-1-yl)methyl]anilino}-1-oxopropan-2-yl)-3-methyl-1H-indole-6-carboxylic acid To a solution of the compound (2.3 g) produced in Reference Example 14 in dichloromethane (10 mL), trifluoroacetic acid (1.4 g) was added at room temperature. The resulting mixture was stirred for 30 minutes. To the reaction mixture, 5 mol/L of aqueous solution of sodium hydroxide was poured, followed by extraction with ethyl acetate. The resulting organic layer was washed with saturated brine, and dried over anhydrous magnesium sulfate, followed by concentration under reduced pressure. The resulting residue was washed with tert-butylmethylether-hexane mixed solution, and dried to obtain the title compound (1.9 g) having the following physical property values.

TLC: Rf 0.27 (dichloromethane:methanol=9:1);
$^1$H-NMR(CDCl$_3$): δ 1.28, 1.52-1.68, 1.91, 2.03, 2.20-2.44, 4.23, 5.17, 5.61, 6.86, 7.03, 7.15, 7.33, 7.45-7.49, 7.62, 7.87, 8.11, 8.30, 8.50.

Reference Example 16

Ethyl 4-{2-(2-{6-[ethyl(methyl)carbamoyl]-3-methyl-1H-indol-1-yl}propanamino)-4-[(4-methyl-1H-pyrazol-1-yl)methyl]phenyl}butanoate To a solution of the compound (80 mg) produced in Reference Example 15 and N-ethylmethylamine (32 μL) in THF (2 mL) and acetonitrile (1 mL), triethylamine (21 μL), 1-hydroxybenzotriazole (25 mg), and 1-ethyl-3-[3-(dimethylamino)propyl]carbodiimide (EDC) (31 mg) were added at room temperature, and the resulting mixture was stirred for three hours. The reaction mixture was concentrated under reduced pressure, and a saturated sodium dihydrogen phosphate aqueous solution was added to the resulting residue, followed by extraction with ethyl acetate. The organic layer was washed with saturated brine, dried over anhydrous magnesium sulfate and concentrated under reduced pressure to obtain the title compound (66 mg) having the following physical property values.

TLC: Rf 0.42 (dichloromethane:methanol=9:1);

$^1$H-NMR (CDCl$_3$): δ 0.95-1.31, 1.50, 1.89, 2.00-2.05, 2.13-2.28, 2.36, 2.86-3.14, 3.17-3.66, 4.06-4.23, 5.15, 5.37, 6.85, 7.02, 7.12-7.19, 7.29, 7.51, 7.57, 7.94, 8.02.

Example 3

4-{2-[(2-{6-[ethyl(methyl)carbamoyl]-3-methyl-1H-indol-1-yl}propanoyl)amino]-4-[(4-methyl-1H-pyrazol-1-yl)methyl]phenyl}butanoic acid

[Chem. 48]

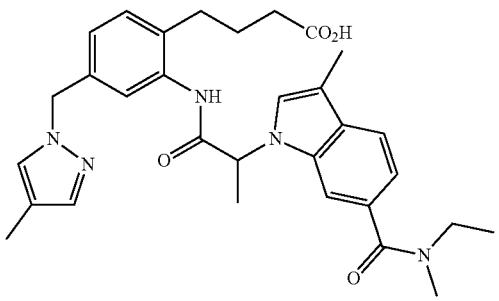

To a solution of the compound (66 mg) produced in Reference Example 16 in methanol (0.5 mL) and 1,2-dimethoxyethane (0.5 mL), an aqueous solution of sodium hydroxide (2 mol/L, 0.2 mL) was added, and the resulting mixture was stirred at room temperature for 17 hours. To the reaction mixture, cation exchange resin AG-50W (trade name) was added, and filtered, and then the filtrate was concentrated under reduced pressure to obtain a compound (41 mg) of the present invention having the following physical property values.

TLC: Rf 0.33 (dichloromethane:methanol=9:1);

$^1$H-NMR (CDCl$_3$): δ 1.28, 1.59, 1.69, 2.06, 2.12-2.54, 3.09, 3.40-3.71, 5.23, 5.60, 6.86, 7.02, 7.10, 7.20, 7.34, 7.41, 7.51, 8.22, 8.28, 9.29.

Example 3-1

The compound (30 mg) produced in Example 3 was subjected to optical resolution by SFC to obtain compounds of the present invention having the following physical property values (Example 3-1 (1): 11.1 mg, Example 3-2 (2): 10.6 mg).

Example 3-1(1)

4-{2-[(2-{6-[ethyl(methyl)carbamoyl]-3-methyl-1H-indol-1-yl}propanoyl)amino]-4-[(4-methyl-1H-pyrazol-1-yl)methyl]phenyl}butanoic acid (First Peak)

SFC retention time (min): 1.90 (CHIRALPAK IA 5 μm, 20 mm×250 (manufactured by Daicel Corporation); carbon dioxide:methanol=70:30).

Example 3-1(2)

4-{2-[(2-{6-[ethyl(methyl)carbamoyl]-3-methyl-1H-indol-1-yl}propanoyl)amino]-4-[(4-methyl-1H-pyrazol-1-yl)methyl]phenyl}butanoic acid (Second Peak)

SFC retention time (min): 3.44 (CHIRALPAK IA 5 μm, 20 mm×250 (manufactured by Daicel Corporation); carbon dioxide:methanol=70:30).

Examples 3-2 to 3-19

The same procedure as in Example 16→Example 3 was carried out using the compound produced in Reference Example 15, and the corresponding amine compounds instead of N-ethylmethylamine to obtain the compounds of the present invention having the following physical property values. Furthermore, the resulting compound was subjected to optical resolution by SFC to obtain an optically active substance of the compound of the present invention having the following physical property values.

Example 3-2

4-{2-({2-[6-(ethylcarbamoyl)-3-methyl-1H-indol-1-yl]propanoyl}amino)-4-[(4-methyl-1H-pyrazol-1-yl)methyl]phenyl}butanoic acid

[Chem. 49]

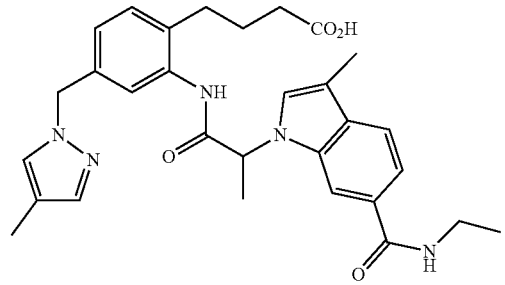

TLC: Rf 0.45 (dichloromethane:methanol=9:1);

1H-NMR (d$_6$-DMSO): δ 1.13, 1.54, 1.73, 1.95, 2.03, 2.26, 2.34-2.55, 3.21-3.42, 5.13, 5.50, 6.96, 7.12, 7.18, 7.22, 7.42-7.51, 7.51-7.58, 8.18, 8.42, 9.75, 12.02.

Example 3-3(1)

4-{2-({2-[6-(ethylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 2.19 (CHIRALPAK IA 5 μm, 20 mm×250 (manufactured by Daicel Corporation); carbon dioxide:methanol=70:30).

Example 3-3(2)

4-{2-({2-[6-(ethylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 3.93 (CHIRALPAK IA 5 μm, 20 mm×250 (manufactured by Daicel Corporation); carbon dioxide:methanol=70:30).

Example 3-4

4-{2-({2-[3-methyl-6-(propylcarbamoyl)-1H-indol-1-yl]propanoyl}amino)-4-[(4-methyl-1H-pyrazol-1-yl)methyl]phenyl}butanoic acid

[Chem. 50]

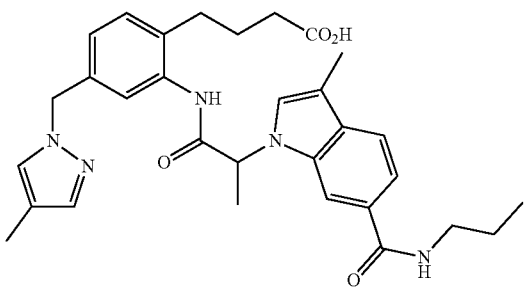

TLC: Rf 0.45 (dichloromethane:methanol=9:1);
$^1$H-NMR (DMSO-d$_6$): δ 0.86, 1.55, 1.74, 1.94, 2.06, 2.26, 2.33-2.43, 3.15-3.50, 5.13, 5.49, 6.94, 7.12, 7.19, 7.26, 7.43-7.51, 7.51-7.59, 8.11, 8.41, 9.7, 12.03.

Example 3-5(1)

4-{2-({2-[3-methyl-6-(propylcarbamoyl)-1H-indol-1-yl]propanoyl}amino)-4-[(4-methyl-1H-pyrazol-1-yl)methyl]phenyl}butanoic acid (First Peak)

SFC retention time (min): 5.44 (CHIRALPAK IA 5 μm, 20 mm×250 (manufactured by Daicel Corporation); carbon dioxide:methanol=70:30).

Example 3-5(2)

4-{2-({2-[3-methyl-6-(propylcarbamoyl)-1H-indol-1-yl]propanoyl}amino)-4-[(4-methyl-1H-pyrazol-1-yl)methyl]phenyl}butanoic acid (Second Peak)

SFC retention time (min): 7.08 (CHIRALPAK IA 5 μm, 20 mm×250 (manufactured by Daicel Corporation); carbon dioxide:methanol=70:30).

Example 3-6

4-{2-({2-[6-(isopropylcarbamoyl)-3-methyl-1H-indol-1-yl]propanoyl}amino)-4-[(4-methyl-1H-pyrazol-1-yl)methyl]phenyl}butanoic acid

[Chem. 51]

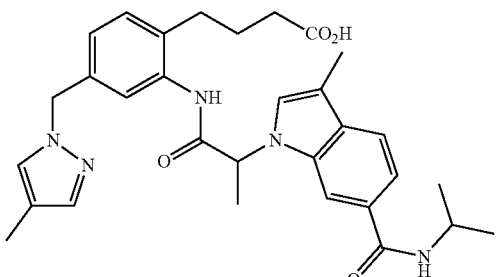

TLC: Rf 0.46 (dichloromethane:methanol=9:1);
$^1$H-NMR (DMSO-d$_6$): δ 1.16, 1.55, 1.74, 1.95, 2.05, 2.25, 2.32-2.44, 4.14, 5.13, 5.49, 6.94, 7.10, 7.19, 7.23, 7.42-7.60, 8.05, 8.11, 9.69, 12.04.

Example 3-7(1)

4-{2-({2-[6-(isopropylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 1.88 (CHIRALPAK IA 5 μm, 20 mm×250 (manufactured by Daicel Corporation); carbon dioxide:methanol=70:30).

Example 3-7(2)

4-{2-({2-[6-(isopropylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 3.25 (CHIRALPAK IA 5 μm, 20 mm×250 (manufactured by Daicel Corporation); carbon dioxide:methanol=70:30).

Example 3-8

4-{2-[(2-{6-[(2-methoxyethyl)carbamoyl]-3-methyl-1H-indol-1-yl}propanoyl)amino]-4-[(4-methyl-1H-pyrazol-1-yl)methyl]phenyl}butanoic acid

[Chem. 51]

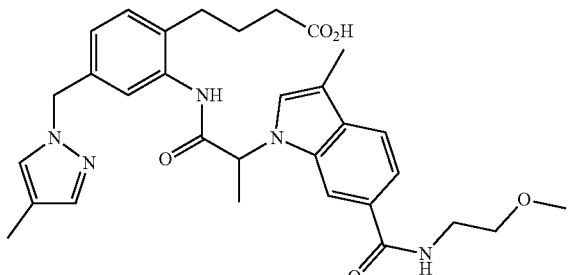

TLC: Rf 0.42 (dichloromethane:methanol=9:1);
$^1$H-NMR (DMSO-d$_6$): δ 1.54, 1.71, 1.94, 2.05, 2.28, 2.39, 3.26, 3.47, 5.13, 5.51, 6.92, 7.12, 7.19, 7.28, 7.43-7.60, 8.14, 8.44, 9.80, 12.06.

Example 3-9(1)

4-{2-[(2-{6-[(2-methoxyethyl)carbamoyl]-3-methyl-1H-indol-1-yl}propanoyl)amino]-4-[(4-methyl-1H-pyrazol-1-yl)methyl]phenyl}butanoic acid (First Peak)

SFC retention time (min): 2.57 (CHIRALPAK IA 5 μm, 20 mm×250 (manufactured by Daicel Corporation); carbon dioxide:methanol=70:30).

Example 3-9(2)

4-{2-[(2-{6-[(2-methoxyethyl)carbamoyl]-3-methyl-1H-indol-1-yl}propanoyl)amino]-4-[(4-methyl-1H-pyrazol-1-yl)methyl]phenyl}butanoic acid (Second Peak)

SFC retention time (min): 4.99 (CHIRALPAK IA 5 µm, 20 mm×250 (manufactured by Daicel Corporation); carbon dioxide:methanol=70:30).

Example 3-10

4-{2-({2-[6-(dimethylcarbamoyl)-3-methyl-1H-indol-1-yl]propanoyl}amino)-4-[(4-methyl-1H-pyrazol-1-yl)methyl]phenyl}butanoic acid

[Chem. 53]

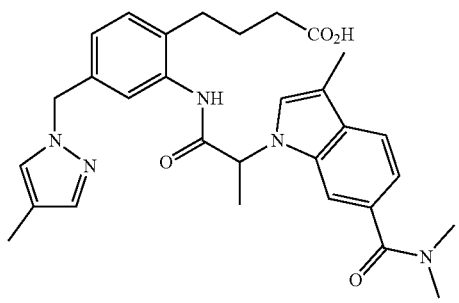

TLC: Rf 0.42 (dichloromethane:methanol=9:1);
$^1$H-NMR (CDCl$_3$): δ 1.55-1.67, 1.69, 2.06, 2.13-2.37, 2.38-2.55, 3.19, 5.20, 5.67, 6.82, 7.03, 7.11, 7.20, 7.32, 7.42, 7.50, 8.21, 9.29.

Example 3-11(1)

4-{2-({2-[6-(dimethylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 2.77 (CHIRALPAK IA 5 µm, 20 mm×250 (manufactured by Daicel Corporation); carbon dioxide:methanol=70:30).

Example 3-11(2)

4-{2-({2-[6-(dimethylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 5.57 (CHIRALPAK IA 5 µm, 20 mm×250 (manufactured by Daicel Corporation); carbon dioxide:methanol=70:30).

Example 3-12

4-{-[(4-methyl-1H-pyrazol-1-yl)methyl]-2-({2-[3-methyl-6-(1-pyrrolidinylcarbonyl)-1H-indol-1-yl]propanoyl}amino)phenyl}butanoic acid TLC: Rf 0.42 (dichloromethane:methanol=9:1);
$^1$H-NMR (DMSO-d$_6$): δ 1.53, 1.72, 1.83, 1.95, 2.01, 2.27, 2.34-2.61, 3.36-3.54, 5.10, 5.49, 6.92, 7.11, 7.18, 7.22, 7.27, 7.44, 7.51, 7.78, 9.92, 12.06.

Example 3-13(1)

4-{-[(4-methyl-1H-pyrazol-1-yl)methyl]-2-({2-[3-methyl-6-(1-pyrrolidinylcarbonyl)-1H-indol-1-yl]propanoyl}amino)phenyl}butanoic acid (First Peak)

SFC retention time (min): 2.96 (CHIRALPAK IA 5 µm, 20 mm×250 (manufactured by Daicel Corporation); carbon dioxide:methanol=70:30).

Example 3-13(2)

4-{-[(4-methyl-1H-pyrazol-1-yl)methyl]-2-({2-[3-methyl-6-(1-pyrrolidinylcarbonyl)-1H-indol-1-yl]propanoyl}amino)phenyl}butanoic acid (Second Peak)

SFC retention time (min): 7.58 (CHIRALPAK IA 5 µm, 20 mm×250 (manufactured by Daicel Corporation); carbon dioxide:methanol=70:30).

Example 3-14

4-{2-({2-[3-methyl-6-(1-piperidinylcarbonyl)-1H-indol-1-yl]propanoyl}amino)-4-[(4-methyl-1H-pyrazol-1-yl)methyl]phenyl}butanoic acid TLC: Rf 0.42 (dichloromethane:methanol=9:1);
$^1$H-NMR (DMSO-d$_6$): δ 1.30-1.61, 1.72, 1.95, 2.01, 2.27, 2.37-2.48, 3.16-3.45, 5.10, 5.54, 6.92, 7.03, 7.11, 7.18, 7.35, 7.44, 7.51, 7.63, 10.20.

Example 3-15(1)

4-{2-({2-[3-methyl-6-(1-piperidinylcarbonyl)-1H-indol-1-yl]propanoyl}amino)-4-[(4-methyl-1H-pyrazol-1-yl)methyl]phenyl}butanoic acid (First Peak)

SFC retention time (min): 2.50 (CHIRALPAK IA 5 µm, 20 mm×250 (manufactured by Daicel Corporation); carbon dioxide:methanol=70:30).

Example 3-15(2)

4-{2-({2-[3-methyl-6-(1-piperidinylcarbonyl)-1H-indol-1-yl]propanoyl}amino)-4-[(4-methyl-1H-pyrazol-1-yl)methyl]phenyl}butanoic acid (Second Peak)

SFC retention time (min): 5.41 (CHIRALPAK IA 5 µm, 20 mm×250 (manufactured by Daicel Corporation); carbon dioxide:methanol=70:30).

Example 3-16

4-{2-({2-[6-(cyclopropylcarbamoyl)-3-methyl-1H-indol-1-yl]propanoyl}amino)-4-[(4-methyl-1H-pyrazol-1-yl)methyl]phenyl}butanoic acid TLC: Rf 0.45 (dichloromethane:methanol=9:1);
$^1$H-NMR (DMSO-$d_6$): δ 0.54-0.70, 1.52, 1.68, 1.96, 2.02, 2.26, 2.33-2.52, 2.81-2.90, 5.13, 5.50-5.74, 6.91, 7.11, 7.19, 7.35-7.43, 7.44-7.56, 8.23, 8.60, 10.20, 12.02.

Example 3-17(1)

4-{2-({2-[6-(cyclopropylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 3.03 (CHIRALPAK IA 5 μm, 20 mm×250 (manufactured by Daicel Corporation); carbon dioxide:methanol=70:30).

Example 3-17(2)

4-{2-({2-[6-(cyclopropylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 5.92 (CHIRALPAK IA 5 μm, 20 mm×250 (manufactured by Daicel Corporation); carbon dioxide:methanol=70:30).

Example 3-18

4-{2-({2-[3-methyl-6-(4-morpholinylcarbonyl)-1H-indol-1-yl]propanoyl}amino)-4-[(4-methyl-1H-pyrazol-1-yl)methyl]phenyl}butanoic acid TLC: Rf 0.43 (dichloromethane:methanol=9:1);
$^1$H-NMR (DMSO-$d_6$): δ 1.43-1.62, 1.72, 1.95, 2.04, 2.27, 2.32-2.53, 3.37-3.70, 5.12, 5.41, 6.97, 7.08, 7.12, 7.19, 7.45, 7.54, 7.65, 9.65, 12.06.

Example 3-19

4-{2-[(2-{6-[(cyclopropylmethyl)carbamoyl]-3-methyl-1H-indol-1-yl}propanoyl)amino]-4-[(4-methyl-1H-pyrazol-1-yl)methyl]phenyl}butanoic acid

[Chem. 54]

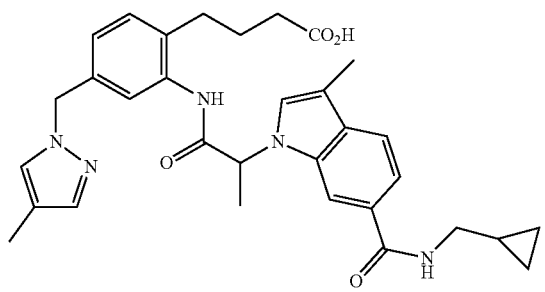

TLC: Rf 0.43 (dichloromethane:methanol=9:1);
$^1$H-NMR (DMSO-$d_6$): δ 0.17-0.28, 0.35-0.48, 0.94-1.16, 1.56, 1.73, 1.95, 2.06, 2.27, 2.31-2.50, 3.17, 5.13, 5.46, 6.96, 7.13, 7.19, 7.22, 7.44-7.62, 8.10, 8.42, 9.67, 12.03.

Example 3-20(1)

4-{2-[(2-{6-[(cyclopropylmethyl)carbamoyl]-3-methyl-1H-indol-1-yl}propanoyl)amino]-4-[(4-methyl-1H-pyrazol-1-yl)methyl]phenyl}butanoic acid (First Peak)

SFC retention time (min): 2.78 (CHIRALPAK IA 5 μm, 20 mm×250 (manufactured by Daicel Corporation); carbon dioxide:methanol=70:30).

Example 3-20(2)

4-{2-[(2-{6-[(cyclopropylmethyl)carbamoyl]-3-methyl-1H-indol-1-yl}propanoyl)amino]-4-[(4-methyl-1H-pyrazol-1-yl)methyl]phenyl}butanoic acid (Second Peak)

SFC retention time (min): 5.37 (CHIRALPAK IA 5 μm, 20 mm×250 (manufactured by Daicel Corporation); carbon dioxide:methanol=70:30).

Reference Example 17

Reference Example 17(1)

Ethyl 4-(4-[(3-cyclopropyl-1H-1,2,4-triazol-1-yl)methyl]-2-{2-[3-methyl-6-(methylcarbamoyl)-1H-indol-1-yl]propanamido}phenyl)butanoate

Reference Example 17(2)

Ethyl 4-(4-[(5-cyclopropyl-1H-1,2,4-triazol-1-yl)methyl]-2-{2-[3-methyl-6-(methylcarbamoyl)-1H-indol-1-yl]propanamido}phenyl)butanoate To a DMF (1 mL) suspension of sodium hydride (60% in mineral oil, 15 mg), 3-cyclopropyl-1H-1,2,4-triazole (53 mg) was added in an argon atmosphere, and the resulting mixture was stirred at 50° C. for 30 minutes. A DMF (1 mL) solution of the compound (120 mg) produced in Reference Example 8 was added thereto, and the mixture was stirred overnight at 50° C. The reaction solution was diluted with ethyl acetate, washed with a saturated sodium hydrogen carbonate aqueous solution and saturated brine, and dried over anhydrous sodium sulfate, followed by concentration under reduced pressure. The resulting residue was purified by silica gel column chromatography and HPLC (acetonitrile:water=5:95→35:65) to obtain the title compounds having the following physical property values (the compound of Reference Example 17(1): 26 mg and the compound of Reference Example 17(2): 13 mg).

Reference Example 17(1)

TLC: Rf 0.52 (ethyl acetate:methanol=10:1);
$^1$H-NMR (CDCl$_3$): δ 0.88-0.96, 1.27, 1.42-1.54, 1.85-2.08, 2.09-2.28, 2.36, 3.00, 4.17, 5.14, 5.46, 6.40-6.49, 6.90, 7.03, 7.33, 7.46, 7.58, 7.86, 8.00-8.07.

Reference Example 17(2)

TLC: Rf 0.52 (ethyl acetate:methanol=10:1);
$^1$H-NMR (CDCl$_3$): δ 0.99-1.08, 1.27, 1.39-1.53, 1.76-1.95, 2.07-2.25, 2.36, 3.01, 4.17, 5.32, 5.46, 6.31-6.42, 6.80, 7.00, 7.34, 7.45, 7.59, 7.73, 7.96-8.10.

Example 4

4-{4-[3-cyclopropyl-1H-1,2,4-triazol-1-yl)methyl]-2-({2-[3-methyl-6-(methylcarbamoyl)-1H-indol-1-yl]propanoyl}amino)phenyl}butanoic acid

[Chem. 55]

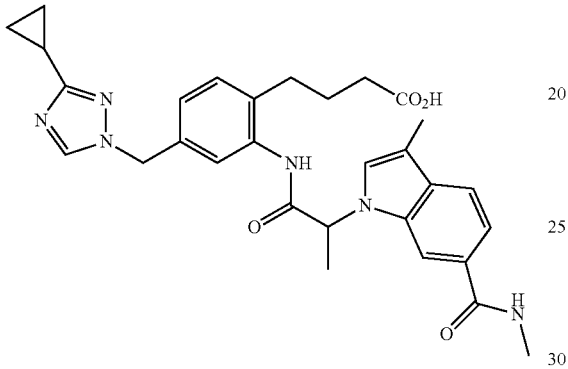

The same procedure as in Example 3 using the compound of Reference Example 17(1) to obtain the compound of the present invention having the following physical property values.
TLC: Rf 0.51 (dichloromethane:methanol=10:1);
$^1$H-NMR (DMSO-d$_6$): δ 0.67-0.88, 1.55, 1.73, 1.82-1.94, 2.05, 2.27, 2.32-2.67, 2.80, 5.18, 5.46, 7.02, 7.16, 7.27, 7.46, 7.48-7.56, 8.11, 8.24-8.33, 8.37, 9.68, 12.03.

Example 4-1

The compound of Example 4 was subjected to optical resolution by SFC to obtain an optically active substance of the compound of the present invention having the following physical property values.

Example 4-1(1)

4-{4-[(3-cyclopropyl-1H-1,2,4-triazol-1-yl)methyl]-2-({2-[3-methyl-6-(methylcarbamoyl)-1H-indol-1-yl]propanoyl}amino)phenyl}butanoic acid (First Peak)

SFC retention time (min): 3.03 (CHIRALPAK IA 5 μm, 20 mm×250 (manufactured by Daicel Corporation); carbon dioxide:methanol=70:30).

Example 4-1(2)

4-{4-[(3-cyclopropyl-1H-1,2,4-triazol-1-yl)methyl]-2-({2-[3-methyl-6-(methylcarbamoyl)-1H-indol-1-yl]propanoyl}amino)phenyl}butanoic acid (Second Peak)

SFC retention time (min): 5.21 (CHIRALPAK IA 5 μm, 20 mm×250 (manufactured by Daicel Corporation); carbon dioxide:methanol=70:30).

Example 4-2

4-{4-[(3-cyclopropyl-1H-1,2,4-triazol-1-yl)methyl]-2-({2-[3-methyl-6-(methylcarbamoyl)-1H-indol-1-yl]propanoyl}amino)phenyl}butanoic acid The same procedure as in Example 3 was carried out using the compound of Reference Example 17(2) to obtain the compound of the present invention having the following physical property values.
TLC: Rf 0.51 (dichloromethane:methanol=10:1);
$^1$H-NMR (DMSO-d$_6$): δ 0.76-0.99, 1.55, 1.73, 2.05, 2.09-2.21, 2.27, 2.32-2.65, 2.80, 5.37, 5.47, 6.94-7.00, 7.15, 7.25-7.31, 7.45, 7.48-7.55, 7.70, 8.11, 8.23-8.34, 9.67, 12.02.

Example 4-3

The compound of Example 4-2 was subjected to optical resolution by SFC to obtain an optically active substance of the compound of the present invention having the following physical property values.

Example 4-3(1)

4-{4-[(5-cyclopropyl-1H-1,2,4-triazol-1-yl)methyl]-2-({2-[3-methyl-6-(methylcarbamoyl)-1H-indol-1-yl]propanoyl}amino)phenyl}butanoic acid (First Peak)

SFC retention time (min): 2.70 (CHIRALPAK IA 5 μm, 20 mm×250 (manufactured by Daicel Corporation); carbon dioxide:methanol=70:30).

Example 4-3(2)

4-{4-[(5-cyclopropyl-1H-1,2,4-triazol-1-yl)methyl]-2-({2-[3-methyl-6-(methylcarbamoyl)-1H-indol-1-yl]propanoyl}amino)phenyl}butanoic acid (Second Peak)

SFC retention time (min): 3.97 (CHIRALPAK IA 5 μm, 20 mm×250 (manufactured by Daicel Corporation); carbon dioxide:methanol=70:30).

Example 4-4 to Example 4-15(2)

The same procedure as in Reference Example 17 and Example 3 using the compound of Reference Example 8 and the corresponding heterocyclic compounds instead of 3-cyclopropyl-1H-1,2,4-triazole to obtain the compounds of the present invention having the following physical property values. The obtained compound of the present invention was subjected to optical resolution by SFC to obtain an optically active substance of the compound of the present invention having the following physical property values.

Example 4-4

4-{2-({2-[3-methyl-6-(methylcarbamoyl)-1H-indol-1-yl]propanoyl}amino)-4-[(3-methyl-2-oxo-1(2H)-pyridinyl)methyl]phenyl}butanoic acid TLC: Rf 0.38 (chloroform:methanol=9:1);
$^1$H-NMR (DMSO-d$_6$): δ 1.47-1.61, 1.73, 1.95, 2.05, 2.27, 2.32-2.42, 2.80, 5.12, 5.46, 6.95, 7.12, 7.16-7.27, 7.41-7.57, 8.10, 8.29, 9.67, 12.03.

Example 4-5

4-[2-({2-[3-methyl-6-(methylcarbamoyl)-1H-indol-1-yl]propanoyl}amino)-4-(1H-pyrazol-1-ylmethyl)phenyl]butanoic acid TLC: Rf 0.42 (chloroform:methanol=9:1);
$^1$H-NMR (DMSO-$d_6$): δ 1.48-1.61, 1.73, 2.05, 2.27, 2.32-2.44, 2.80, 5.22, 5.46, 6.21, 6.96, 7.13, 7.22, 7.40, 7.45, 7.52, 7.75, 8.10, 8.29, 9.67, 12.03.

Example 4-6

4-[2-({2-[3-methyl-6-(methylcarbamoyl)-1H-indol-1-yl]propanoyl}amino)-4-{[3-(1,3-thiazol-2-yl)-1H-pyrazol-1-yl]methyl}phenyl]butanoic acid TLC: Rf 0.49 (chloroform:methanol=9:1);
$^1$H-NMR (DMSO-$d_6$): δ 1.47-1.63, 1.72, 2.00-2.11, 2.26, 2.32-2.51, 2.80, 5.31, 5.48, 6.73, 7.04, 7.17, 7.34, 7.45, 7.49-7.56, 7.64, 7.82, 7.93, 8.12, 8.31, 9.72, 12.05.

Example 4-7

4-{4-[(4-fluoro-1H-pyrazol-1-yl)methyl]-2-({2-[3-methyl-6-(methylcarbamoyl)-1H-indol-1-yl]propanoyl}amino)phenyl}butanoic acid

[Chem. 56]

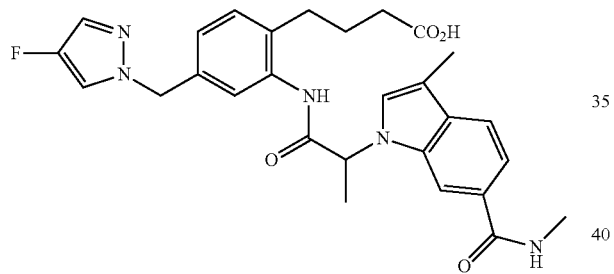

TLC: Rf 0.34 (hexane:ethyl acetate=1:3);
$^1$H-NMR (DMSO-$d_6$): δ 1.49-1.62, 1.74, 2.06, 2.28, 2.43-2.55, 2.82, 5.13, 5.46, 7.00, 7.15, 7.26, 7.41-7.48, 7.53, 7.92, 8.12, 8.29, 9.66, 12.05.

Example 4-8(1)

4-{4-[(4-fluoro-1H-pyrazol-1-yl)methyl]-2-({2-[3-methyl-6-(methylcarbamoyl)-1H-indol-1-yl]propanoyl}amino)phenyl}butanoic acid (First Peak)

SFC retention time (min): 3.07 (CHIRALPAK IC 5 μm, 20 mm×250 (manufactured by Daicel Corporation); carbon dioxide:methanol=75:25).

Example 4-8(2)

4-{4-[(4-fluoro-1H-pyrazol-1-yl)methyl]-2-({2-[3-methyl-6-(methylcarbamoyl)-1H-indol-1-yl]propanoyl}amino)phenyl}butanoic acid (Second Peak)

SFC retention time (min): 5.07 (CHIRALPAK IC 5 μm, 20 mm×250 (manufactured by Daicel Corporation); carbon dioxide:methanol=75:25).

Example 4-9

4-{4-[(4-fluoro-3,5-dimethyl-1H-pyrazol-1-yl)methyl]-2-({2-[3-methyl-6-(methylcarbamoyl)-1H-indol-1-yl]propanoyl}amino)phenyl}butanoic acid TLC: Rf 0.32 (hexane:ethyl acetate=1:3);
$^1$H-NMR (DMSO-$d_6$): δ 1.47-1.63, 1.74, 2.03-2.12, 2.28, 2.42-2.48, 2.82, 5.06, 5.46, 6.84, 7.11-7.19, 7.46, 7.53, 8.11, 8.28, 9.64, 12.05.

Example 4-10(1)

4-{4-[(4-fluoro-3,5-dimethyl-1H-pyrazol-1-yl)methyl]-2-({2-[3-methyl-6-(methylcarbamoyl)-1H-indol-1-yl]propanoyl}amino)phenyl}butanoic acid (First Peak)

SFC retention time (min): 5.07 (CHIRALPAK IA 5 μm, 20 mm×250 (manufactured by Daicel Corporation); carbon dioxide:methanol=70:30).

Example 4-10(2)

4-{4-[(4-fluoro-3,5-dimethyl-1H-pyrazol-1-yl)methyl]-2-({2-[3-methyl-6-(methylcarbamoyl)-1H-indol-1-yl]propanoyl}amino)phenyl}butanoic acid (Second Peak)

SFC retention time (min): 4.38 (CHIRALPAK IA 5 μm, 20 mm×250 (manufactured by Daicel Corporation); carbon dioxide:methanol=70:30).

Example 4-11

4-[2-({2-[3-methyl-6-(methylcarbamoyl)-1H-indol-1-yl]propanoyl}amino)-4-{[5-(trifluoromethyl)-2H-tetrazol-2-yl]methyl}phenyl]butanoic acid TLC: Rf 0.55 (hexane:ethyl acetate=1:3);
$^1$H-NMR (DMSO-$d_6$): δ 1.50-1.65, 1.71-1.78, 2.02-2.13, 2.28, 2.37-2.52, 2.76-2.83, 5.48, 6.03, 7.16-7.28, 7.42-7.55, 8.11, 8.28, 9.71, 12.05.

Example 4-12(1)

4-[2-({2-[3-methyl-6-(methylcarbamoyl)-1H-indol-1-yl]propanoyl}amino)-4-{[5-(trifluoromethyl)-2H-tetrazol-2-yl]methyl}phenyl]butanoic acid (First Peak)

SFC retention time (min): 3.12 (CHIRALPAK IC 5 μm, 20 mm×250 (manufactured by Daicel Corporation); carbon dioxide:methanol=85:15).

Example 4-12(2)

4-[2-({2-[3-methyl-6-(methylcarbamoyl)-1H-indol-1-yl]propanoyl}amino)-4-{[5-(trifluoromethyl)-2H-tetrazol-2-yl]methyl}phenyl]butanoic acid (Second Peak)

SFC retention time (min): 4.25 (CHIRALPAK IC 5 μm, 20 mm×250 (manufactured by Daicel Corporation); carbon dioxide:methanol=85:15).

Example 4-13

4-[2-({2-[3-methyl-6-(methylcarbamoyl)-1H-indol-1-yl]propanoyl}amino)-4-{[5-(trifluoromethyl)-1H-tetrazol-1-yl]methyl}phenyl]butanoic acid TLC: Rf 0.49 (hexane:ethyl acetate=1:3);
$^1$H-NMR (DMSO-$d_6$): δ 1.48-1.61, 1.75, 2.03-2.12, 2.27, 2.40-2.54, 2.81, 5.48, 5.80, 7.06, 7.22, 7.38, 7.45, 7.53, 8.09, 8.29, 9.66, 12.05.

Example 4-14

4-{4-[(5-isopropyl-2H-tetrazol-2-yl)methyl]-2-({2-[3-methyl-6-(methylcarbamoyl)-1H-indol-1-yl]propanoyl}amino)phenyl}butanoic acid TLC: Rf 0.35 (hexane:ethyl acetate=1:3);
$^1$H-NMR (DMSO-$d_6$): δ 1.26, 1.51-1.62, 1.74, 2.03-2.20, 2.27, 2.35-2.50, 2.80, 3.15, 5.46, 5.78, 7.08, 7.20, 7.35, 7.45, 7.53, 8.10, 8.28, 9.67, 12.05.

Example 4-15

4-{4-[(5-isopropyl-1H-tetrazol-2-yl)methyl]-2-({2-[3-methyl-6-(methylcarbamoyl)-1H-indol-1-yl]propanoyl}amino)phenyl}butanoic acid TLC: Rf 0.33 (hexane:ethyl acetate=1:3);
$^1$H-NMR (DMSO-$d_6$): δ 1.15, 1.48-1.60, 1.73, 2.02-2.16, 2.27, 2.35-2.48, 2.80, 3.33, 5.46, 5.61, 7.00, 7.19, 7.31, 7.46, 7.53, 8.11, 8.29, 9.67, 12.06.

Reference Example 18

Ethyl 4-[4-(azidomethyl)-2-{2-[3-methyl-6-(methylcarbamoyl)-1H-indol-1-yl]propanamido}phenyl]butanoate To a DMF (5 mL) solution of the compound (800 mg) produced in Reference Example 8, sodium azide (125 mg) was added, and the resulting mixture was stirred overnight at 50° C. for six hours, and at 75° C. for two hours. DMSO (5 mL) was added to the reaction solution and the reaction solution was stirred at 75° C. for one hour. Sodium azide (50 mg) was added thereto and the resulting mixture was stirred overnight at 75° C. The reaction solution was diluted with ethyl acetate, and washed with a saturated sodium hydrogencarbonate aqueous solution and saturated brine, dried over anhydrous sodium sulfate, followed by concentration under reduced pressure. The resulting residue was purified by silica gel column chromatography to obtain the title compound (610 mg) having the following physical property values.

TLC: Rf 0.52 (hexane:ethyl acetate=1:3);
$^1$H-NMR (CDCl$_3$): δ 1.27, 1.44-1.65, 1.92, 2.11-2.25, 2.37, 3.02, 4.18, 4.28, 5.48, 6.27, 6.97-7.03, 7.06, 7.34, 7.46, 7.60, 7.95-8.02, 8.07.

Reference Example 19

To a THF (20 mL) suspension of the compound (310 mg) produced in Reference Example 18, triphenylphosphine (193 mg) and water (1 mL) were added, and the resulting mixture was stirred overnight at room temperature. Triphenylphosphine (193 mg) was added to the reaction solution, and the resulting mixture was stirred at 50° C. for 12 hours. The reaction solution was diluted with ethyl acetate, followed by extraction with diluted hydrochloric acid (0.5 mol/L). The water layer was adjusted to have pH8 by an aqueous solution of sodium hydroxide (2 mol/L) and a saturated sodium carbonate aqueous solution, followed by extraction with ethyl acetate. The organic layer was washed with saturated brine, dried over anhydrous sodium sulfate, and then concentrated under reduced pressure to obtain the title compound (230 mg) having the following physical property values.

TLC: Rf 0.41 (ethyl acetate:methanol=10:1, NH$_2$-TLC);
$^1$H-NMR (CDCl$_3$): δ 1.27, 1.42-1.65, 1.92, 2.10-2.24, 2.37, 3.02, 3.79, 4.17, 5.47, 6.31, 6.95-7.04, 7.34, 7.46, 7.60, 7.87, 7.96-8.02.

Reference Example 20

Ethyl 4-(4-[(3-ethyl-4H-1,2,4-triazol-4-yl)methyl]-2-{2-[3-methyl-6-(methylcarbamoyl)-1H-indol-1-yl]propanamido}phenyl)butanoate To a dichloromethane (1 mL) solution of propanehydrazide (31 mg), 1,1-dimethoxy-N,N-dimethylmethaneamine (46 mg) was added, and the resulting mixture was stirred at room temperature for four hours. A solution of the compound (100 mg) produced in Reference Example 19 in acetic acid (1 mL) was added to the resulting reaction mixture, and heated at 150° C. for 30 minutes by using microwave. The reaction mixture was purified by silica gel column chromatography (Yamazen NH silica gel) to obtain the title compound (54 mg) having the following physical property values.

TLC: Rf 0.11 (ethyl acetate:methanol=10:1);
$^1$H-NMR (CDCl$_3$): δ 1.24-1.37, 1.42-1.65, 1.92, 2.15-2.28, 2.38, 2.67, 3.02, 4.20, 4.99, 5.45-5.55, 6.23-6.33, 6.60-6.66, 7.03, 7.34, 7.39-7.45, 7.59, 8.01-8.10, 8.16.

Example 5

4-{4-[(3-ethyl-4H-1,2,4-triazol-4-yl)methyl]-2-({2-[3-methyl-6-(methylcarbamoyl)-1H-indol-1-yl]propanoyl}amino)phenyl}butanoic acid

[Chem. 57]

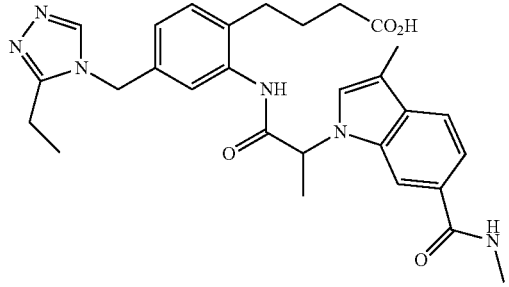

The same procedure as in Example 3 was carried out using the compound produced in Reference Example 20 to obtain the compound of the present invention having the following physical property values.

TLC: Rf 0.39 (dichloromethane:methanol=10:1);
$^1$H-NMR (CDCl$_3$): δ 1.36, 1.62-1.76, 2.30-2.63, 2.73, 3.09, 5.04, 5.81, 6.46-6.55, 6.64, 7.07, 7.25, 7.53, 7.60, 8.09, 8.28, 8.89, 9.53.

Reference Example 21

Ethyl 4-(2-{2-[3-methyl-6-(methylcarbamoyl)-1H-indol-1-yl]propanamido}-4-{[4-(trifluoromethyl)-1H-1,2,3-triazol-1-yl]methyl}phenyl)butanoate To a solution of the compound (80 mg) produced in Reference Example 18 in tert-butyl alcohol (5 mL), water (1 mL), and dimethyl sulfoxide (4 mL), sodium ascorbate (16 mg) and copper sulfate (II) (2.5 mg) were added. Then, the reaction vessel was replaced with trifluoroacetylene, and was stirred at room temperature for five hours. Water was added to the reaction mixture, followed by extraction with ethyl acetate. The organic layer was washed with water and saturated brine, dried over anhydrous sodium sulfate, and concentrated under reduced pressure to obtain the title compound (92 mg) having the following physical property values.

TLC: Rf 0.39 (hexane:ethyl acetate=1:3);

$^1$H-NMR (CDCl$_3$): δ 1.36, 1.62-1.76, 2.30-2.63, 2.73, 3.09, 5.04, 5.81, 6.46-6.55, 6.64, 7.07, 7.25, 7.53, 7.60, 8.09, 8.28, 8.89, 9.53.

Example 6

4-[2-({2-[3-methyl-6-(methylcarbamoyl)-1H-indol-1-yl]propanoyl}amino)-4-{[4-(trifluoromethyl)-1H-1,2,3-triazol-yl]methyl}phenyl]butanoic acid

[Chem. 58]

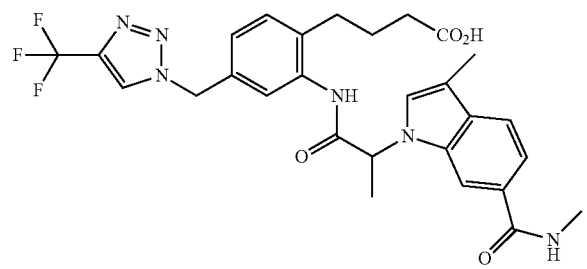

The same procedure as in Example 3 was carried out using the compound produced in Reference Example 21 to obtain the title compounds having the following physical property values.

TLC: Rf 0.39 (dichloromethane:methanol=10:1);

$^1$H-NMR (CDCl$_3$): δ 1.56, 1.74, 2.03-2.12, 2.26, 2.34-2.54, 2.81, 5.46, 5.61, 7.13, 7.21, 7.41-7.47, 7.54, 8.11, 8.29, 8.96, 9.69, 12.05.

Example 6-1

The compound of the present invention 6 was subjected to optical resolution by SFC to obtain an optically active compound of the present invention having the following physical property values.

Example 6-1(1)

4-[2-({2-[3-methyl-6-(methylcarbamoyl)-1H-indol-1-yl]propanoyl}amino)-4-{[4-(trifluoromethyl)-1H-1,2,3-triazol-yl]methyl}phenyl]butanoic acid (First Peak)

SFC retention time (min): 3.21 (CHIRALPAK IC 5 μm, 20 mm×250 (manufactured by Daicel Corporation); carbon dioxide:methanol=80:20).

Example 6-1(2)

4-[2-({2-[3-methyl-6-(methylcarbamoyl)-1H-indol-1-yl]propanoyl}amino)-4-{[4-(trifluoromethyl)-1H-1,2,3-triazol-yl]methyl}phenyl]butanoic acid (Second Peak)

SFC retention time (min): 4.80 (CHIRALPAK IC 5 μm, 20 mm×250 (manufactured by Daicel Corporation); carbon dioxide:methanol=80:20).

Examples 6-2 to 6-5(2)

The same procedure as in Reference Example 21 and Example 3 was carried out using the compound produced in Reference Example 18 and using the corresponding compound instead of trifluoroacetylene to obtain the compound of the present invention having the following physical property values. Furthermore, the resulting compound of the present invention was subjected to optical resolution by SFC to obtain an optically active substance of the compound of the present invention having the following physical property values.

Example 6-2

4-[2-({2-[3-methyl-6-(methylcarbamoyl)-1H-indol-1-yl]propanoyl}amino)-4-{[4-(2-methyl-2-propanyl)-1H-1,2,3-triazol-1-yl]methyl}phenyl]butanoic acid TLC: Rf 0.48 (ethyl acetate);

$^1$H-NMR (CDCl$_3$): δ 1.21, 1.56, 1.70-1.79, 2.03-2.12, 2.26, 2.36-2.48, 2.80, 5.39, 5.51, 7.06, 7.18, 7.32, 7.45, 7.54, 7.86, 8.12, 8.30, 9.68, 12.05.

Example 6-3(1)

4-[2-({2-[3-methyl-6-(methylcarbamoyl)-1H-indol-1-yl]propanoyl}amino)-4-{[4-(2-methyl-2-propanil)-1H-1,2,3-triazol-yl]methyl}phenyl]butanoic acid (First Peak)

SFC retention time (min): 4.20 (CHIRALPAK IC 5 μm, 20 mm×250 (manufactured by Daicel Corporation); carbon dioxide:methanol=70:30).

Example 6-3(2)

4-[2-({2-[3-methyl-6-(methylcarbamoyl)-1H-indol-1-yl]propanoyl}amino)-4-{[4-(2-methyl-2-propanyl)-1H-1,2,3-triazol-1-yl]methyl}phenyl]butanoic acid (second peak)

SFC retention time (min): 6.91 (CHIRALPAK IC 5 μm, 20 mm×250 (manufactured by Daicel Corporation); carbon dioxide:methanol=70:30).

Example 6-4

4-{4-[(4-isopropyl-1H-1,2,3-triazol-1-yl)methyl]-2-({2-[3-methyl-6-(methylcarbamoyl)-1H-indol-1-yl]propanoyl}amino)phenyl}butanoic acid

[Chem. 59]

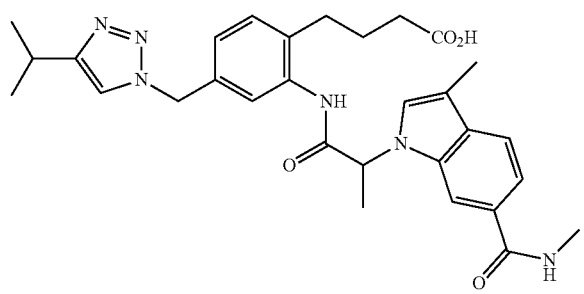

TLC: Rf 0.31 (ethyl acetate);

$^1$H-NMR (CDCl$_3$): δ 1.18, 1.46-1.60, 1.70-1.76, 2.02-2.12, 2.26, 2.36-2.47, 2.79, 2.92, 3.16, 5.40-5.49, 7.07, 7.18, 7.33, 7.45, 7.52, 7.84, 8.10, 8.28, 9.67, 12.05.

Example 6-5(1)

4-{4-[(4-isopropyl-1H-1,2,3-triazol-1-yl)methyl]-2-({2-[3-methyl-6-(methylcarbamoyl)-1H-indol-1-yl]propanoyl}amino)phenyl}butanoic acid (First Peak)

SFC retention time (min): 4.91 (CHIRALPAK IC 5 μm, 20 mm×250 (manufactured by Daicel Corporation); carbon dioxide:methanol=70:30).

Example 6-5(2)

4-{4-[(4-isopropyl-1H-1,2,3-triazol-1-yl)methyl]-2-({2-[3-methyl-6-(methylcarbamoyl)-1H-indol-1-yl]propanoyl}amino)phenyl}butanoic acid (Second Peak)

SFC retention time (min): 9.67 (CHIRALPAK IC 5 μm, 20 mm×250 (manufactured by Daicel Corporation); carbon dioxide:methanol=70:30).

Reference Example 22

The same procedure as in Reference Example 12 was carried out using 3-(trifluoromethyl)-1H-1,2,4-triazole instead of 4-methylpyrazole to obtain the compound of the present invention having the following physical property values (the compounds of Reference Example 22(1) and Reference Example 22(2)).

Reference Example 22(1)

Ethyl 4-(2-nitro-4-{[3-(trifluoromethyl)-1H-1,2,4-triazol-2-yl]methyl}phenyl)butanoate TLC: Rf 0.47 (hexane:ethyl acetate=1:1);

$^1$H-NMR (CDCl$_3$): δ 1.25, 1.93-2.07, 2.34-2.43, 2.89-2.99, 4.13, 5.43, 7.41-7.51, 7.89, 8.22.

Reference Example 22(2)

Ethyl 4-(2-nitro-4-{[5-(trifluoromethyl)-1H-1,2,4-triazol-1-yl]methyl}phenyl)butanoate TLC: Rf 0.76 (hexane:ethyl acetate=1:1);

$^1$H-NMR (CDCl$_3$): δ 1.26, 1.92-2.05, 2.33-2.42, 2.87-2.97, 4.13, 5.50, 7.36-7.47, 7.88, 8.03.

Reference Example 23

Ethyl 4-(2-amino-4-{[3-(trifluoromethyl)-1H-1,2,4-triazol-1-yl]methyl}phenyl)butanoate The same procedure as in Reference Example 13 was carried out using the compound produced in Reference Example 22(1) to obtain the title compound having the following physical property values.

TLC: Rf 0.63 (hexane:ethyl acetate=1:2);

$^1$H-NMR (CDCl$_3$): δ 1.26, 1.82-1.94, 2.36-2.44, 2.47-2.57, 4.04, 4.16, 5.25, 6.57-6.65, 7.03, 8.05.

Example 7

4-(2-[(2-{6-[(2-methoxyethyl)carbamoyl]-3-methyl-1H-indol-1-yl}propanoyl)amino]-4-{[3-(trifluoromethyl)-1H-1,2,4-triazol-1-yl]methyl}phenyl)butanoic acid

[Chem. 60]

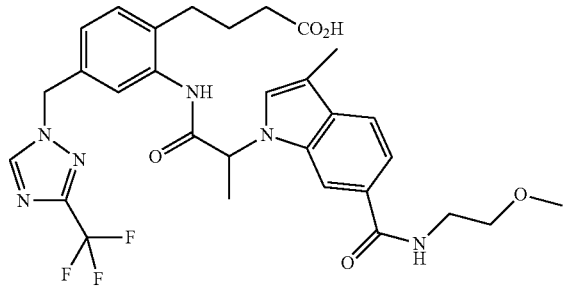

The same procedure as in Reference Example 14→Reference Example 15→Reference Example 16→Example 3 was carried out using the compound of Reference Example 23 instead of the compound of Reference Example 13 and using methoxyethylamine instead of N-ethylmethylamine to obtain the compound of the present invention having the following physical property values.

TLC: Rf 0.50 (dichloromethane:methanol=10:1);
$^1$H-NMR (DMSO-d$_6$): δ 1.56, 1.74, 2.02-2.11, 2.27, 2.32-2.67, 3.22-3.48, 5.43, 5.48, 7.11, 7.20, 7.38, 7.46, 7.53, 7.56, 8.13, 8.33-8.40, 8.94, 9.67-9.74, 12.04.

Example 7-1

The compound of Example 7 was subjected to optical resolution by SFC to obtain the compound of the present invention having the following physical property values.

Example 7-1(1)

4-(2-[(2-{6-[(2-methoxyethyl)carbamoyl]-3-methyl-1H-indol-1-yl}propanoyl)amino]-4-{[3-(trifluoromethyl)-1H-1,2,4-triazol-1-yl]methyl}phenyl)butanoic acid (First Peak)

SFC retention time (min): 2.69 (CHIRALPAK IA 5 μm, 20 mm×250 (manufactured by Daicel Corporation); carbon dioxide:methanol=75:25).

Example 7-1(2)

4-(2-[(2-{6-[(2-methoxyethyl)carbamoyl]-3-methyl-1H-indol-1-yl}propanoyl)amino]-4-{[3-(trifluoromethyl)-1H-1,2,4-triazol-1-yl]methyl}phenyl)butanoic acid (Second Peak)

SFC retention time (min): 5.31 (CHIRALPAK IA 5 μm, 20 mm×250 (manufactured by Daicel Corporation); carbon dioxide:methanol=75:25).

Example 7-2

4-[2-({2-[3-methyl-6-(methylcarbamoyl)-1H-indol-1-yl]propanoyl}amino)-4-{[3-(trifluoromethyl)-1H-1,2,4-triazol-1-yl]methyl}phenyl]butanoic acid

[Chem. 61]

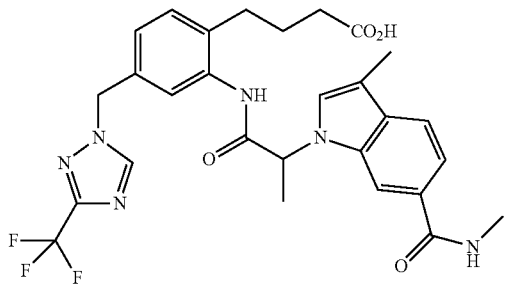

The same procedure as in Reference Example 14→Reference Example 15→Reference Example 16→Example 3 was carried out using the compound of Reference Example 23 and using methylamine instead of N-ethylmethylamine to obtain the compound of the present invention having the following physical property values.
HPLC retention time (min): 3.45;
MS (ESI, Pos.): 571.18 (M+H)$^+$;
$^1$H-NMR (DMSO-d$_6$): δ 1.56, 1.74, 2.07, 2.27, 2.31-2.52, 2.80, 5.41-5.54, 7.06-7.13, 7.20, 7.35-7.58, 8.11, 8.26-8.34, 8.95, 9.72, 12.04;

Example 7-3

The compound of Example 7-2 was subjected to optical resolution by SFC to obtain the compound of the present invention having the following physical property values.

Example 7-3(1)

4-[2-({2-[3-methyl-6-(methylcarbamoyl)-1H-indol-1-yl]propanoyl}amino)-4-{[3-(trifluoromethyl)-1H-1,2,4-triazol-1-yl]methyl}phenyl]butanoic acid (First Peak)

SFC retention time (min): 2.55 (CHIRALPAKIA 5 μm, 20 mm×250 (manufactured by Daicel Corporation); carbon dioxide:methanol=70:30).

Example 7-3(2)

4-[2-({2-[3-methyl-6-(methylcarbamoyl)-1H-indol-1-yl]propanoyl}amino)-4-{[3-(trifluoromethyl)-1H-1,2,4-triazol-1-yl]methyl}phenyl]butanoic acid (Second Peak)

$^1$H-NMR (DMSO-di): δ 1.56, 1.74, 2.07, 2.27, 2.31-2.52, 2.80, 5.41-5.54, 7.06-7.13, 7.20, 7.35-7.58, 8.11, 8.26-8.34, 8.95, 9.72, 12.04;
SFC retention time (min): 3.70 (CHIRALPAK OA 5 μm, 20 mm×250 (manufactured by Daicel Corporation); carbon dioxide:methanol=70:30).

Reference Example 24

Ethyl 4-(2-amino-4-{[5-(trifluoromethyl)-1H-1,2,4-triazol-1-yl]methyl}phenyl)butanoate The same procedure as in Example 13 was carried out using the compound of Reference Example 22(2) to obtain the title compound having the following physical properly values.
TLC: Rf 0.67 (hexane:ethyl acetate=1:1);
$^1$H-NMR (CDCl$_3$): δ 1.27, 1.81-1.94, 2.34-2.43, 2.46-2.55, 3.96, 4.15, 5.35, 6.54-6.64, 6.99, 7.98.

Example 7-4

4-[2-({2-[3-methyl-6-(methylcarbamoyl)-1H-indol-1-yl]propanoyl}amino)-4-{[5-(trifluoromethyl)-1H-1,2,4-triazol-1-yl]methyl}phenyl]butanoic acid The same procedure as in Reference Example 14→Reference Example 15→Reference Example 16→Example 3 was carried out using the compound of Reference Example 24 instead of the compound of Reference Example 13 and using methylamine instead of N-ethylmethylamine to obtain the compound of the present invention having the following physical property values.
TLC: Rf 0.52 (dichloromethane:methanol=10:1);
$^1$H-NMR (DMSO-d$_6$): δ 1.54, 1.73, 2.02-2.09, 2.27, 2.35-2.48, 2.80, 5.47, 5.51, 6.97, 7.18, 7.31, 7.45, 7.49-7.56, 8.09, 8.27, 8.29, 9.64, 12.05.

Example 7-5

The compound of Example 7-4 was subjected to optical resolution by SFC to obtain the compound of the present invention having the following physical property values.

Example 7-5(1)

4-[2-({2-[3-methyl-6-(methylcarbamoyl)-1H-indol-1-yl]propanoyl}amino)-4-{[5-(trifluoromethyl)-1H-1,2,4-triazol-1-yl]methyl}phenyl]butanoic acid (First Peak)

SFC retention time (min): 4.71 (CHIRALPAK IA 5 μm, 20 mm×250 (manufactured by Daicel Corporation); carbon dioxide:methanol=85:15).

Example 7-5(2)

4-[2-({2-[3-methyl-6-(methylcarbamoyl)-1H-indol-1-yl]propanoyl}amino)-4-{[5-(trifluoromethyl)-1H-1,2,4-triazol-1-yl]methyl}phenyl]butanoic acid (Second Peak)

SFC retention time (min): 6.87 (CHIRALPAK IA 5 μm, 20 mm×250 (manufactured by Daicel Corporation); carbon dioxide:methanol=85:15).

Reference Example 25

2-[5-(tert-butoxycarbonyl)-3-methyl-1H-indol-1-yl]propanoic acid

The same procedure as in Reference Example 1→Reference Example 2→Reference Example 3 was carried out using 3-methyl-1H-indole-5-carboxylic acid (CAS NO., 588688-44-2) instead of 3-methylindole-6-carboxylic acid to obtain the title compound having the following physical property values.

TLC: Rf 0.21 (dichloromethane:methanol=9:1);
$^1$H-NMR (CDCl$_3$): δ 1.62, 1.84, 2.35, 5.14, 7.05, 7.23, 7.87, 8.27.

Reference Example 26

1-(1-{2-(4-ethoxy-4-oxobutyl)-5-[(4-methyl-1H-pyrazol-1-yl)methyl]anilino}-1-oxopropan-2-yl)-3-methyl-1H-indole-5-carboxylic acid The same procedure as in Reference Example 14→Reference Example 15 was carried out using the compound of Reference Example 25 instead of the compound of Reference Example 11 to obtain the title compound having the following physical property values.

TLC: Rf 0.70 (ethyl acetate);
$^1$H-NMR (CDCl$_3$): δ 1.30, 1.47-1.60, 1.90, 2.03, 2.19, 2.20-2.31, 2.41, 4.18, 5.17, 5.43, 6.86, 7.02, 7.14, 7.30-7.34, 7.48, 7.97, 8.04, 8.44.

Example 8

4-{2-[(2-{5-[ethyl(methyl)carbamoyl]-3-methyl-1H-indol-1-yl}propanoyl)amino]-4-[(4-methyl-1H-pyrazol-1-yl)methyl]phenyl}butanoic acid

[Chem. 62]

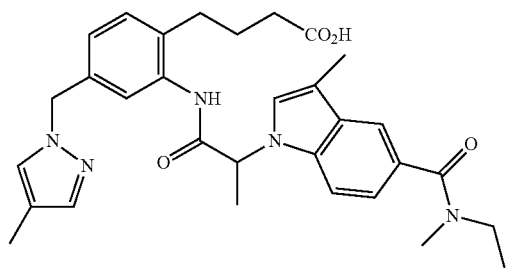

The same procedure as in Reference Reference Example 16→Example 3 was carried out using the compound of Reference Example 26 instead of the compound of Reference Example 15 to obtain the compound of the present invention having the following physical property values.

TLC: Rf 0.43 (dichloromethane:methanol=9:1);
$^1$H-NMR (CDCl$_3$): δ 1.06-1.44, 1.54-1.82, 1.87, 1.96, 2.04, 2.37, 2.96-3.17, 3.30-3.44, 3.55-3.72, 5.16, 5.19, 6.84, 6.96, 7.10-7.19, 7.20-7.27, 7.29-7.38, 7.71, 7.99.

Example 8-1

The compound of Example 8 was subjected to optical resolution by SFC to obtain the compound of the present invention having the following physical property values.

Example 8-1(1)

4-{2-[(2-{5-[ethyl(methyl)carbamoyl]-3-methyl-1H-indol-1-yl}propanoyl)amino]-4-[(4-methyl-1H-pyrazol-1-yl)methyl]phenyl}butanoic acid (First Peak)

SFC retention time (min): 5.12 (CHIRALPAK IA 5 μm, 20 mm×250 (manufactured by Daicel Corporation); carbon dioxide:methanol=70:30).

Example 8-1(2)

4-{2-[(2-{5-[ethyl(methyl)carbamoyl]-3-methyl-1H-indol-1-yl}propanoyl)amino]-4-[(4-methyl-1H-pyrazol-1-yl)methyl]phenyl}butanoic acid (Second Peak)

SFC retention time (min): 6.38 (CHIRALPAK IA 5 μm, 20 mm×250 (manufactured by Daicel Corporation); carbon dioxide:methanol=70:30).

Examples 8-2 to 8-23

The same procedure as in Reference Example 16→Example 3 was carried out using the compound of Reference Example 26 instead of the compound of Reference Example 15 and using the corresponding amine compound instead of N-ethylmethylamine to obtain the compound of the present invention having the following physical property values. The compound of the present invention was subjected to optical resolution by SFC to obtain an optically active substance of the compound of the present invention having the following physical property values.

Example 8-2

4-{2-({2-[3-methyl-5-(methylcarbamoyl)-1H-indol-1-yl]propanoyl}amino)-4-[(4-methyl-1H-pyrazol-1-yl)methyl]phenyl}butanoic acid

[Chem. 63]

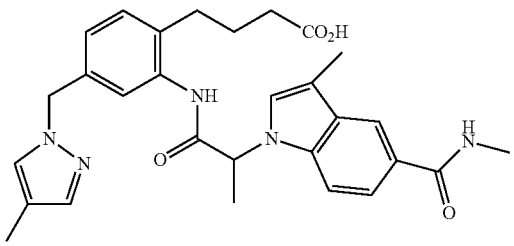

TLC: Rf 0.60 (ethyl acetate:methanol=4:1);
$^1$H-NMR (DMSO-d$_6$): δ 1.49-1.63, 1.73, 1.96, 2.02-2.13, 2.30, 2.36-2.49, 2.79, 5.12, 5.43, 6.95, 7.08-7.21, 7.38, 7.47, 7.54, 7.67, 8.06, 8.29, 9.72, 12.07.

Example 8-3(1)

4-{2-({2-[3-methyl-5-(methylcarbamoyl)-1H-indol-1-yl]propanoyl}amino)-4-[(4-methyl-1H-pyrazol-1-yl)methyl]phenyl}butanoic acid (First Peak)

SFC retention time (min): 3.93 (CHIRALPAK IA 5 μm, 20 mm×250 (manufactured by Daicel Corporation); carbon dioxide:methanol:THF=70:15:15).

Example 8-3(2)

4-{2-({2-[3-methyl-5-(methylcarbamoyl)-1H-indol-1-yl]propanoyl}amino)-4-[(4-methyl-1H-pyrazol-1-yl)methyl]phenyl}butanoic acid (Second Peak)

SFC retention time (min); 5.59 (CHIRALPAK IA 5 μm, 20 mm×250 (manufactured by Daicel Corporation); carbon dioxide:methanol:THF=70:15:15).

Example 8-4

4-{2-({2-[5-(ethylcarbamoyl)-3-methyl-1H-indol-1-yl]propanoyl}amino)-4-[(4-methyl-1H-pyrazol-1-yl)methyl]phenyl}butanoic acid TLC: Rf 0.48 (dichloromethane:methanol=9:1);
$^1$H-NMR (DMSO-d$_6$): δ 1.12, 1.58, 1.72, 1.95, 2.04, 2.30, 2.42-2.54, 3.20-3.44, 5.10, 5.63, 6.89-7.10, 7.18, 7.35-7.44, 7.45, 7.59-7.69, 8.06, 8.32, 10.58.

Example 8-5(1)

4-{2-({2-[5-(ethylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 5.72 (CHIRALPAK IA 5 μm, 20 mm×250 (manufactured by Daicel Corporation); carbon dioxide:methanol=70:30).

Example 8-5(2)

4-{2-({2-[5-(ethylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 7.78 (CHIRALPAK IA 5 μm, 20 mm×250 (manufactured by Daicel Corporation); carbon dioxide:methanol=70:30).

Example 8-6

4-{2-({2-[3-methyl-5-(propylcarbamoyl)-1H-indol-1-yl]propanoyl}amino)-4-[(4-methyl-1H-pyrazol-1-yl)methyl]phenyl}butanoic acid TLC: Rf 0.48 (dichloromethane:methanol=9:1);
$^1$H-NMR (DMSO-d$_6$): δ 0.87, 1.44-1.64, 1.74, 1.94, 2.06, 2.25, 2.39-2.54, 3.16-3.49, 5.12, 5.50, 6.92, 7.11, 7.19, 7.31, 7.39, 7.46, 7.59, 7.67, 8.08, 8.25-8.38, 10.17.

Example 8-7(1)

4-{2-({2-[3-methyl-5-(propylcarbamoyl)-1H-indol-1-yl]propanoyl}amino)-4-[(4-methyl-1H-pyrazol-1-yl)methyl]phenyl}butanoic acid (First Peak)

SFC retention time (min): 5.56 (CHIRALPAK IC 5 μm, 20 mm×250 (manufactured by Daicel Corporation); carbon dioxide:methanol=70:30).

Example 8-7(2)

4-{2-({2-[3-methyl-5-(propylcarbamoyl)-1H-indol-1-yl]propanoyl}amino)-4-[(4-methyl-1H-pyrazol-1-yl)methyl]phenyl}butanoic acid (Second Peak)

SFC retention time (min): 7.37 (CHIRALPAK IC 5 μm, 20 mm×250 (manufactured by Daicel Corporation); carbon dioxide:methanol=70:30).

Example 8-8

4-{2-({2-[5-(isopropylcarbamoyl)-3-methyl-1H-indol-1-yl]propanoyl}amino)-4-[(4-methyl-1H-pyrazol-1-yl)methyl]phenyl}butanoic acid

[Chem. 64]

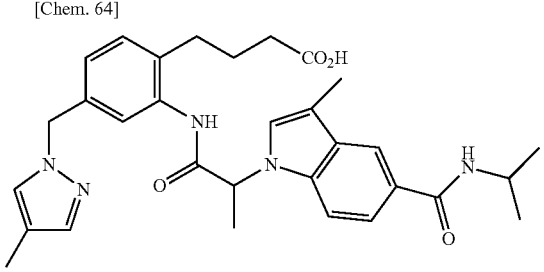

TLC: Rf 0.48 (dichloromethane:methanol=9:1);
$^1$H-NMR (DMSO-d$_6$): δ 1.18, 1.58, 1.73, 1.96, 2.08, 2.31, 2.36-2.60, 4.05-4.22, 5.13, 5.40, 6.97, 7.13, 7.16-7.22, 7.37, 7.46-7.55, 7.69, 8.04, 8.09, 9.64, 12.09.

Example 8-9(1)

4-{2-({2-[5-(isopropylcarbamoyl)-3-methyl-1H-indol-1-yl]propanoyl}amino)-4-[(4-methyl-1H-pyrazol-1-yl)methyl]phenyl}butanoic acid (First Peak)

SEC retention time (min): 5.17 (CHIRALPAK IC 5 μm, 20 mm×250 (manufactured by Daicel Corporation); carbon dioxide:methanol=70:30).

Example 8-9(2)

4-{2-({2-[5-(isopropylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 7.12 (CHIRALPAK IC 5 μm, 20 mm×250 (manufactured by Daicel Corporation); carbon dioxide:methanol=70:30).

Example 8-10

4-{2-[(2-{5-[(cyclopropylmethyl)carbamoyl]-3-methyl-1H-indol-1-yl}propanoyl)amino]-4-[(4-methyl-1H-pyrazol-1-yl)methyl]phenyl}butanoic acid TLC: Rf 0.48 (dichloromethane:methanol=9:1);
$^1$H-NMR (DMSO-d$_6$): δ 0.19-0.32, 0.36-0.48, 1.05, 1.57, 1.72, 1.96, 2.07, 2.31, 2.37-2.57, 3.16, 5.11, 5.45, 6.94, 7.08, 7.18-7.26, 7.39, 7.47, 7.56, 7.68, 8.10, 8.40, 9.88.

Example 8-11(1)

4-{2-[(2-{5-[(cyclopropylmethyl)carbamoyl]-3-methyl-1H-indol-1-yl}propanoyl)amino]-4-[(4-methyl-1H-pyrazol-1-yl)methyl]phenyl}butanoic acid (First Peak)

SFC retention time (min): 7.03 (CHIRALPAK IA 5 μm, 20 mm×250 (manufactured by Daicel Corporation); carbon dioxide:methanol=70:30).

Example 8-11(2)

4-{2-[(2-{5-[(cyclopropylmethyl)carbamoyl]-3-methyl-1H-indol-1-yl}propanoyl)amino]-4-[(4-methyl-1H-pyrazol-1-yl)methyl]phenyl}butanoic acid (Second Peak)

SFC retention time (min): 8.95 (CHIRALPAK IA 5 μm, 20 mm×250 (manufactured by Daicel Corporation); carbon dioxide:methanol=70:30).

Example 8-12

4-{2-[(2-{5-[(2-methoxyethyl)carbamoyl]-3-methyl-1H-indol-1-yl}propanoyl)amino]-4-[(4-methyl-1H-pyrazol-1-yl)methyl]phenyl}butanoic acid

[Chem. 65]

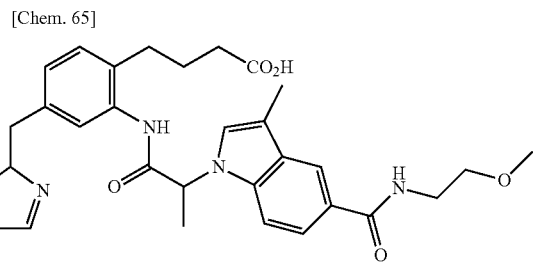

TLC: Rf 0.48 (dichloromethane:methanol=9:1);
$^1$H-NMR (DMSO-d$_6$): δ 1.57, 1.74, 1.96, 2.08, 2.30, 2.35-2.46, 2.47-2.61, 3.27, 3.32-3.53, 5.13, 5.40, 6.97, 7.13, 7.16-7.21, 7.38, 7.48, 7.53, 7.70, 8.11, 8.37, 9.65.

Example 8-13(1)

4-{2-[(2-{5-[(2-methoxyethyl)carbamoyl]-3-methyl-1H-indol-1-yl}propanoyl)amino]-4-[(4-methyl-1H-pyrazol-1-yl)methyl]phenyl}butanoic acid (First Peak)

SFC retention time (min): 5.24 (CHIRALPAK IC 5 μm, 20 mm×250 (manufactured by Daicel Corporation); carbon dioxide:methanol=70:30).

Example 8-13(2)

4-{2-[(2-{5-[(2-methoxyethyl)carbamoyl]-3-methyl-1H-indol-1-yl}propanoyl)amino]-4-[(4-methyl-1H-pyrazol-1-yl)methyl]phenyl}butanoic acid (Second Peak)

SFC retention time (min): 6.80 (CHIRALPAK IC 5 μm, 20 mm×250 (manufactured by Daicel Corporation); carbon dioxide:methanol=70:30).

Example 8-14

4-{2-({2-[5-(dimethylcarbamoyl)-3-methyl-1H-indol-1-yl]propanoyl}amino)-4-[(4-methyl-1H-pyrazol-1-yl)methyl]phenyl}butanoic acid TLC: Rf 0.48 (dichloromethane:methanol=9:1);
$^1$H-NMR (CDCl$_3$): δ 1.19-1.42, 1.57, 1.75, 1.89, 1.96, 2.04, 2.38, 3.07, 3.19, 5.15-5.24, 6.85, 6.97, 7.12-7.19, 7.22-7.28, 7.30-7.37, 7.75, 8.00.

Example 8-15(1)

4-{2-({2-[5-(dimethylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 5.38 (CHIRALPAK IA 5 μm, 20 mm×250 (manufactured by Daicel Corporation); carbon dioxide:methanol=70:30).

Example 8-15(2)

4-{2-({2-[5-(dimethylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 7.27 (CHIRALPAK IA 5 μm, 20 mm×250 (manufactured by Daicel Corporation); carbon dioxide:methanol=70:30).

Example 8-16

4-{4-[(4-methyl-1H-pyrazol-1-yl)methyl]-2-({2-[3-methyl-5-(1-pyrrolidinylcarbonyl)-1H-indol-1-yl]propanoyl}amino)phenyl}butanoic acid

[Chem. 66]

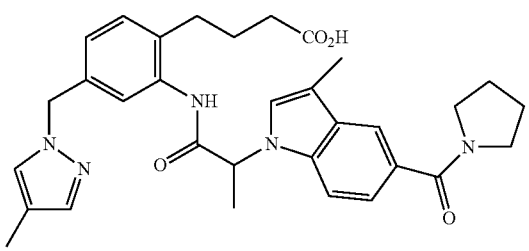

TLC: Rf 0.48 (dichloromethane:methanol=9:1);
$^1$H-NMR (DMSO-$d_6$): δ 1.53, 1.73, 1.73-1.90, 1.96, 2.05, 2.27, 2.40, 3.20-3.39, 3.47, 5.13, 5.40, 6.97, 7.13, 7.17-7.22, 7.30-7.39, 7.46, 7.55, 7.69, 9.65, 12.09.

Example 8-17(1)

4-{4-[(4-methyl-1H-pyrazol-1-yl)methyl]-2-({2-[3-methyl-5-(1-pyrrolidinylcarbonyl)-1H-indol-1-yl]propanoyl}amino)phenyl}butanoic acid (First Peak)

SFC retention time (min): 5.44 (CHIRALPAK IA 5 μm, 20 mm×250 (manufactured by Daicel Corporation); carbon dioxide:methanol=70:30).

Example 8-17(2)

4-{4-[(4-methyl-1H-pyrazol-1-yl)methyl]-2-({2-[3-methyl-5-(1-pyrrolidinylcarbonyl)-1H-indol-1-yl]propanoyl}amino)phenyl}butanoic acid (Second Peak)

SFC retention time (min): 7.08 (CHIRALPAK IA 5 μm, 20 mm×250 (manufactured by Daicel Corporation); carbon dioxide:methanol=70:30).

Example 8-18

4-{2-({2-[3-methyl-5-(1-piperidinylcarbonyl)-1H-indol-1-yl]propanoyl}amino)-4-[(4-methyl-1H-pyrazol-1-yl)methyl]phenyl}butanoic acid TLC: Rf 0.48 (dichloromethane:methanol=9:1);
$^1$H-NMR (DMSO-$d_6$): δ 1.41-1.67, 1.73, 1.96, 2.04, 2.26, 2.34-2.45, 2.47-2.62, 3.22-3.46, 5.13, 5.44, 6.95, 7.10-7.21, 7.24-7.28, 7.39, 7.47, 7.51, 7.56, 9.85.

Example 8-19(1)

4-{2-({2-[3-methyl-5-(1-piperidinylcarbonyl)-1H-indol-1-yl]propanoyl}amino)-4-[(4-methyl-1H-pyrazol-1-yl)methyl]phenyl}butanoic acid (First Peak)

SFC retention time (min): 8.34 (CHIRALPAK ID 5 μm, 20 mm×250 (manufactured by Daicel Corporation); carbon dioxide:methanol=70:30).

Example 8-19(2)

4-{2-({2-[3-methyl-5-(1-piperidinylcarbonyl)-1H-indol-1-yl]propanoyl}amino)-4-[(4-methyl-1H-pyrazol-1-yl)methyl]phenyl}butanoic acid (Second Peak)

SFC retention time (min): 15.3 (CHIRALPAK ID 5 μm, 20 mm×250 (manufactured by Daicel Corporation); carbon dioxide:methanol=70:30).

Example 8-20

4-{2-({2-[3-methyl-5-(4-morpholinylcarbonyl)-1H-indol-1-yl]propanoyl}amino)-4-[(4-methyl-1H-pyrazol-1-yl)methyl]phenyl}butanoic acid TLC: Rf 0.48 (dichloromethane:methanol=9:1);
$^1$H-NMR (DMSO-$d_6$): δ 1.54, 1.74, 1.96, 2.04, 2.27, 2.39, 3.46-3.65, 5.14, 5.40, 6.97, 7.13, 7.17, 7.24, 7.40, 7.48, 7.55, 7.58, 9.66, 12.07.

Example 8-2(1)

4-{2-({2-[3-methyl-5-(4-morpholinylcarbonyl)-1H-indol-1-yl]propanoyl}amino)-4-[(4-methyl-1H-pyrazol-1-yl)methyl]phenyl}butanoic acid (First Peak)

SFC retention time (min): 7.18 (CHIRALPAK ID 5 μm, 20 mm×250 (manufactured by Daicel Corporation); carbon dioxide:methanol=70:30).

Example 8-21(2)

4-{2-({2-[3-methyl-5-(4-morpholinylcarbonyl)-1H-indol-1-yl]propanoyl}amino)-4-[(4-methyl-1H-pyrazol-1-yl)methyl]phenyl}butanoic acid (Second Peak)

SFC retention time (min): 15.0 (CHIRALPAK ID 5 μm, 20 mm×250 (manufactured by Daicel Corporation); carbon dioxide:methanol=70:30).

Example 8-22

4-{2-({2-[5-(cyclopropylcarbamoyl)-3-methyl-1H-indol-1-yl]propanoyl}amino)-4-[(4-methyl-1H-pyrazol-1-yl)methyl]phenyl}butanoic acid TLC: Rf 0.48 (dichloromethane:methanol=9:1);
$^1$H-NMR (DMSO-$d_6$): δ 0.54-0.62, 0.63-0.72, 1.58, 1.72, 1.90, 1.95, 2.02, 2.23-2.32, 2.41-2.58, 2.79-2.93, 5.10, 5.58-5.73, 6.89, 7.10, 7.18, 7.40, 7.45, 7.64, 8.03, 8.27.

Example 8-23(1)

4-{2-({2-[5-(cyclopropylcarbamoyl)-3-methyl-1H-indol-1-yl]propanoyl}amino)-4-[(4-methyl-1H-pyrazol-1-yl)methyl]phenyl}butanoic acid (First Peak)

SFC retention time (min): 7.78 (CHIRALPAK IC 5 μm, 20 mm×250 (manufactured by Daicel Corporation); carbon dioxide:methanol=70:30).

Example 8-23(2)

4-{2-({2-[5-(cyclopropylcarbamoyl)-3-methyl-1H-indol-1-yl]propanoyl}amino)-4-[(4-methyl-1H-pyrazol-1-yl)methyl]phenyl}butanoic acid (Second Peak)

SFC retention time (min): 10.7 (CHIRALPAK IC 5 μm, 20 mm×250 (manufactured by Daicel Corporation); carbon dioxide:methanol=70:30).

Reference Example 27 tert-butyl 3-bromo-1-(1-methoxy-1-oxopropan-2-yl)-1H-indole-6-carboxylate

The same procedure as in Reference Example 9→Reference Example 10 was carried out using 3-bromo-1H-indole-6-carboxylic acid (CAS No., 219508-19-7) instead of 3-methylindole-6-carboxylic acid to obtain the title compound having the following physical property values.
TLC: Rf 0.23 (hexane:ethyl acetate=9:1);
$^1$H-NMR (CDCl$_3$): δ 1.63, 1.82, 3.73, 5.23, 7.43, 7.55, 7.82, 8.02.

Reference Example 28

2-[6-(tert-butoxycarbonyl)-3-cyclopropyl-1H-indol-1-yl]propanoic acid

To a solution of the compound (2.82 g) produced in Reference Example 27 in toluene (56 mL), potassium phosphate (4.7 g) and purified water (2.2 mL) were added, followed by ultrasonic degassing under argon atmosphere. Cyclopropylboric acid (1.9 g), and palladium acetate (166 mg), tricyclohexylphosphine (2 mL) were added thereto, and the resulting mixture was stirred at 80° C. for three hours. The reaction mixture was cooled to room temperature, and diluted with ethyl acetate. Then, a saturated ammonium chloride aqueous solution was added thereto. The resulting mixture was filtered through celite (trade name). The filtrate was extracted with ethyl acetate. The organic layer was washed with water and saturated brine, and dried over sodium sulfate, followed by concentration under reduced pressure. The resulting residue was purified by silica gel column chromatography (hexane:ethyl acetate=9:1) to obtain the title compound (1.86 g) having the following physical property values.
TLC: Rf 0.27 (hexane:ethyl acetate=9:1);
$^1$H-NMR (CDCl$_3$): δ 0.60-0.71, 0.83-0.95, 1.63, 1.77, 1.94, 3.71, 5.18, 7.09, 7.69, 7.76, 7.97.

Example 9

4-{2-({2-[3-cyclopropyl-6-(methylcarbamoyl)-1H-indol-1-yl]propanoyl}amino)-4-[(4-methyl-1H-pyrazol-1-yl)methyl]phenyl}butanoic acid

[Chem. 67]

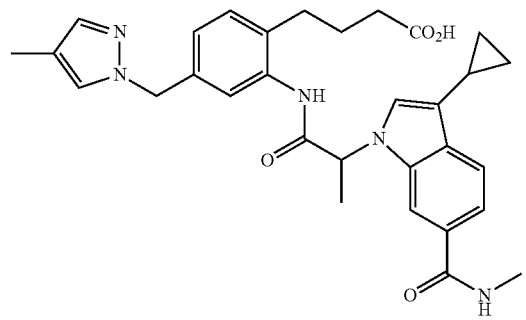

The same procedure as in Reference Example 14→Reference Example 15→Reference Example 16→Example 3 was carried out using the compound of Reference Example 28 instead of the compound of Reference Example 11 and using methylamine instead of N-ethylmethylamine to obtain the compound of the present invention having the following physical property values.
TLC: Rf 0.66 (dichloromethane:methanol=9:1);
$^1$H-NMR (DMSO-$d_6$): δ 0.57-0.70, 0.86, 1.54, 1.73, 1.90-1.99, 2.05, 2.17-2.31, 2.32-2.46, 2.72, 2.80, 5.13, 5.43, 6.96, 7.10-7.25, 7.36, 7.47-7.65, 8.09, 8.29, 9.64, 12.03.

Example 9-1

The compound of Example 9 was subjected to optical resolution by SFC to obtain the compound of the present invention having the following physical property values.

Example 9-1(1)

4-{2-({2-[3-cyclopropyl-6-(methylcarbamoyl)-1H-indol-1-yl]propanoyl}amino)-4-[(4-methyl-1H-pyrazol-1-yl)methyl]phenyl}butanoic acid (First Peak)

SFC retention time (min): 4.53 (CHIRALPAK ID 5 μm, 20 mm×250 (manufactured by Daicel Corporation); carbon dioxide:methanol=70:30).

Example 9-1(2)

4-{2-({2-[3-cyclopropyl-6-(methylcarbamoyl)-1H-indol-1-yl]propanoyl}amino)-4-[(4-methyl-1H-pyrazol-1-yl)methyl]phenyl}butanoic acid (Second Peak)

SFC retention time (min): 6.21 (CHIRALPAK ID 5 μm, 20 mm×250 (manufactured by Daicel Corporation); carbon dioxide:methanol=70:30).

Example 9-2

4-{2-[(2-{3-cyclopropyl-6-[(cyclopropylmethyl)carbamoyl]-1H-indol-1-yl}propanoyl)amino]-4-[(4-methyl-1H-pyrazol-1-yl)methyl]phenyl}butanoic acid The same procedure as in Reference Example 14→Reference Example 15→Reference Example 16→Example 3 was carried out using the compound of Reference Example 28 instead of the compound of Reference Example 11, and using cyclopropylmethylamine instead of N-ethylmethylamine to obtain the compound of the present invention having the following physical property values.

TLC: Rf 0.70 (dichloromethane:methanol=9:1);

$^1$H-NMR (DMSO-$d_6$): δ 0.21-0.26, 0.39-0.45, 0.58-0.69, 0.87, 1.05, 1.55, 1.73, 1.87-2.03, 2.06, 2.34-2.46, 3.16, 5.12, 5.45, 6.96, 7.10-7.25, 7.37, 7.48, 7.53-7.67, 8.11, 8.42, 9.66, 12.03.

Example 9-3

The compound of Example 9-2 was subjected to optical resolution by SFC to obtain the compound of the present invention having the following physical property values.

Example 9-3(1)

4-{2-[(2-{3-cyclopropyl-6-[(cyclopropylmethyl)carbamoyl]-1H-indol-1-yl}propanoyl)amino]-4-[(4-methyl-1H-pyrazol-1-yl)methyl]phenyl}butanoic acid (First Peak)

SFC retention time (min): 7.63 (CHIRALPAK IA 5 μm, 20 mm×250 (manufactured by Daicel Corporation); carbon dioxide:methanol=80:20).

Example 9-3(2)

4-{2-[(2-{3-cyclopropyl-6-[(cyclopropylmethyl)carbamoyl]-1H-indol-1-yl}propanoyl)amino]-4-[(4-methyl-1H-pyrazol-1-yl)methyl]phenyl}butanoic acid (second peak)

SFC retention time (min): 11.3 (CHIRALPAK IA 5 μm, 20 mm×250 (manufactured by Daicel Corporation); carbon dioxide:methanol=80:20).

Example 9-4

4-{2-[(2-{3-cyclopropyl-6-[(2-methoxyethyl)carbamoyl]-1H-indol-1-yl}propanoyl)amino]-4-[(4-methyl-1H-pyrazol-1-yl)methyl]phenyl}butanoic acid

[Chem. 68]

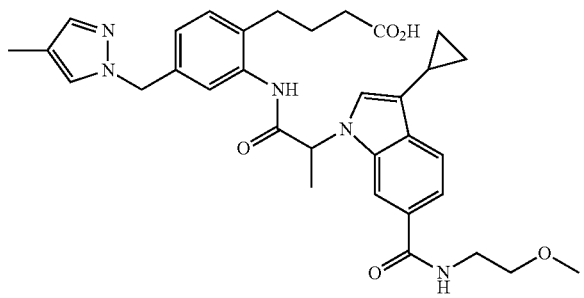

The same procedure as in Reference Example 14→Reference Example 15→Reference Example 16→Example 3 was carried out using the compound of Reference Example 28 instead of the compound of Reference Example II, and using methoxyethylamine instead of N-ethylmethylamine to obtain the compound of the present invention having the following physical property values.

TLC: Rf 0.68 (dichloromethane:methanol=9:1);

$^1$H-NMR (DMSO-$d_6$): δ 0.57-0.72, 0.87, 1.54, 1.73, 1.90-2.00, 2.05, 2.29-2.46, 3.35-3.54, 5.13, 5.44, 6.96, 7.10-7.27, 7.37, 8.11, 8.36, 9.65, 12.17.

Example 9-5

The compound of Example 9-4 was subjected to optical resolution as in Example 3-1 to obtain the compound of the present invention having the following physical property values.

Example 9-5(1)

4-{2-[(2-{3-cyclopropyl-6-[(2-methoxyethyl)carbamoyl]-1H-indol-1-yl}propanoyl)amino]-4-[(4-methyl-1H-pyrazol-1-yl)methyl]phenyl}butanoic acid (First Peak)

SFC retention time (min): 6.14 (CHIRALPAK IA 5 μm, 20 mm×250 (manufactured by Daicel Corporation); carbon dioxide:methanol=80:20).

Example 9-5(2)

4-{2-[(2-{3-cyclopropyl-6-[(2-methoxyethyl)carbamoyl]-1H-indol-1-yl}propanoyl)amino]-4-[(4-methyl-1H-pyrazol-1-yl)methyl]phenyl}butanoic acid (Second Peak)

SFC retention time (min): 9.64 (CHIRALPAK IA 5 μm, 20 mm×250 (manufactured by Daicel Corporation); carbon dioxide:methanol=80:20).

Example 10

4-{4-cyano-2-[(2-{6-[(2-methoxyethyl)carbamoyl]-1H-indol-1-yl}propanoyl)amino]phenyl}butanoic acid

[Chem. 69]

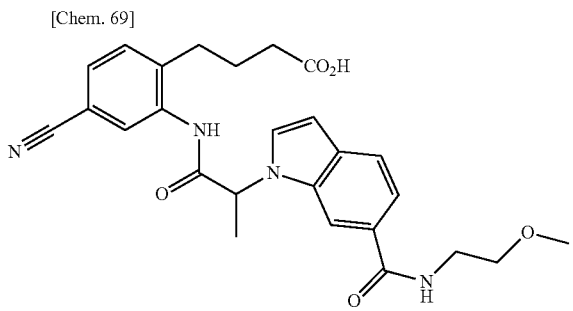

The same procedure as in Reference Example 9→Reference Example 10→Reference Example 11→Reference Example 14→Reference Example 15→Reference Example 16→Example 3 was carried out using indole-6-carboxylic acid (CAS No., 1670-81-1) instead of 3-methylindole-6-carboxylic acid, using ethyl 4-(2-amino-4-cyanophenyl)butanoate (WO 2016/111347, Reference Example 9) instead of the compound produced in Reference Example 13, and using methoxyethylamine instead of N-ethylmethylamine to obtain the compound of the present invention having the following physical property values.

TLC: Rf 0.15 (hexane:ethyl acetate=1:3);
$^1$H-NMR (DMSO-$d_6$): δ 1.54-1.71, 1.81, 2.12, 2.54-2.62, 3.24, 3.46, 5.57, 6.56, 7.39, 7.55-7.63, 7.70, 7.82, 8.16, 8.39, 9.95, 12.15.

Example 10-1

The compound of Example 10 was subjected to optical resolution by SFC to obtain the compound of the present invention having the following physical property values.

Example 10-1(1)

4-{4-cyano-2-[(2-{6-[(2-methoxyethyl)carbamoyl]-1H-indol-1-yl}propanoyl)amino]phenyl}butanoic acid (First Peak)

SFC retention time (min): 7.17 (CHIRALPAK ID 5 µm, 20 mm×250 (manufactured by Daicel Corporation); carbon dioxide:methanol=85:15).

Example 10-1(2)

4-{4-cyano-2-[(2-{6-[(2-methoxyethyl)carbamoyl]-1H-indol-1-yl}propanoyl)amino]phenyl}butanoic acid (Second Peak)

SFC retention time (min): 8.86 (CHIRALPAK ID 5 µm, 20 mm×250 (manufactured by Daicel Corporation); carbon dioxide:methanol=85:15).

Examples 10-2 to 3

The same procedure as in Reference Example 9→Reference Example 10→Reference Example 11→Reference Example 14→Reference Example 15→Reference Example 16→Example 3 was carried out using indole-6-carboxylic acid (CAS No., 1670-81-1) instead of 3-methylindole-6-carboxylic acid, using ethyl 4-(2-amino-4-cyanophenyl)butanoate (WO 2016/111347, Reference Example 9) instead of the compound produced in Reference Example 13, and using the corresponding amine compound instead of N-ethylmethylamine to obtain the compound of the present invention having the following physical property values.

Example 10-2

4-[4-cyano-2-({2-[6-(methylcarbamoyl)-1H-indol-1-yl]propanoyl}amino)phenyl]butanoic acid TLC: Rf 0.19 (hexane:ethyl acetate=1:3);
$^1$H-NMR (DMSO-$d_6$): δ 1.55-1.69, 1.81, 2.13, 2.50-2.61, 2.81, 5.58, 6.55, 7.43, 7.52-7.64, 7.70, 7.82, 8.14, 8.31, 9.94, 12.09.

Example 10-3

4-{4-cyano-2-[(2-{6-[(cyclopropylmethyl)carbamoyl]-1H-indol-1-yl}propanoyl)amino]phenyl}butanoic acid TLC: Rf 0.58 (hexane:ethyl acetate=1:3);
$^1$H-NMR (DMSO-$d_6$): δ 0.22, 0.42, 1.05, 1.56-1.69, 1.80, 2.15, 2.40-2.57, 3.16, 5.59, 6.54, 7.40, 7.54-7.61, 7.69, 7.81, 8.14, 8.41, 9.95, 12.06.

Reference Example 29

1-{1-[5-cyano-2-(4-ethoxy-4-oxobutyl)anilino]-1-oxopropan-2-yl}-3-methyl-1H-indole-6-carboxylic acid The same procedure as in Reference Reference Example 14→Reference Example 15 was carried out using ethyl 4-(2-amino-4-cyanophenyl)butanoate (WO 2016/111347, Reference Example 9) instead of the compound produced in Reference Example 13 to obtain the title compound having the following physical property values.

TLC: Rf 0.33 (hexane:ethyl acetate=1:1);
$^1$H-NMR (DMSO-$d_6$): δ 1.14, 1.60, 1.76, 2.11, 2.28, 2.37-2.59, 3.99, 5.54, 7.40, 7.53-7.55, 7.60, 7.65, 7.79, 8.21, 9.99, 12.58.

Examples 11 to 11-21(2)

The same procedure as in Reference Example 16→Example 3 was carried out using the compound of Reference Example 29 instead of the compound of Reference Example 15, and using the corresponding amine compound instead of N-ethylmethylamine to obtain the compound of the present invention having the following physical property values. Furthermore, the compound of the present invention was subjected to optical resolution by SFC to obtain an optically active substance of the compound of the present invention having the following physical property values.

Example 11

4-[4-cyano-2-({2-[6-ethylcarbamoyl)-3-methyl-1H-indol-1-yl]propanoyl}amino)phenyl]butanoic acid

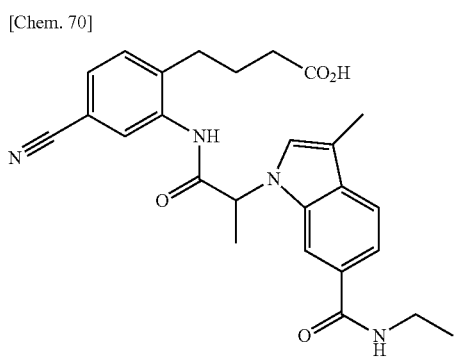 [SMILES: CCNC(=O)c1ccc2c(C)cn(C(C)C(=O)Nc3cc(C#N)ccc3CCCC(=O)O)c2c1]

[Chem. 70]

TLC: Rf 0.31 (hexane:ethyl acetate=1:3);
$^1$H-NMR (DMSO-$d_6$): δ 1.13, 1.60, 1.75, 2.11, 2.24-2.30, 2.45-2.61, 3.24-3.40, 5.51, 7.41, 7.47, 7.49-7.62, 7.82, 8.09, 8.33, 9.88, 12.11.

Example 11-1(1)

4-[4-cyano-2-({2-[6-ethylcarbamoyl)-3-methyl-1H-indol-1-yl]propanoyl}amino)phenyl]butanoic acid (First Peak)

SFC retention time (min): 5.41 (CHIRALPAK ID 5 μm, 20 mm×250 (manufactured by Daicel Corporation); carbon dioxide:methanol=85:15).

Example 11-1(2)

4-[4-cyano-2-({2-[6-ethylcarbamoyl)-3-methyl-1H-indol-1-yl]propanoyl}amino)phenyl]butanoic acid (Second Peak)

SFC retention time (min): 6.63 (CHIRALPAK ID 5 μm, 20 mm×250 (manufactured by Daicel Corporation); carbon dioxide:methanol=85:15).

Example 11-2

4-[4-cyano-2-({2-[3-methyl-6-(methylcarbamoyl)-1H-indol-1-yl]propanoyl}amino)phenyl]butanoic acid

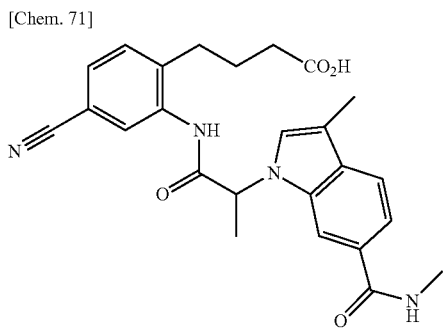

[Chem. 71]

TLC: Rf 0.56 (chloroform:methanol=9:1);
$^1$H-NMR (DMSO-$d_6$): δ 1.51-1.68, 1.75, 2.11, 2.27, 2.44-2.67, 2.80, 5.51, 7.37-7.63, 7.82, 8.10, 8.30, 9.87, 12.11.

Example 11-3(1)

4-[4-cyano-2-({2-[3-methyl-6-(methylcarbamoyl)-1H-indol-1-yl]propanoyl}amino)phenyl]butanoic acid (First Peak)

SFC retention time (min): 5.51 (CHIRALPAK ID 5 μm, 20 mm×250 (manufactured by Daicel Corporation); carbon dioxide:methanol=85:15).

Example 11-3(2)

4-[4-cyano-2-({2-[3-methyl-6-(methylcarbamoyl)-1H-indol-1-yl]propanoyl}amino)phenyl]butanoic acid (Second Peak)

SFC retention time (min): 6.93 (CHIRALPAK ID 5 μm, 20 mm×250 (manufactured by Daicel Corporation); carbon dioxide:methanol=85:15).

Example 11-4

4-{4-cyano-2-[2-{6-[(cyclopropylmethyl)carbamoyl]-3-methyl-1H-indol-1-yl}propanoyl)amino]phenyl}butanoic acid TLC: Rf 0.52 (hexane:ethyl acetate=1:3);
$^1$H-NMR (DMSO-$d_6$): δ 0.18-0.29, 0.36-0.49, 1.05, 1.54-1.67, 1.75, 2.07-2.15, 2.24-2.30, 2.46-2.60, 3.13-3.20, 3.31-3.37, 5.52, 7.41, 7.47, 7.51-7.62, 7.81, 8.11, 8.42, 9.89, 12.11.

Example 11-5(1)

4-{4-cyano-2-[2-{6-[(cyclopropylmethyl)carbamoyl]-3-methyl-1H-indol-1-yl}propanoyl)amino]phenyl}butanoic acid (First Peak)

SFC retention time (min): 7.02 (CHIRALPAK ID 5 μm, 20 mm×250 (manufactured by Daicel Corporation); carbon dioxide:methanol=85:15).

Example 11-5(2)

4-{4-cyano-2-[2-{6-[(cyclopropylmethyl)carbamoyl]-3-methyl-1H-indol-1-yl}propanoyl)amino]phenyl}butanoic acid (Second Peak)

SFC retention time (min): 8.55 (CHIRALPAK ID 5 μm, 20 mm×250 (manufactured by Daicel Corporation); carbon dioxide:methanol=85:15).

Example 11-6

4-{4-cyano-2-[(2-{3-methyl-6-[(2-methyl-2-propanyl)carbamoyl]-1H-indol-1-yl}propanoyl)amino]phenyl}butanoic acid

[Chem. 72]

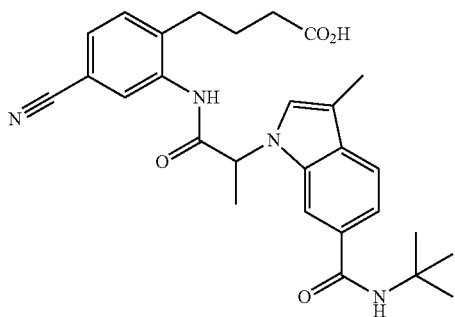

$^1$H-NMR (DMSO-d$_6$): δ 1.40, 1.55-1.70, 1.75, 2.06-2.20, 2.24-2.30, 2.41-2.46, 2.51-2.62, 5.52, 3.31-3.37, 5.52, 7.41, 7.44-7.61, 7.83, 8.03, 9.89, 12.11.

Example 11-7(1)

4-{4-cyano-2-[(2-{3-methyl-6-[(2-methyl-2-propanyl)carbamoyl]-1H-indol-1-yl}propanoyl)amino]phenyl}butanoic acid (first peak)

SFC retention time (min): 5.53 (CHIRALPAK ID 5 μm, 20 mm×250 (manufactured by Daicel Corporation); carbon dioxide:methanol=88:12).

Example 11-7(2)

4-{4-cyano-2-[(2-{3-methyl-6-[(2-methyl-2-propanyl)carbamoyl]-1H-indol-1-yl}propanoyl)amino]phenyl}butanoic acid (second peak)

SFC retention time (min): 6.84 (CHIRALPAK ID 5 μm, 20 mm×250 (manufactured by Daicel Corporation); carbon dioxide:methanol=88:12).

Example 11-8

4-[2-({2-[6-(benzylcarbamoyl)-3-methyl-1H-indol-1-yl]propanoyl}amino)-4-cyanophenyl]butanoic acid

[Chem. 73]

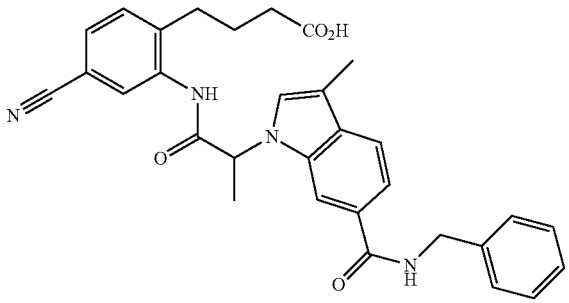

TLC: Rf 0.50 (dichloromethane:methanol=9:1);
$^1$H-NMR (DMSO-di): δ 1.16, 1.75, 2.09, 2.28, 2.40-2.60, 4.51, 5.53, 7.22-7.26, 7.27-7.35, 7.41, 7.49, 7.54, 7.57-7.66, 7.82, 8.16, 8.91, 9.89, 12.10.

Example 11-9(1)

4-[2-({2-[6-(benzylcarbamoyl)-3-methyl-1H-indol-1-yl]propanoyl}amino)-4-cyanophenyl]butanoic acid (First Peak)

SFC retention time (min): 6.41 (CHIRALPAK ID 5 μm, 20 mm×250 (manufactured by Daicel Corporation); carbon dioxide:methanol=80:20).

Example 11-9(2)

4-[2-({2-[6-(benzylcarbamoyl)-3-methyl-1H-indol-1-yl]propanoyl}amino)-4-cyanophenyl]butanoic acid (Second Peak)

SFC retention time (min): 8.56 (CHIRALPAK ID 5 μm, 20 mm×250 (manufactured by Daicel Corporation); carbon dioxide:methanol=80:20).

Example 11-10

4-[4-cyano-2-({2-[6-(cyclopentylcarbamoyl)-3-methyl-1H-indol-1-yl]propanoyl}amino)phenyl]butanoic acid

[Chem. 74]

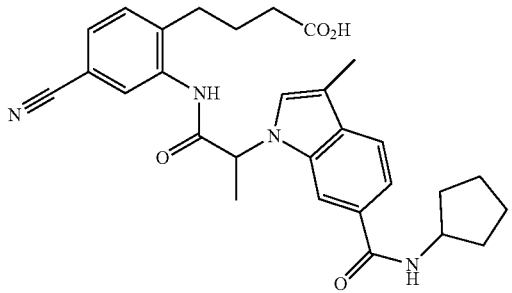

TLC: Rf 0.44 (dichloromethane:methanol=9:1);
$^{1}$H-NMR (DMSO-$d_6$): δ 1.48-1.72, 1.75, 1.79-1.98, 2.11, 2.27, 2.39-2.46, 2.53-2.61, 4.25, 5.54, 7.41, 7.48, 7.52, 7.55-7.61, 7.84, 8.09, 8.16, 9.97, 12.04.

Example 11-11(1)

4-[4-cyano-2-({2-[6-(cyclopentylcarbamoyl)-3-methyl-1H-indol-1-yl]propanoyl}amino)phenyl]butanoic acid (First Peak)

SFC retention time (min): 8.10 (CHIRALPAK ID 5 μm, 20 mm×250 (manufactured by Daicel Corporation); carbon dioxide:methanol=85:15).

Example 11-11(2)

4-[4-cyano-2-({2-[6-(cyclopentylcarbamoyl)-3-methyl-1H-indol-1-yl]propanoyl}amino)phenyl]butanoic acid (Second Peak)

SFC retention time (min): 10.4 (CHIRALPAK ID 5 μm, 20 mm×250 (manufactured by Daicel Corporation); carbon dioxide:methanol=85:15).

Example 11-12

4-[4-cyano-2-({2-[6-(cyclohexylcarbamoyl)-3-methyl-1H-indol-1-yl]propanoyl}amino)phenyl]butanoic acid TLC: Rf 0.44 (dichloromethane:methanol=9:1);
$^{1}$H-NMR (DMSO-$d_6$): δ 1.03-1.20, 1.22-1.40, 1.50-1.67, 1.67-1.80, 1.81-1.90, 2.10, 2.27, 2.39-2.60, 3.70-3.86, 5.51, 7.41, 7.48, 7.52, 7.54-7.62, 9.89, 12.07.

Example 11-13(1)

4-[4-cyano-2-({2-[6-(cyclohexylcarbamoyl)-3-methyl-1H-indol-1-yl]propanoyl}amino)phenyl]butanoic acid (First Peak)

SFC retention time (min): 4.08 (CHIRALPAK IA 5 μm, 20 mm×250 (manufactured by Daicel Corporation); carbon dioxide:methanol=80:20).

Example 11-13(2)

4-[4-cyano-2-({2-[6-(cyclohexylcarbamoyl)-3-methyl-1H-indol-1-yl]propanoyl}amino)phenyl]butanoic acid (Second Peak)

SFC retention time (min): 5.57 (CHIRALPAK IA 5 μm, 20 mm×250 (manufactured by Daicel Corporation); carbon dioxide:methanol=80:20).

Example 11-14

4-{4-cyano-2-[(2-{6-[(2-methoxyethyl)carbamoyl]-3-methyl-1H-indol-1-yl}propanoyl)amino]phenyl}butanoic acid

[Chem. 75]

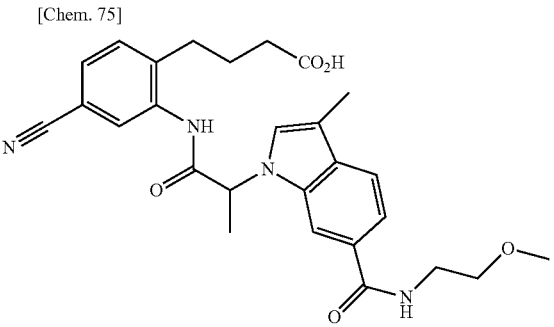

TLC: Rf 0.47 (chloroform:methanol=19:1);
$^{1}$H-NMR(CD$_3$OD): δ 1.49-1.64, 1.86, 2.13, 2.34, 2.39-2.49, 3.38, 3.58, 5.54, 7.36, 7.42-7.48, 7.51-7.62, 7.97, 8.09.

Example 11-15(1)

4-{4-cyano-2-[(2-{6-[(2-methoxyethyl)carbamoyl]-3-methyl-1H-indol-1-yl}propanoyl)amino]phenyl}butanoic acid (First Peak)

SFC retention time (min): 7.45 (CHIRALPAK ID 5 μm, 20 mm×250 (manufactured by Daicel Corporation); carbon dioxide:methanol=85:15).

Example 11-15(2)

4-{4-cyano-2-[(2-{6-[(2-methoxyethyl)carbamoyl]-3-methyl-1H-indol-1-yl}propanoyl)amino]phenyl}butanoic acid (Second Peak)

SFC retention time (min): 9.05 (CHIRALPAK ID 5 μm, 20 mm×250 (manufactured by Daicel Corporation); carbon dioxide:methanol=85:15).

Example 11-16

4-(4-cyano-2-{[(2-(6-{[(2-cyclopentyloxy)ethyl]carbamoyl}-3-methyl-1H-indol-1-yl)propanoyl]amino}phenyl)butanoic acid TLC: Rf 0.41 (dichloromethane:methanol=9:1);
$^{1}$H-NMR (DMSO-$d_6$): δ 1.38-1.48, 1.49-1.67, 1.77, 2.08, 2.27, 2.41-2.60, 3.34-3.51, 3.84-3.92, 5.51, 7.41, 7.45-7.52, 7.52-7.57, 7.59, 7.81, 8.11, 8.34, 9.86, 12.11.

Example 11-17(1)

4-(4-cyano-2-{[(2-(6-{[(2-cyclopentyloxy)ethyl]carbamoyl}-3-methyl-1H-indol-1-yl)propanoyl]amino}phenyl)butanoic acid (First Peak)

SFC retention time (min): 10.8 (CHIRALPAK ID 5 μm, 20 mm×250 (manufactured by Daicel Corporation); carbon dioxide:methanol=85:15).

Example 11-17(2)

4-(4-cyano-2-{[(2-(6-{[(2-cyclopentyloxy)ethyl]carbamoyl}-3-methyl-1H-indol-1-yl)propanoyl]amino}phenyl)butanoic acid (Second Peak)

SFC retention time (min): 13.4 (CHIRALPAK ID 5 μm, 20 mm×250 (manufactured by Daicel Corporation); carbon dioxide:methanol=85:15).

Example 11-18

4-{4-cyano-2-[(2-{3-methyl-6-[2-phenoxyethyl)carbamoyl]-1H-indol-1-yl}propanoyl)amino]phenyl}butanoic acid TLC: Rf 0.52 (hexane:ethyl acetate=1:1);
$^1$H-NMR (DMSO-$d_6$): δ 1.51-1.67, 1.75, 2.10, 2.27, 2.46-2.59, 3.66, 4.12, 5.52, 6.86-7.00, 7.21-7.32, 7.40, 7.49, 7.51-7.64, 7.82, 8.14, 8.58, 9.88, 12.11.

Example 11-19(1)

4-{4-cyano-2-[(2-{3-methyl-6-[2-phenoxyethyl)carbamoyl]-1H-indol-1-yl}propanoyl)amino]phenyl}butanoic acid (First Peak)

SFC retention time (min): 6.88 (CHIRALPAK ID 5 μm, 20 mm×250 (manufactured by Daicel Corporation); carbon dioxide:methanol=80:20).

Example 11-19(2)

4-{4-cyano-2-[(2-{3-methyl-6-[2-phenoxyethyl)carbamoyl]-1H-indol-1-yl}propanoyl)amino]phenyl}butanoic acid (Second Peak)

SFC retention time (min): 8.57 (CHIRALPAK ID 5 μm, 20 mm×250 (manufactured by Daicel Corporation); carbon dioxide:methanol=80:20).

Example 11-20

4-[2-({2-[6-(1-azetidinylcarbonyl)-3-methyl-1H-indol-1-yl]propanoyl}amino)-4-cyanophenyl]butanoic acid TLC: Rf 0.16 (ethyl acetate);
$^1$H-NMR (DMSO-$d_6$): δ 1.53-1.66, 1.72-1.79, 2.06-2.14, 2.17-2.30, 2.52-2.59, 3.93-4.13, 4.18-4.41, 5.51, 7.29, 7.41, 7.48, 7.52, 7.59, 7.80, 7.84, 9.90, 12.13.

Example 11-21(1)

4-[2-({2-[6-(1-azetidinylcarbonyl)-3-methyl-1H-indol-1-yl]propanoyl}amino)-4-cyanophenyl]butanoic acid (First Peak)

SFC retention time (min): 6.78 (CHIRALPAK ID 5 μm, 20 mm×250 (manufactured by Daicel Corporation); carbon dioxide:methanol=80:20).

Example 11-21(2)

4-[2-({2-[6-(1-azetidinylcarbonyl)-3-methyl-1H-indol-1-yl]propanoyl}amino)-4-cyanophenyl]butanoic acid (Second Peak)

SFC retention time (min): 8.87 (CHIRALPAK ID 5 μm, 20 mm×250 (manufactured by Daicel Corporation); carbon dioxide:methanol=80:20).

Examples 11-22 to 11-27(2)

The same procedure as in Reference Example 14→Reference Example 15→Reference Example 16→Example 3 was carried out using the compound of Reference Example 28 instead of the compound of Reference Example 11, using ethyl 4-(2-amino-4-cyanophenyl)butanoate (WO2016/111347, Reference Example 9) instead of the compound of Reference Example 13, and using the corresponding amine compound instead of N-ethylmethylamine to obtain the compound of the present invention having the following physical property values. Furthermore, the resulting compound of the present invention was subjected to optical resolution by SFC to obtain an optically active substance having the following physical property values as the compound of the present invention.

Example 11-22

4-[4-cyano-2-({2-[3-cyclopropyl-6-(methylcarbamoyl)-1H-indol-1-yl]propanoyl}amino)phenyl]butanoic acid

[Chem. 76]

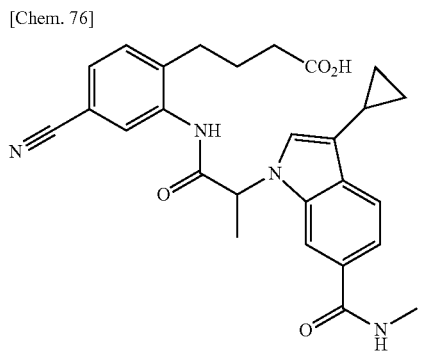

TLC: Rf 0.64 (ethyl acetate:methanol=9:1);
$^1$H-NMR (DMSO-$d_6$): δ 0.55-0.71, 0.80-0.93, 1.51-1.66, 1.75, 1.87-2.01, 2.10, 2.52-2.61, 2.80, 5.52, 7.35-7.45, 7.49-7.67, 7.80, 8.17, 8.34, 9.97, 12.10.

Example 11-23(1)

4-[4-cyano-2-({2-[3-cyclopropyl-6-(methylcarbamoyl)-1H-indol-1-yl]propanoyl}amino)phenyl]butanoic acid (First Peak)

SFC retention time (min): 9.44 (CHIRALPAK IE 5 μm, 20 mm×250 (manufactured by Daicel Corporation); carbon dioxide:methanol=80:20).

Example 11-23(2)

4-[4-cyano-2-({2-[3-cyclopropyl-6-(methylcarbamoyl)-1H-indol-1-yl]propanoyl}amino)phenyl]butanoic acid (Second Peak)

SFC retention time (min): 11.4 (CHIRALPAK IE 5 μm, 20 mm×250 (manufactured by Daicel Corporation); carbon dioxide:methanol=80:20).

Example 11-24

4-{4-cyano-2-[(2-{3-cyclopropyl-6-[(2-methoxyethyl)carbamoyl]-1H-indol-1-yl}propanoyl)amino]phenyl}butanoic acid

[Chem. 77]

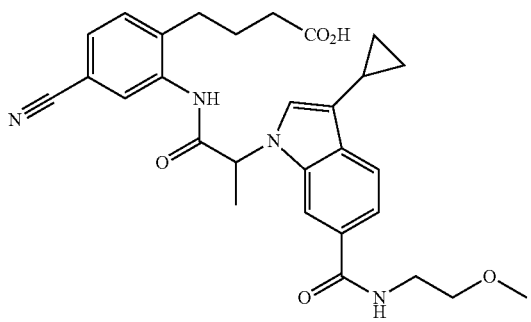

TLC: Rf 0.64 (ethyl acetate:methanol=9:1);
$^1$H-NMR (DMSO-$d_6$): δ 0.56-0.71, 0.79-0.94, 1.39-1.68, 1.75, 1.88-2.01, 2.11, 2.51-2.60, 3.25, 3.38-3.52, 5.49, 7.35-7.46, 7.52-7.67, 7.81, 8.10, 8.37, 9.86, 12.10.

Example 11-25(1)

4-{4-cyano-2-[(2-{3-cyclopropyl-6-[(2-methoxyethyl)carbamoyl]-1H-indol-1-yl}propanoyl)amino]phenyl}butanoic acid (First Peak)

SFC retention time (min): 6.79 (CHIRALPAK IA 5 μm, 20 mm×250 (manufactured by Daicel Corporation); carbon dioxide:methanol=85:15).

Example 11-25(2)

4-{4-cyano-2-[(2-{3-cyclopropyl-6-[(2-methoxyethyl)carbamoyl]-1H-indol-1-yl}propanoyl)amino]phenyl}butanoic acid (Second Peak)

SFC retention time (min): 8.09 (CHIRALPAK IA 5 μm, 20 mm×250 (manufactured by Daicel Corporation); carbon dioxide:methanol=85:15).

Example 11-26

TLC: Rf 0.81 (ethyl acetate:methanol=9:1)

4-{4-cyano-2-[(2-{3-cyclopropyl-6-[(2-methoxyethyl)carbamoyl]-1H-indol-1-yl}propanoyl)amino]phenyl}butanoic acid $^1$H-NMR (DMSO-$d_6$): δ 0.18-0.27, 0.37-0.47, 0.57-0.71, 0.80-0.94, 0.98-1.12, 1.53-1.67, 1.75, 1.88-2.02, 2.12, 2.45-2.67, 3.16, 5.50, 7.36-7.44, 7.54-7.67, 7.82, 8.10, 8.42, 9.88, 12.10.

Example 11-27(1)

4-{4-cyano-2-[(2-{3-cyclopropyl-6-[(cyclopropylmethyl)carbamoyl]-1H-indol-1-yl}propanoyl)amino]phenyl}butanoic acid (First Peak)

SFC retention time (min): 11.1 (CHIRALPAK IE 5 μm, 20 mm×250 (manufactured by Daicel Corporation); carbon dioxide:methanol=80:20).

Example 11-27(2)

4-{4-cyano-2-[(2-{3-cyclopropyl-6-[(cyclopropylmethyl)carbamoyl]-1H-indol-1-yl}propanoyl)amino]phenyl}butanoic acid (Second Peak)

SFC retention time (min): 14.0 (CHIRALPAK IE 5 μm, 20 mm×250 (manufactured by Daicel Corporation); carbon dioxide:methanol=80:20).

Example 11-28

4-{4-cyano-2-[(2-{3-methyl-5-[(2-phenoxyethyl)carbamoyl]-1H-indol-1-yl}propanoyl)amino]phenyl}butanoic acid The same procedure as in Reference Example 14→Reference Example 15→Reference Example 16→Example 3 was carried out using the compound of Reference Example 25 instead of the compound of Reference Example 11, using ethyl 4-(2-amino-4-cyanophenyl)butanoate (WO2016/111347, Reference Example 9) instead of the compound of Reference Example 13, and using 2-phenoxyethylamine instead of N-ethylmethylamine to obtain the compound of the present invention having the following physical property values.

TLC: Rf 0.41 (chloroform:methanol=9:1);
$^1$H-NMR (DMSO-$d_6$): δ 1.54-1.69, 1.76, 2.14, 2.30, 2.56, 3.64, 4.12, 5.47, 6.87-7.02, 7.22-7.32, 7.37-7.43, 7.49-7.62, 7.72, 7.81, 8.12, 8.57, 9.88, 12.16.

Examples 11-29 to 30(2)

The same procedure as in Reference Example 14→Reference Example 15→Reference Example 16→Example 3 was carried out using ethyl 4-(2-amino-4-fluorophenyl)butanoate (synthesized using 5-fluoro-2-iodonitrobenzene instead of 3-nitro-4-bromobenzaldehyde, by the method of Reference Example 7→Reference Example 9 in WO 2016/111347) instead of the compound of Reference Example 13, and using 2-methoxyethylamine instead of N-ethylmethylamine to obtain the compound of the present invention having the following physical property values. Furthermore, the resulting compound of the present invention was subjected to optical resolution by SFC to obtain an optically active substance having the following physical property values as the compound of the present invention.

Example 11-29

4-{4-fluoro-2-[(2-{6-[(2-methoxyethyl)carbamoyl]-3-methyl-1H-indol-1-yl}propanoyl)amino]phenyl}butanoic acid

[Chem. 78]

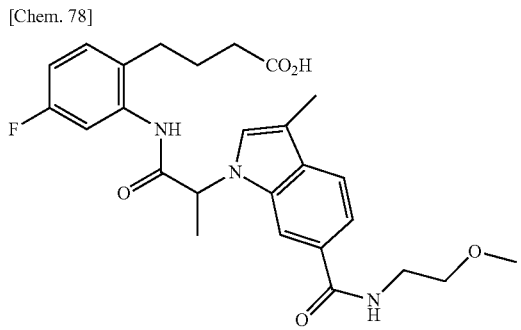

TLC: Rf 0.62 (chloroform:methanol=19:1)
$^1$H-NMR (CD$_3$OD): δ 1.46-1.58, 1.86, 2.10, 2.30-2.39, 3.37, 3.58, 5.53, 6.85, 7.15, 7.40-7.47, 7.50-7.62, 8.09.

Example 11-30(1)

4-{4-fluoro-2-[(2-{6-[(2-methoxyethyl)carbamoyl]-3-methyl-1H-indol-1-yl}propanoyl)amino]phenyl}butanoic acid (First Peak)

SFC retention time (min): 3.92 (CHIRALPAK ID 5 μm, 20 mm×250 (manufactured by Daicel Corporation); carbon dioxide:methanol=85:15).

Example 11-30(2)

4-{4-fluoro-2-[(2-{6-[(2-methoxyethyl)carbamoyl]-3-methyl-1H-indol-1-yl}propanoyl)amino]phenyl}butanoic acid (Second Peak)

SFC retention time (min): 5.23 (CHIRALPAK ID 5 μm, 20 mm×250 (manufactured by Daicel Corporation); carbon dioxide:methanol=85:15).

Reference Example 30

Ethyl 4-(2-{2-[3-methyl-6-(methylcarbamoyl)-1H-indol-1-yl]propanamido}-4-[(4-methyl-1H-pyrazol-1-yl)methyl]phenyl)butanoate The same procedure as in Reference Example 6 was carried out using the compound produced in Reference Example 13 instead of the compound produced in Reference Example 5 to obtain the title compound having the following physical property values.

$^1$H-NMR (CDCl$_3$): δ 1.26, 1.44, 1.90, 2.03, 2.08-2.22, 2.36, 3.01, 4.16, 5.13, 5.43, 6.31, 6.84, 6.97, 7.12, 7.30-7.36, 7.42, 7.57, 7.90, 7.94-8.04.

Example 12

4-{2-({2-[3-methyl-6-(methylcarbamoyl)-1H-indol-1-yl]propanoyl}amino)-4-[(4-methyl-1H-pyrazol-1-yl)methyl]phenyl}butanoic acid

[Chem. 79]

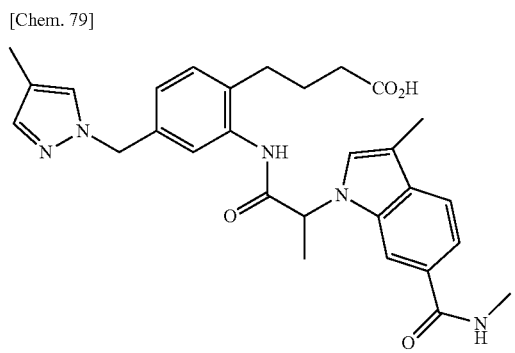

The same procedure as in Reference Example 3 was carried out using the compound produced in Reference Example 30 instead of the compound produced in Reference Example 16 to obtain the compound of the present invention having the following physical property values.

TLC: Rf 0.65 (ethyl acetate:methanol=4:1);
$^1$H-NMR (DMSO-d$_6$): δ 1.46-1.61, 1.73, 1.95, 2.00-2.08, 2.27, 2.31-2.45, 2.81, 5.13, 5.45, 6.96, 7.12, 7.17-7.22, 7.41-7.54, 8.10, 8.29, 9.66, 12.04.

Example 12-1

The compound of Example 12 was subjected to optical resolution by HPLC (CHIRALPAK ID, EtOH/MeOH/TFA=80/20/0.1) to obtain the compound of the present invention having the following physical property values.

Example 12-1(1)

4-{2-({2-[3-methyl-6-(methylcarbamoyl)-1H-indol-1-yl]propanoyl}amino)-4-[(4-methyl-1H-pyrazol-1-yl)methyl]phenyl}butanoic acid (First Peak)

TLC: Rf 0.63 (chloroform:methanol=9:1);
$^1$H-NMR (DMSO-d$_6$): δ 1.46-1.61, 1.73, 1.95, 2.00-2.08, 2.27, 2.31-2.45, 2.81, 5.13, 5.45, 6.96, 7.12, 7.17-7.22, 7.41-7.54, 8.10, 8.29, 9.66, 12.04.

Example 12-1(2)

4-{2-({2-[3-methyl-6-(methylcarbamoyl)-1H-indol-1-yl]propanoyl}amino)-4-[(4-methyl-1H-pyrazol-1-yl)methyl]phenyl}butanoic acid (Second Peak)

TLC: Rf 0.63 (chloroform:methanol=9:1);
$^1$H-NMR (DMSO-d$_6$): δ 1.46-1.61, 1.73, 1.95, 2.00-2.08, 2.27, 2.31-2.45, 2.81, 5.13, 5.45, 6.96, 7.12, 7.17-7.22, 7.41-7.54, 8.10, 8.29, 9.66, 12.04.

Reference Example 31

1-iodo-4-(methoxymethoxy)-2-nitrobenzene

Under a stream of nitrogen, to a solution of 4-iodo-3-nitrophenol (70.0 g) and N,N-diisopropylethylamine (68.2 g) in dichloromethane (370 mL), in the ice bath, chloromethyl methyl ether (31.8 g) was added dropwise. The resulting mixture was stirred at room temperature for 30 minutes. Water and ethyl acetate were added to the reaction mixture, followed by separation. The water layer was extracted with ethyl acetate, and the organic layer was washed with hydrochloric acid aqueous solution (0.5 mol/L), water, saturated sodium hydrogencarbonate aqueous solution, and saturated brine, dried over anhydrous sodium sulfate, and concentrated under reduced pressure to obtain the title compound (84.0 g) having the following physical property values.

TLC: Rf 0.46 (hexane:ethyl acetate=9:1);
$^1$H-NMR (CDCl$_3$): δ 3.47, 5.20, 6.98, 7.56, 7.87.

Reference Example 32

Ethyl 4-[4-(methoxymethoxy)-2-nitrophenyl]butanoate

Under a stream of nitrogen, to a solution of zinc powder (99.2 g) in N,N-dimethylacetamide (hereinafter, referred to as "DMA") (700 mL), iodine (26.0 g) was added, and the resulting mixture was stirred for 10 minutes. Ethyl 4-bromobutyrate (200 g) was added dropwise thereto, and the resulting mixture was stirred at 80° C. for two hours, and thereby a zinc reagent was prepared. Under a stream of nitrogen, to a solution of the compound (84.3 g) produced in Reference Example 31 in THF (400 mL), 2-dicyclohexylphosphino-2'6'-dimethoxybiphenyl (4.5 g) and palladium acetate (1.2 g) were added, and zinc reagent (318 mL) prepared was added drop wise under ice cooling, and the resulting product was stirred at room temperature for 30 minutes. An aqueous solution of saturated ammonium chloride and water were added to the reaction mixture, followed by extraction with ethyl acetate. The resulting organic layer was washed with water and saturated brine, dried over anhydrous sodium sulfate, and concentrated under reduced pressure. The resulting residue was purified by silica gel column chromatography to obtain the title compound (76 g) having the following physical property values.

TLC: Rf 0.29 (hexane:ethyl acetate=9:1);
$^1$H-NMR (CDCl$_3$): δ 1.26, 1.88-2.02, 2.37, 2.84, 3.48, 4.11, 5.19, 7.13-7.27, 7.58.

Reference Example 33

Ethyl 4-(4-hydroxy-2-nitrophenyl)butanoate

Under a stream of nitrogen, to a solution of the compound (21.8 g) produced in Reference Example 32 in ethanol (120 mL), 4 mol/L dioxane hydrochloride solution (120 mL) was added, and the resulting mixture was stirred at room temperature for one hour. To the reaction mixture, an aqueous solution of saturated ammonium chloride and water were added, followed by extraction with ethyl acetate. The reaction solution was concentrated under reduced pressure, and thereby the resulting residue was purified by silica gel column chromatography to obtain the title compound (17 g) having the following physical property values.

TLC: Rf 0.35 (hexane:ethyl acetate=3:1);
$^1$H-NMR (CDCl$_3$): δ 1.28, 1.88-2.02, 2.39, 2.84, 4.14, 6.01, 7.00, 7.17, 7.39.

Reference Example 34

Ethyl 4-(2-nitro-4-phenoxyphenyl)butanoate

Under a stream of nitrogen, to a solution of the compound (290 mg) produced in Reference Example 33 in dichloromethane (3 mL), triethylamine (0.797 mL), 4 Å molecular sieve (60 mg), phenylboronic acid (349 mg), and copper acetate (II) (208 mg) were added, and the resulting mixture was stirred at room temperature for 24 hours. Triethylamine (0.797 mL), 4 Å molecular sieve (300 mg), phenylboronic acid (349 mg), and copper acetate (II) (208 mg) were added, and the resulting mixture was stirred at room temperature for farther 48 hours. The reaction mixture was diluted with ethyl acetate, and then filtered through celite (trade name). The filtrate was washed with an aqueous solution of saturated ammonium chloride: 28% aqueous solution of ammonium=4:1 solution, water, and saturated brine, and dried over anhydrous sodium sulfate, followed by concentration under reduced pressure. The resulting residue was purified by silica gel column chromatography to obtain the title compound (119 mg) having the following physical property values.

TLC: Rf 0.73 (hexane:ethyl acetate=3:1);
$^1$H-NMR (CDCl$_3$): δ 1.27, 1.91-2.04, 2.39, 2.87, 4.14, 7.00-7.06, 7.12-7.32, 7.34-7.42, 7.48.

Example 13

4-[2-({2-[3-methyl-6-(methylcarbamoyl)-1H-indol-1-yl]propanoyl}amino)-4-phenoxyphenyl]butanoic acid

[Chem. 80]

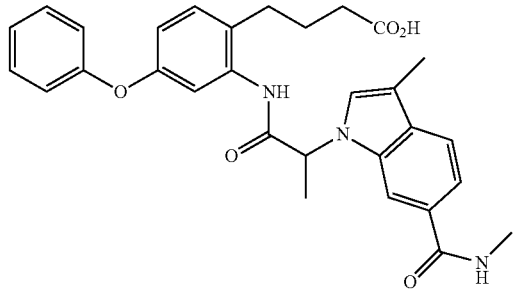

The same procedure as in Reference Example 13→Reference Example 6→Example 3 was carried out using the compound produced in Reference Example 34 instead of the compound produced in Reference Example 12 to obtain the compound of the present invention having the following physical property values.

TLC: Rf 0.63 (chloroform:methanol=9:1);
$^1$H-NMR (DMSO-d$_6$): δ 1.49-1.64, 1.73, 2.04-2.16, 2.26, 2.33-2.51, 2.79, 5.49, 6.78, 6.90-6.98, 7.03-7.20, 7.29-7.39, 7.41-7.57, 8.08, 8.27, 9.55, 12.08.

Reference Example 35

Ethyl 4-{2-nitro-4-[(1-propyl-1H-pyrazol-4-yl)oxy]phenyl}butanoate

Under a stream of nitrogen, to a solution of ethyl 4-(4-fluoro-2-nitrophenyl)butanoate (synthesized using 5-fluoro-2-iodonitrobenzene instead of 3-nitro-4-bromobenzaldehyde by the method of Reference Example 7 in WO 2016/111347) (300 mg) in DMF (3 mL), 1-propylpyrazol-4-ol (222 mg) and cesium carbonate (689 mg) were added, and the resulting mixture was stirred at 80° C. for three hours, and at 150° C. for 15 hours. Water was added to the reaction mixture, followed by extraction with ethyl acetate. The resulting organic layer was washed with water and saturated brine, dried over anhydrous sodium sulfate, followed by concentration under reduced pressure. The resulting residue was purified by silica gel column chromatography to obtain the title compound (35 mg) having the following physical property values.

TLC: Rf 0.38 (hexane:ethyl acetate=2:1);

$^1$H-NMR (CDCl$_3$): δ 0.95, 1.26, 1.82-2.04, 2.37, 2.86, 4.00-4.18, 7.12-7.38, 7.50.

Example 14

4-{2-({2-[3-methyl-6-(methylcarbamoyl)-1H-indol-1-yl]propanoyl}amino)-4-[(1-propyl-1H-pyrazol-4-yl)oxy]phenyl}butanoic acid

[Chem. 81]

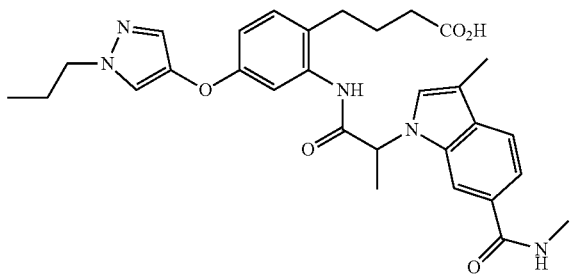

The same procedure as in Reference Example 13→Reference Example 6→Example 3 was carried out using the compound produced in Reference Example 35 instead of the compound produced in Reference Example 12 to obtain the compound of the present invention having the following physical property values.

TLC: Rf 0.65 (chloroform:methanol=9:1);

$^1$H-NMR (DMSO-d$_6$): δ 0.78, 1.42-1.60, 1.63-1.82, 2.00-2.12, 2.27, 2.30-2.46, 2.79, 3.97, 5.48, 6.74, 7.11, 7.30, 7.45, 7.47-7.56, 7.71, 8.08, 8.29, 9.55, 12.06.

Reference Example 36

4-(4-ethoxy-4-oxobutyl)-3-nitrobenzoic acid

To a solution of ethyl 4-(4-formyl-2-nitrophenyl)butanoate (WO 2016/111347, Reference Example 7, 18.3 g) in tert-butyl alcohol (21 mL), an aqueous solution (7 mL) of sodium dihydrogen phosphate (1.36 g) and 2-methyl-2-butene (5.29 mL), a sodium hypochlorite aqueous solution (4.35 mL) were added, and the resulting mixture was stirred at room temperature for 30 minutes. To the reaction mixture, 1 mol/L hydrochloric acid aqueous solution was added, followed by extraction with ethyl acetate. The organic layer was washed with water and saturated brine, dried over anhydrous sodium sulfate, and concentrated under reduced pressure to obtain residue. The resulting residue was washed with hexane to obtain the title compound (2.88 g) having the following physical property values.

$^1$H-NMR (DMSO-d$_6$): δ 1.18, 1.78-1.93, 2.35, 2.88, 4.03, 7.65, 8.14, 8.36.

Reference Example 37

Ethyl 4-[4-(2-acetylhydrazinecarbonyl)-2-nitrophenyl]butanoate

The same procedure as in Reference Example 1 was carried out using the compound produced in Reference Example 37 instead of 3-methylindole-6-carboxylic acid, and acetohydrazide to obtain the titled compound having the following physical property values.

TLC: Rf 0.31 (dichloromethane:methanol=9:1);

$^1$H-NMR (DMSO-d$_6$): δ 1.16, 1.79-1.90, 1.92, 2.35, 2.88, 4.02, 7.62, 8.10, 8.39, 9.99, 10.56.

Reference Example 38

Ethyl 4-[4-(5-methyl-1,3,4-oxadiazol-2-yl)-2-nitrophenyl]butanoate

To a solution of the compound (228 mg) produced in Reference Example 37 in THF (5 mL), Burgess Reagent (methyl N-(triethylammoniumsulfonyl carbamate) (322 mg) was added at room temperature. The resulting mixture was stirred using a microwave reaction device (manufactured by Biotage AB) at 100° C. for 20 minutes. To the reaction mixture, a saturated sodium hydrogencarbonate aqueous solution was poured, followed by extraction with ethyl acetate. The resulting organic layer was washed with saturated brine, and dried over anhydrous magnesium sulfate, followed by concentration under reduced pressure. The resulting residue was purified by silica gel column chromatography to obtain the title compound (199 mg) having the following physical property values.

TLC: Rf 0.33 (hexane:ethyl acetate=1:1);

$^1$H-NMR (CDCl$_3$): δ 1.28, 2.04, 2.41, 2.65, 3.00, 4.16, 7.55, 8.21, 8.51.

Example 15

4-[2-({2-[3-methyl-6-(methylcarbamoyl)-1H-indol-1-yl]propanoyl}amino)-4-(5-methyl-1,3,4-oxadiazol-2-yl)phenyl]butanoic acid

[Chem. 82]

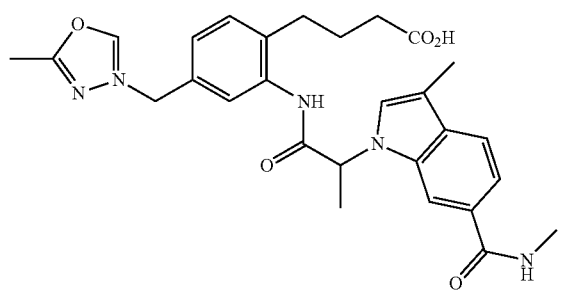

The same procedure as in Reference Example 5→Reference Example 6→Example 3 was carried out using the compound of Reference Example 38 instead of the compound of Reference Example 4 to obtain the compound of the present invention having the following physical property values.

TLC: Rf 0.37 (dichloromethane:methanol=9:1);

$^1$H-NMR (DMSO-$d_6$): δ 1.61, 1.79, 2.12, 2.38-2.67, 5.53, 7.38, 7.47-7.57, 7.72, 7.97, 8.12, 8.30, 9.80.

Example 15-1

The compound of Example 15 was subjected to optical resolution by SFC to obtain the compound of the present invention having the following physical property values.

Example 15-1(1)

4-[2-({2-[3-methyl-6-(methylcarbamoyl)-1H-indol-1-yl]propanoyl}amino)-4-(5-methyl-1,3,4-oxadiazol-2-yl)phenyl]butanoic acid (First Peak)

SFC retention time (min): 4.20 (CHIRALPAK ID 5 μm, 20 mm×250 (manufactured by Daicel Corporation); carbon dioxide:methanol=70:30).

Example 15-1(2)

4-[2-({2-[3-methyl-6-(methylcarbamoyl)-1H-indol-1-yl]propanoyl}amino)-4-(5-methyl-1,3,4-oxadiazol-2-yl)phenyl]butanoic acid (Second Peak)

SFC retention time (min): 6.60 (CHIRALPAK ID 5 μm, 20 mm×250 (manufactured by Daicel Corporation); carbon dioxide:methanol=70:30).

Reference Example 39

N'-[(4-bromo-3-nitrophenyl)acetyl]-2-methylpropanehydrazide

The same procedure as in Reference Example 1 was carried out using 2-(4-bromo-3-nitrophenyl)acetic acid (CAS No., 1261603-30-8) instead of 3-methylindole-6-carboxylic acid to obtain the title compound having the following physical property values.

TLC: Rf 0.33 (dichloromethane:methanol=9:1);

$^1$H-NMR (CDCl$_3$): δ 1.20, 2.40-2.57, 3.65, 7.40, 7.69, 7.81, 8.29, 8.85.

Reference Example 40

2-[(4-bromo-3-nitrophenyl)methyl]-5-(propan-2-yl)-1,3,4-oxadiazole

The same procedure as in Reference Example 38 was carried out using the compound of Reference Example 39 instead of the compound of Reference Example 37 to obtain the title compound having the following physical property values.

TLC: Rf 0.64 (hexane:ethyl acetate=1:3);

$^1$H-NMR (CDCl$_3$): δ 1.36, 3.15, 4.21, 7.40, 7.73, 7.83.

Example 16

4-{4-[(5-isopropyl-1,3,4-oxadiazol-2-yl)methyl]-2-({2-[3-methyl-6-(methylcarbamoyl)-1H-indol-1-yl]propanoyl}amino)phenyl}butanoic acid

[Chem. 83]

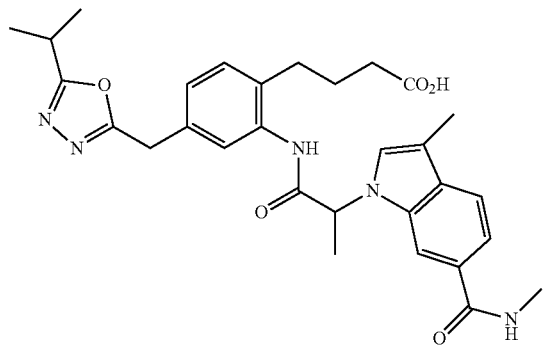

The same procedure as in Reference Example 5→Reference Example 6→Example 3 was carried out using the compound of Reference Example 40 instead of the compound of Reference Example 4 to obtain the compound of the present invention having the following physical property values.

TLC: Rf 0.37 (dichloromethane:methanol=9:1);

$^1$H-NMR (DMSO-$d_6$): δ 1.22, 1.55, 1.73, 2.06, 2.27, 2.33-2.58, 2.80, 3.10, 3.25-3.45, 4.14, 5.46, 7.04, 7.14, 7.17, 7.28, 7.44, 7.54, 8.11, 8.30, 9.63, 11.96.

Example 16-1

The compound of Example 16 was subjected to optical resolution by SFC to obtain the compound of the present invention having the following physical property values.

Example 16-1(1)

4-{4-[(5-isopropyl-1,3,4-oxadiazol-2-yl)methyl]-2-({2-[3-methyl-6-(methylcarbamoyl)-1H-indol-1-yl]propanoyl}amino)phenyl}butanoic acid (First Peak)

SFC retention time (min): 4.31 (CHIRALPAK IA 5 μm, 20 mm×250 (manufactured by Daicel Corporation); carbon dioxide:methanol=80:20).

Example 16-1(2)

4-{4-[(5-isopropyl-1,3,4-oxadiazol-2-yl)methyl]-2-({2-[3-methyl-6-(methylcarbamoyl)-1H-indol-1-yl]propanoyl}amino)phenyl}butanoic acid (Second Peak)

SFC retention time (min): 6.65 (CHIRALPAK IA 5 μm, 20 mm×250 (manufactured by Daicel Corporation); carbon dioxide:methanol=80:20).

Reference Example 41

Ethyl 4-{4-[hydroxy(1,3-thiazol-2-yl)methyl]-2-nitrophenyl}butanoate

Under argon substitution under ice cooling, to a solution of 2-bromo thiazole (370 mg) in THF (5 mL), isopropyl magnesium chloride-lithium chloride complex (1.7 mL, 1.3 mol/L THF solution) was dropwise. The resulting mixture was stirred under ice cooling for one hour. To the reaction solution, a solution of ethyl 4-(4-formyl-2-nitrophenyl)butanoate (WO 2016/111347, Reference Example 7, 500 mg) in THF (3 mL) added drop wise. The resulting mixture was stirred under ice cooling for 30 minutes. The reaction solution was added to an aqueous solution of saturated ammonium chloride, followed by extraction with ethyl acetate. The organic layer was washed with saturated brine, dried over anhydrous sodium sulfate, followed by concentration under reduced pressure. The resulting residue was purified by silica gel column chromatography to obtain the title compound (360 mg) having the following physical property values.

TLC: Rf 0.33 (hexane:ethyl acetate 2:1);

$^1$H-NMR (CDCl$_3$): δ 1.26, 1.93-2.06, 2.39, 2.87-2.96, 3.56, 4.13, 6.13, 7.35, 7.39, 7.65, 7.76, 8.06.

Reference Example 42

Ethyl 4-{2-nitro-4-[(1,3-thiazol-2-yl)methyl]phenyl}betanoate

To a solution of the compound (70 mg) produced in Reference Example 41 in 1,4-dioxane (1.5 mL), a Lawesson's reagent (40 mg) and hexacarbonylmolybdenum (2.5 mg) were added, and the resulting mixture was heated and stirred using microwave at 170° C. for 30 minutes. The reaction solution was purified by silica gel column chromatography to obtain the title compound (60 mg) having the following physical property values.

TLC: Rf 0.82 (hexane:ethyl acetate=2:1);

$^1$H-NMR (CDCl$_3$): δ 1.26, 1.91-2.06, 2.38, 2.85-2.95, 4.14, 4.39, 7.25, 7.33, 7.48, 7.73, 7.87.

Reference Example 43

Ethyl 4-{2-amino-4-[(1,3-thiazol-2-yl)methyl]phenyl}butanoate

To a solution of the compound (60 mg) produced in Reference Example 42 in acetic acid (1 mL), iron (50 mg) was added, and stirred 50° C. for 90 minutes. The reaction solution was diluted with ethyl acetate, and saturated sodium hydrogencarbonate aqueous solution was added thereto, followed by filtration through celite (trade name). The filtrate was extracted with ethyl acetate, the organic layer was washed with saturated brine, and dried over anhydrous sodium sulfate, followed by concentration under reduced pressure. The resulting residue was purified by silica gel column chromatography to obtain the title compound (40 mg) having the following physical property values.

TLC: Rf 0.18 (hexane:ethyl acetate=1:2);

$^1$H-NMR (CDCl$_3$): δ 1.27, 1.83-1.95, 2.39, 2.46-2.55, 3.87, 4.15, 4.23, 6.63, 6.65, 6.97, 7.19, 7.69.

Example 17

4-[2-({2-[3-methyl-6-(methylcarbamoyl)-1H-indol-1-yl]propanoyl}amino)-4-(1,3-thiazol-2-ylmethyl)phenyl]butanoic acid

[Chem. 84]

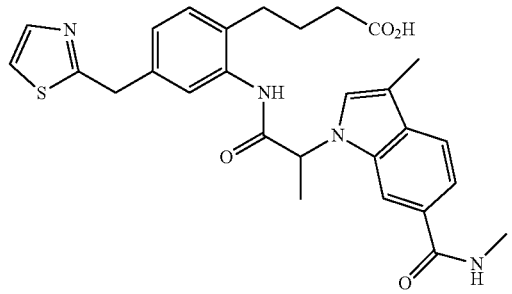

The same procedure as in Reference Example 6→Example 3 was carried out using the compound of Reference Example 43 instead of the compound of Reference Example 5 to obtain the compound of the present invention having the following physical property values.

TLC: Rf 0.46 (dichloromethane:methanol=10:1);

$^1$H-NMR (DMSO-d$_6$): δ 1.56, 1.73, 2.06, 2.27, 2.32-2.68, 2.80, 4.24, 5.47, 7.08, 7.13, 7.29-7.33, 7.46, 7.49-7.56, 7.67, 8.10, 8.24-8.33, 9.60-9.68, 12.04.

Example 17-1

The compound of Example 17 was subjected to optical resolution by SFC to obtain the compound of the present invention having the following physical property values.

Example 17-1(1)

4-[2-({2-[3-methyl-6-(methylcarbamoyl)-1H-indol-1-yl]propanoyl}amino)-4-(1,3-thiazol-2-ylmethyl)phenyl]butanoic acid (First Peak)

SFC retention time (min): 3.45 (CHIRALPAK ID 5 μm, 20 mm×250 (manufactured by Daicel Corporation); carbon dioxide:methanol=70:30).

Example 17-1(2)

4-[2-({2-[3-methyl-6-(methylcarbamoyl)-1H-indol-1-yl]propanoyl}amino)-4-(1,3-thiazol-2-ylmethyl)phenyl]butanoic acid (Second Peak)

SFC retention time (min): 5.03 (CHIRALPAK ID 5 μm, 20 mm×250 (manufactured by Daicel Corporation); carbon dioxide:methanol=70:30).

Reference Example 44

Reference Example 44(1)

Ethyl 4-{4-[hydroxy(1-methyl-1H-pyrazol-4-yl)methyl]-2-nitrophenyl}butanoate

Reference Example 44(2)

Ethyl 4-{4-[hydroxy(4-iodo-1-methyl-1H-pyrazol-5-yl)methyl]-2-nitrophenyl}butanoate Under argon substitution, to a solution of 4-iodo-1-methylpyrazole (600 mg) in THF (10 mL), a solution of n-butyllithium in hexane (1.8 mL, 1.6 mol/L) was added dropwise at −78° C. for five minutes. To the reaction solution, a THF solution (10 mL) of ethyl 4-(4-formyl-2-nitrophenyl)butanoate (WO 2016/111347, Reference Example 7, 700 mg) was added dropwise, and stirred at −78° C. for 40 minutes. The reaction solution was added to an aqueous solution of saturated ammonium chloride, followed by extraction with ethyl acetate. The organic layer was washed with saturated brine, and dried over anhydrous sodium sulfate, followed by concentration under reduced pressure. The resulting residue was purified by silica gel column chromatography to obtain the title compound having the following physical property values (the compound of Reference Example 44(1): 170 mg, the compound of Reference Example 44(2): 210 mg).

Reference Example 44(1)

TLC: Rf 0.07 (hexane:ethyl acetate=1:1);
$^1$H-NMR (DMSO-$d_6$): δ 1.27, 1.94-2.05, 2.39, 2.88-2.97, 3.87, 4.14, 5.88, 7.25, 7.36, 7.40, 7.57, 7.97.

Reference Example 44(2)

TLC: Rf 0.59 (hexane:ethyl acetate=1:1);
$^1$H-NMR (DMSO-$d_6$): δ 1.15, 1.78-1.86, 2.32, 2.79-2.84, 3.67, 4.01, 6.02, 6.70, 7.42, 7.47-7.51, 7.87.

Reference Example 45

Ethyl 4-{2-amino-4-[(1-methyl-1H-pyrazol-4-yl)methyl]phenyl}butanoate

To a solution of the compound (150 mg) produced in Reference Example 44(1) in acetic acid (2 mL)-methanol (2 mL), 10% Pd—C (170 mg) was added, the resulting mixture was stirred in substitution of hydrogen at 50° C. for two hours. The reaction solution was filtered through celite (trade name), and concentrated under reduced pressure to obtain residue. The resulting residue was purified by silica gel column chromatography (Yamazen NH silica gel) to obtain the title compound (56 mg) having the following physical property values.
TLC: Rf 0.74 (ethyl acetate);
$^1$H-NMR (CDCl$_3$): δ 1.27, 1.83-1.95, 2.39, 2.45-2.54, 3.69, 3.80, 3.82, 4.15, 6.51, 6.55, 6.93, 7.11, 7.32.

Example 18

4-{2-({2-[3-methyl-6-(methylcarbamoyl)-1H-indol-1-yl]propanoyl}amino)-4-[(1-methyl-1H-pyrazol-4-yl)methyl]phenyl}butanoic acid

[Chem. 85]

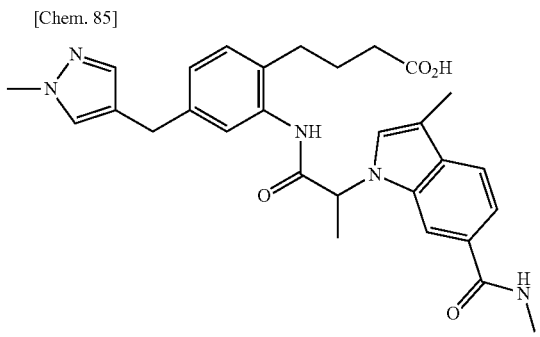

The same procedure as in Reference Example 6→Example 3 was carried out using the compound produced in Reference Example 45 instead of the compound produced in Reference Example 5 to obtain the compound of the present invention having the following physical property values.
TLC: Rf 0.49 (dichloromethane:methanol=10:1);
$^1$H-NMR (CDCl$_3$): δ 1.60-1.77, 2.29-2.58, 3.09, 3.78, 3.83, 5.78, 6.41-6.49, 6.86, 6.99, 7.12, 7.19-7.26, 7.32, 7.52, 7.63, 8.14, 8.88, 9.32.

Example 18-1

The compound of Example 18 was subjected to optical resolution by SFC to obtain the compound of the present invention having the following physical property values.

Example 18-1(1)

4-{2-({2-[3-methyl-6-(methylcarbamoyl)-1H-indol-1-yl]propanoyl}amino)-4-[(1-methyl-1H-pyrazol-4-yl)methyl]phenyl}butanoic acid (First Peak)

SFC retention time (min): 8.69 (CHIRALPAK ID 5 μm, 20 mm×250 (manufactured by Daicel Corporation); carbon dioxide:methanol=70:30).

Example 18-1(2)

4-{2-({2-[3-methyl-6-(methylcarbamoyl)-1H-indol-1-yl]propanoyl}amino)-4-[(1-methyl-1H-pyrazol-4-yl)methyl]phenyl}butanoic acid (Second Peak)

SFC retention time (min): 10.68 (CHIRALPAK ID 5 μm, 20 mm×250 (manufactured by Daicel Corporation): carbon dioxide:methanol=70:30).

Example 18-2

4-{2-({2-[3-methyl-6-(methylcarbamoyl)-1H-indol-1-yl]propanoyl}amino)-4-[(1-methyl-1H-pyrazol-5-yl)methyl]phenyl}butanoic acid The same procedure as in Reference Example 5→Reference Example 6→Example 3 was carried out using the compound produced in Reference Example 44(2) instead of the compound produced in Reference Example 5 to obtain the compound of the present invention having the following physical property values.
TLC: Rf 0.58 (dichloromethane:methanol=10:1);
$^1$H-NMR (DMSO-$d_6$): δ 1.55, 1.73, 2.06, 2.27, 2.31-2.66, 2.80, 3.63, 3.93, 5.46, 5.94, 6.95, 7.11, 7.20, 7.24, 7.45, 7.48-7.56, 8.11, 8.24-8.32, 9.61, 12.03.

Reference Example 46

Ethyl 4-(4-[hydroxy(1-methyl-1H-pyrazol-4-yl)methyl]-2-{2-[3-methyl-6-(methylcarbamoyl)-1H-indol-1-yl]propanamido}phenyl)butanoate The same procedure as in Reference Example 5→Reference Example 6 was carried out using the compound produced in Reference Example 44(1) instead of the compound produced in Reference Example 5 to obtain the title compound having the following physical property values.

$^1$H-NMR (CDCl$_3$): δ 1.27, 1.45-1.55, 1.91, 2.11-2.27, 2.37, 3.01, 3.82, 4.17, 5.44, 5.75, 6.26-6.38, 7.00-7.12, 7.21, 7.30-7.35, 7.37, 7.46, 7.59, 7.85-7.94, 8.00, 8.07.

Example 18-3

4-{4-[hydroxy(1-methyl-1H-pyrazol-4-yl)methyl]-2-({2-[3-methyl-6-methylcarbamoyl)-1H-indol-1-yl]propanoyl}amino)phenyl}butanoic acid The same procedure as in Example 3 was carried out using the compound produced in Reference Example 46 instead of the compound produced in Reference Example 16 to obtain the compound of the present invention having the following physical property values.
TLC: Rf 0.50 (dichloromethane:methanol=10:1);
$^1$H-NMR (DMSO-d$_6$): δ 1.48-1.64, 1.74, 2.05, 2.27, 2.33-2.55, 2.80, 3.72, 5.39-5.58, 7.08-7.20, 7.28-7.39, 7.43-7.57, 8.11, 8.22-8.34, 9.62, 12.03.

Reference Example 47

Ethyl 4-[2-{2-[3-methyl-6-(methylcarbamoyl)-1H-indol-1-yl]propanamido}-4-(1-methyl-1H-pyrazole-4-carbonyl)phenyl]butanoate To a solution of the compound (50 mg) produced in Reference Example 46 in dichloromethane (4 mL), manganese dioxide (115 mg) was added, and the resulting mixture was stirred overnight at room temperature. The reaction solution was filtered through celite (trade name) and concentrated under reduced pressure to obtain residue, the resulting residue was purified by silica gel column chromatography to obtain the title compound (50 mg) having the following physical property values.
TLC: Rf 0.35 (ethyl acetate);
$^1$H-NMR (CDCl$_3$): δ 1.28, 1.48-1.65, 1.92, 2.14-2.34, 2.38, 3.02, 3.98, 4.19, 5.49, 6.22-6.35, 7.16-7.22, 7.26-7.30, 7.32-7.37, 7.41-7.47, 7.52-7.57, 7.58-7.64, 7.99-8.09, 8.54.

Example 18-4

4-{2-({2-[3-methyl-6-(methylcarbamoyl-1H-indol-1-yl]propanoyl}amino)-4-[(1-methyl-1H-pyrazol-4-yl)carbonyl]phenyl}butanoic acid

[Chem. 86]

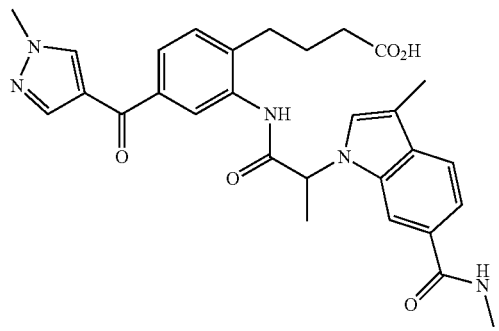

The same procedure as in Example 3 was carried out using the compound produced in Reference Example 47 instead of the compound produced in Reference Example 16 to obtain the compound of the present invention having the following physical property values.
TLC: Rf 0.48 (dichloromethane:methanol=10:1);
$^1$H-NMR (DMSO-d$_6$): δ 1.63, 1.77, 2.13, 2.28, 2.33-2.67, 2.79, 3.88, 5.53, 7.36, 7.47-7.63, 7.83, 7.89, 8.12, 8.25-8.34, 9.81, 12.09.

Example 18-5

The compound of Example 18-4 was subjected to optical resolution by SFC to obtain the compound of the present invention having the following physical property values.

Example 18-5(1)

4-{2-({2-[3-methyl-6-(methylcarbamoyl-1H-indol-1-yl]propanoyl}amino)-4-[(1-methyl-1H-pyrazol-4-yl)carbonyl]phenyl}butanoic acid (First Peak)

SFC retention time (min): 8.10 (CHIRALPAK IA 5 μm, 20 mm×250 (manufactured by Daicel Corporation); carbon dioxide:methanol=80:20).

Example 18-5(2)

4-{2-({2-[3-methyl-6-(methylcarbamoyl-1H-indol-1-yl]propanoyl}amino)-4-[(1-methyl-1H-pyrazol-4-yl)carbonyl]phenyl}butanoic acid (Second Peak)

SFC retention time (min): 9.79 (CHIRALPAK IA 5 μm, 20 mm×250 (manufactured by Daicel Corporation); carbon dioxide:methanol=80:20).

Reference Example 48

Ethyl 4-(4-formyl-2-{2-[3-methyl-6-(methylcarbamoyl)-1H-indol-1-yl]propanamido}phenyl)butanoate To a solution of the compound (500 mg) produced in Reference Example 6 in ethyl acetate (3 mL) and dimethyl sulfoxide (3 mL), triethylamine (0.9 mL) and pyridine-sulfur trioxide complex (700 mg) were added, and the resulting mixture was stirred at room temperature for 30 minutes. To the reaction solution, isopropanol (1 mL) was added so as to be quenched. The resulting solution was diluted with ethyl acetate and hexane, washed with water and saturated brine, dried over anhydrous sodium sulfate, and concentrated under reduced pressure to obtain the title compound (500 mg) having the following physical property values.
TLC: Rf 0.50 (hexane:ethyl acetate=1:3);
$^1$H-NMR (CDCl$_3$): δ 1.29, 1.48-1.63, 1.92, 2.19-2.40, 3.02, 4.21, 5.54, 6.21-6.33, 7.22, 7.37, 7.44, 7.55-7.63, 8.05, 8.27, 8.63, 9.93.

Reference Example 49

Ethyl 4-[4-(hydrazinylmethyl)-2-{2-[3-methyl-6-(methylcarbamoyl)-1H-indol-1-yl]propanamido}phenyl]butanoate hydrochloride To a solution of the compound (500 mg) produced in Reference Example 48 in dichloromethane (10 mL), tert-butyl N-amino carbamate (152 mg) and acetic acid (70 mg) were added. The resulting mixture was stirred at room temperature for 45 minutes. To the reaction solution, triacetoxy sodium borohydride (333 mg) was added, and the resulting mixture was stirred at room temperature for 30 minutes. The reaction solution was diluted with ethyl acetate, washed with a saturated sodium hydrogencarbonate aqueous solution and saturated brine, dried over anhydrous sodium sulfate, concentrated under reduced pressure to obtain residue. The resulting residue was purified by silica gel column chromatography. To a solution of the obtained crude product in ethyl acetate (20 mL)-DMF (4 mL), 10% Pd—C (150 mg) was added, and then the resulting mixture was stirred under hydrogen gas atmosphere at room temperature for 15 minutes. The reaction solution was subjected to celite filtration, and concentrated under reduced pressure to obtain residue. Then, the resulting residue was diluted with ethyl acetate and hexane, washed with a saturated sodium hydrogencarbonate aqueous solution and saturated brine, dried over anhydrous sodium sulfate, followed by concentration under reduced pressure. To a solution of the resulting crude product in methanol (2 mL)-1,4-dioxane (2 mL), a solution of 1,4-dioxane in hydrochloric acid (5 mL, 4 mol/L) was added and stirred at room temperature for one hour. The reaction solution was diluted with ethyl acetate, and deposited precipitate was filtered to obtain the title compound (280 mg) having the following physical property values.

TLC: Rf 0.50 (hexane:ethyl acetate=1:3);

$^1$H-NMR (DMSO-d$_6$): δ 1.15, 1.51-1.63, 1.75, 2.03-2.15, 2.27, 2.41-2.58, 3.55, 4.01, 5.57, 7.12-7.22, 7.34-7.37, 7.45-7.59, 8.33, 8.36-8.46, 9.96.

Reference Example 50

Ethyl 4-(2-{2-[3-methyl-6-(methylcarbamoyl)-1H-indol-1-yl]propanamino}-4-[(5-methyl-1H-1,2,4-triazol-1-yl)methyl]phenyl)butanoate To a solution of 1,1-dimethoxy-N,N-dimethylmethaneamine (28 mg) in 1,4-dioxane (0.5 mL), acetamide (15 mg) was added, and pressure is reduced to 150 torr. The resulting mixture was stirred at 50° C. for 30 minutes. To the reaction solution, 1,1-dimethoxy-N,N-dimethylmethaneamine (35 mg) was added, and the resulting mixture was stirred for further 30 minutes. Then, the reaction solution was concentrated under reduced pressure. To a solution of the resulting residue in acetic acid (1 mL), the compound (100 mg) produced in Reference Example 49 was added. The resulting product was heated using microwave at 150° C. for 45 minutes. The reaction solution was concentrated under reduced pressure to obtain residue, and the resulting residue was purified by silica gel column chromatography (NH silica gel) to obtain the title compound (60 mg) having the following physical property values.

TLC: Rf 0.50 (ethyl acetate:methanol=10:1);

$^1$H-NMR (CDCl$_3$): δ 1.26, 1.38-1.53, 1.91, 2.08-2.24, 2.36, 2.42, 3.02, 4.17, 5.16-5.28, 5.47, 6.25-6.36, 6.76, 7.00, 7.33, 7.44, 7.59, 7.79, 7.90-8.11.

Example 19

4-{2-({2-[3-methyl-6-(methylcarbamoyl)-1H-indol-1-yl]propanoyl}amino)-5-[(5-methyl-1H-1,2,4-triazol-1-yl)methyl]phenyl}butanoic acid

[Chem. 87]

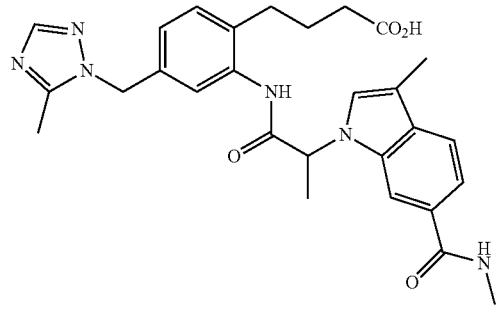

The same procedure as in Example 3 was carried out using the compound produced in Reference Example 50 instead of the compound produced in Reference Example 16 to obtain the compound of the present invention having the following physical property values.

TLC: Rf 0.51 (dichloromethane:methanol=10:1);

$^1$H-NMR (DMSO-d$_6$): δ 0.67-0.88, 1.55, 1.73, 1.82-1.94, 2.05, 2.27, 2.32-2.67, 2.80, 5.18, 5.46, 7.02, 7.16, 7.27, 7.46, 7.48-7.56, 8.11, 8.24-8.33, 8.37, 9.68, 12.03.

Reference Example 51

Methyl 2-(4-cyano-2-nitrophenoxy)benzoate

Under an argon gas flow, a solution of methyl salicylate (879 mg), 4-fluoro-3-nitrobenzonitrile (800 mg), and cesium carbonate (2.20 g) in DMF (10 mL) was stirred at 80° C. for two hours. To the reaction mixture, water was added, followed by extraction with MTBE. The organic layer was washed with water and saturated brine, dried over anhydrous sodium sulfate, and concentrated under reduced pressure. The resulting residue was washed with MTBE/hexane solution, and then dried under reduced pressure to obtain the title compound (1.32 mg) having the following physical property values.

$^1$H-NMR (CDCl$_3$): δ 3.74, 6.78, 7.23, 7.45, 7.62-7.73, 8.08, 8.28.

Example 20

2-[4-cyano-2-[2-[3-methyl-6-(methylcarbamoyl)indol-1-yl]propanoylamino]phenoxy]benzoic acid

[Chem. 88]

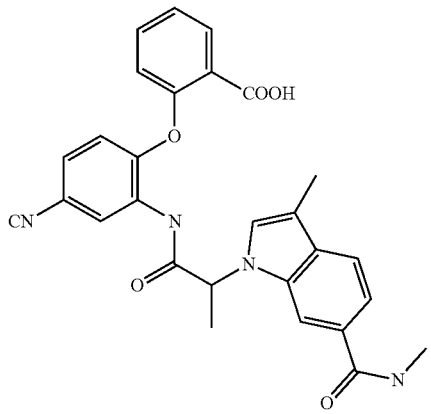

The same procedure as in Reference Example 5 was carried out using the compound produced in Reference Example 51 to obtain the corresponding amine product. The same procedure as in Reference Example 14→Example 3 was carried out using the obtained amine product instead of the compound produced in Reference Example 13, and using the compound synthesized in Reference Example 3 instead of the compound produced in Reference Example 11, to obtain the compound (49 mg) of the present invention having the following physical property values.

LC: Rf 0.41 (chloroform:methanol=9:1);
$^1$H-NMR (CD$_3$OD): δ 1.85, 2.22, 2.90, 5.50, 6.68, 6.95, 7.26-7.38, 7.41-7.49, 7.57, 7.87-7.99, 8.52.

Example 21

The compound of Example 20 was subjected to optical resolution by SFC to obtain the compound of the present invention having the following physical property values.

Example 21(1)

2-[4-cyano-2-[2-[3-methyl-6-(methylcarbamoyl)indol-1-yl]propanoylamino]phenoxy]benzoic acid (First Peak)

SFC retention time (min): 4.01 (CHIRALPAK IA 5 μm, 20 mm×250 (manufactured by Daicel Corporation); carbon dioxide:methanol=70:30).

Example 21(2)

2-[4-cyano-2-[2-[3-methyl-6-(methylcarbamoyl)indol-1-yl]propanoylamino]phenoxy]benzoic acid (Second Peak)

SFC retention time (min): 5.28 (CHIRALPAK IA 5 μm, 20 mm×250 (manufactured by Daicel Corporation); carbon dioxide:methanol=70:30).

Example 22

4-[2-[2-[3-methyl-6-(methylcarbamoyl)indol-1-yl]butanoylamino]-4-[(4-methylpyrazol-1-yl)methyl]phenyl]butanoic acid The same procedure as in Reference Example 2→Reference Example 3 was carried out using methyl 2-bromobutyrate instead of methyl 2-bromopropionate to obtain the corresponding carboxylic acid product. The same procedure as in Reference Example 14→Example 3 was carried out using the obtained carboxylic acid product instead of the compound produced in Reference Example 11 to obtain the compound (58 mg) of the present invention having the following physical property values.

TLC: Rf 0.31 (hexane:ethyl acetate=1:3);
$^1$H-NMR (DMSO-d$_6$): δ 0.85, 1.46-1.61, 1.91, 1.92-2.24, 2.25, 2.33-2.42, 2.80, 5.12, 5.25, 6.96, 7.08-7.24, 7.42-7.55, 8.15, 8.28, 9.74, 12.01.

Example 23

The compound of Example 22 was subjected to optical resolution by SFC to obtain the compound of the present invention having the following physical property values.

Example 23(1)

4-[2-[2-[3-methyl-6-(methylcarbamoyl)indol-1-yl]butanoylamino]-4-[(4-methylpyrazol-1-yl)methyl]phenyl]butanoic acid (First Peak)

SFC retention time (min): 2.55 (CHIRALPAK IA 5 μm, 20 mm×250 (manufactured by Daicel Corporation); carbon dioxide:methanol=70:30).

Example 23(2)

4-[2-[2-[3-methyl-6-(methylcarbamoyl)indol-1-yl]butanoylamino]-4-[(4-methylpyrazol-1-yl)methyl]phenyl]butanoic acid (Second Peak)

SFC retention time (min): 4.24 (CHIRALPAK IA 5 μm, 20 mm×250 (manufactured by Daicel Corporation); carbon dioxide:methanol=70:30).

Reference Example 52

N-methoxy-N,3-dimethyl-1H-indole-6-carboxamide

The same procedure as in Reference Example 1 was carried out using N,O-dimethylhydroxylamine hydrochloride instead of methylamine hydrochloride to obtain the title compound (920 mg) having the following physical property values.

TLC: Rf 0.33 (dichloromethane:methanol=9:1);
$^1$H-NMR (CDCl$_3$): δ 2.34, 3.39, 3.58, 7.08, 7.48, 7.57, 7.78.

Reference Example 53

1-(3-methyl-1H-indol-6-yl)ethan-1-one

Under an argon gas flow, to a solution of the compound produced in Reference Example 52 in anhydrous THF (20 mL), a solution of methyl lithium in diethyl ether (1.8 mol/L, 7.6 mL) was added dropwise at −78° C. and so as to increase the temperature from −78° C. to −20° C. over two hours. To the reaction solution, a saturated ammonium chloride aqueous solution was added, followed by extraction with ethyl acetate. The resulting organic layer was washed with saturated brine, dried over anhydrous sodium sulfate, and concentrated under reduced pressure. The resulting residue was washed with MTBE to obtain the title compound (505 mg) having the following physical property values.

TLC: Rf 0.57 (dichloromethane:methanol=9:1);
$^1$H-NMR (CD$_3$OD): δ 2.32, 2.64, 7.23, 7.54, 7.68, 8.03.

Example 24

4-[2-[2-(6-acetyl-3-methylindol-1-yl)propanoylamino]-4-[(4-methylpyrazol-1-yl)methyl]phenyl]butanoic acid The same procedure as in Reference Example 2→Reference Example 4 was carried out using the compound produced in Reference Example 53 instead of the compound produced in Reference Example 1 to obtain the corresponding carboxylic acid product. The same procedure as in Reference Example 14→Reference Example 3 was carried out using the corresponding carboxylic acid product instead of the compound produced in Reference Example 11 to obtain the compound (26 mg) of the present invention having physical property values.

TLC: Rf 0.40 (dichloromethane:methanol=9:1);
$^1$H-NMR (CDCl$_3$): δ 1.67-1.81, 2.05, 2.33, 2.38-2.62, 2.75, 5.21, 5.82, 6.84, 7.03, 7.18, 7.34, 7.56, 7.68, 7.75, 8.26, 8.86, 9.32.

Example 25

4-[2-[2-(6-acetyl-3-methylindol-1-yl)propanoylamino]-4-[(4-methylpyrazol-1-yl)methyl]phenyl]butanoic acid The compound of Example 24 was subjected to optical resolution by SFC to obtain the compound of the present invention having the following physical property values.

Example 25(1)

4-[2-[2-(6-acetyl-3-methylindol-1-yl)propanoylamino]-4-[(4-methylpyrazol-1-yl)methyl]phenyl]butanoic acid (First Peak)

SFC retention time (min): 2.12 (CHIRALPAK IA 5 μm, 20 mm×250 (manufactured by Daicel Corporation); carbon dioxide:methanol=70:30)

Example 25(2)

4-[2-[2-(6-acetyl-3-methylindol-1-yl)propanoylamino]-4-[(4-methylpyrazol-1-yl)methyl]phenyl]butanoic acid (Second Peak)

SFC retention time (min): 5.88 (CHIRALPAK IA 5 μm, 20 mm×250 (manufactured by Daicel Corporation); carbon dioxide:methanol=70:30)

Reference Example 54

Ethyl 4-{4-[methyl-1H-pyrazol-4-yl)carbamoyl]-2-nitrophenyl}butanoic acid

The same procedure as in Reference Example 14 was carried out using the compound produced in Reference Example 36 instead of the compound produced in Reference Example 13, and using N,1-dimethyl-1H-pyrazol-4-amine hydrochloride instead of the compound produced in Reference Example 11 to obtain the title compound (750 mg) having the following physical property values.

TLC: Rf 0.29 (hexane:ethyl acetate=1:4);
$^1$H-NMR (CDCl$_3$): δ 1.27, 1.85-2.10, 2.23-2.49, 2.73-3.06, 3.40, 3.62-4.02, 4.13, 7.10-7.35, 7.40-7.73, 7.83-8.09.

Example 26

4-[2-[2-[3-methyl-6-(methylcarbamoyl)indol-1-yl]propanoylamino]-4-[methyl-(1-methylpyrazol-4-yl)carbamoyl]phenyl]butanoic acid The same procedure as in Reference Example 5 was carried out using the compound produced in Reference Example 54 to obtain the corresponding amine product. The same procedure as in Reference Example 14→Example 3 was carried out using the resulting amine product instead of the compound produced in Reference Example 13, and using the compound produced in Reference Example 3 instead of the compound produced in Reference Example 11 to obtain the compound (72 mg) of the present invention having the following physical property values.

TLC: Rf 0.41 (chloroform:methanol=9:1);
$^1$H-NMR (CDCl$_3$): δ 1.56-1.86, 2.32, 2.35-2.67, 3.08, 3.38, 3.61-4.06, 5.78, 6.47, 6.85-7.26, 7.52, 7.62, 7.99-8.50, 8.87, 9.21-9.69.

Pharmacological Experiment Examples

Pharmacological Experiment Example 1

EP$_4$ Antagonistic Activity Measurement Experiment Using Prostanoid Receptor Subtype Expressing Cells CHO cells expressing human EP$_4$ receptor subtypes were prepared according to the methods of Nishigaki et al. (Non-Patent Literature 4), and used for experiment. Cells cultured to subconfluent were detached, and suspended in an assay medium (MEM containing 1 mmol/L IBMX, 1% HSA) such that a concentration became 1×10$^6$ cells/mL. For reaction, PGE$_2$ was added to the cell suspension (25 μL) in a final concentration of 10 nmol/L, either alone or as a 25-μL PGE$_2$ solution containing the test compound. After 30 minutes of reaction at room temperature, the amount of cAMP in the cells was quantified according to the method in the descriptions of the cAMP assay kit (CISBIO).

Note here that the antagonistic effect (IC$_{50}$ value) of the test compound was calculated as a value that represents an inhibition rate against a reaction with PGE$_2$ alone at 10 nM, a concentration that produces a submaximal cAMP producing effect.

The above pharmacological experiment showed that the present compounds had strong EP$_4$ receptor antagonistic activity. As examples, Table 1 below shows the IC$_{50}$ values of some of the present compounds. On the other hand, the EP$_4$ receptor antagonistic activity of the compound of Example 2-24 described in Patent Literature 3, that is, 4-[4-cyano-2-[2-(indol-3-yl)propanoylamino]phenyl]butanoic acid was 0.36 μM.

TABLE 1

| Example No. | EP$_4$ antagonistic activity IC$_{50}$ (µM) |
|---|---|
| 1 | 0.027 |
| 1-5 | 0.0049 |
| 1-14 | 0.0033 |
| 2 | 0.039 |
| 2-6(2) | 0.0012 |
| 2-18 | 0.0055 |
| 2-27(4) | 0.0018 |
| 3-3(2) | 0.0009 |
| 3-5(2) | 0.0021 |
| 3-7(2) | 0.0017 |
| 3-9(2) | 0.0007 |
| 3-11(2) | 0.0046 |
| 3-20(2) | 0.0014 |
| 4-1(2) | 0.0025 |
| 4-8(2) | 0.0027 |
| 6-5(1) | 0.0027 |
| 7-1(2) | 0.0033 |
| 7-3(2) | 0.0015 |
| 8-3(2) | 0.0048 |
| 8-9(2) | 0.0033 |
| 8-13(2) | 0.0063 |
| 8-17(2) | 0.0086 |
| 9-1(2) | 0.0046 |
| 9-5(2) | 0.0022 |
| 10-1(2) | 0.0037 |
| 11-1(2) | 0.0013 |
| 11-3(2) | 0.0027 |
| 11-7(2) | 0.0016 |
| 11-8 | 0.004 |
| 11-11(2) | 0.002 |
| 11-15(2) | 0.0019 |
| 11-23(2) | 0.0065 |
| 11-25(2) | 0.00057 |
| 11-30(2) | 0.012 |
| 12-1(2) | 0.0016 |
| 13 | 0.00079 |
| 15-1(2) | 0.0064 |
| 18-3 | 0.0062 |
| 18-5(2) | 0.0032 |

Pharmacological Experiment Example 2

EP$_3$ Binding Activity Measurement Experiment Using Prostanoid Receptor Subtype Expressing Cells To each well of a 96 well plate, 10 µL of a medium (dimethyl sulfoxide; DMSO) which had been 10-fold diluted with an assay buffer solution (10 mmol/L KH$_2$PO$_4$—KOH containing 1 mmol/L EDTA, 10 mmol/L Mg$^{2+}$ and 100 mmol/L NaCl, pH6.0) or a DMSO solution of a test compound (final concentration of DMSO: 0.5%), 90 µL of assay buffer solution, 50 µL of 10 nmol/L [$^3$H]-PGE$_2$ (final concentration: 2.5 nmol/L), and 50 µL of human EP$_3$ receptor expressing cell membrane fraction (manufactured by Millipore) (membrane protein mass: 2.5 µg) were placed, and subjected to incubation at room temperature. In nonspecific binding group, instead of the medium, 2 mmol/L of PGE$_2$ was added (final concentration of PGE$_2$: 10 µmol/L). After 60 minutes, a membrane fraction was subjected to suction filtration using a cell harvester, and collected onto a glass fiber (GF/B) plate (hereinafter, "filter plate") which had been wetted with a washing buffer solution (10 mmol/L KH$_2$PO$_4$—KOH containing 100 mmol/L NaCl, pH6.0) in advance. Furthermore, an operation of adding about 0.2 mL of the washing buffer solution to the 96 well plate after suction filtration, and carrying out suction filtration was repeated twice, and the remaining membrane fractions were collected. The filter plate was washed with 150 mL of washing buffer solution twice, and then dried at 50° C. to 60° C. for about 60 minutes. After an accessary back seal was attached to the bottom surface of the filter plate, about 50 µL per well of liquid scintillation cocktail was added to the filter plate, and a scaling film sheet was attached to the upper surface of the filter plate. The filter plate was shaken, and then radioactivity (cpm) of the filter plate was measured using a microplate scintillation counter. A specific binding amount of [$^3$H]-PGE$_2$ to EP$_3$ receptor was calculated by subtracting the radioactivity of the nonspecific binding group from the radioactivity other than the radioactivity of the nonspecific binding group. The inhibition rate by the test compound was calculated from the specific binding amount of [$^3$H]-PGE$_2$ in a medium group and the compound of the present invention group, a Ki value (dissociation constant of the test compound) was calculated from estimated IC$_{50}$ value (the concentration of the test compound required for inhibiting 50% with respect to the specific binding amount of the medium group) according to the following formula.

$$Ki=IC_{50}/(1+([L]^*/Kd))$$

[L]*: concentration of [$^3$H]-PGE$_2$ (2.5 nmol/L)
Kd: dissociation constant of [$^3$H]-PGE$_2$ Note here that the Kd value of [$^3$H]-PGE$_2$ was estimated from nonlinear regression analysis by calculating a specific binding amount at the time when [$^3$H]-PGE$_2$ having various concentrations according to the above method was added. As a result, it was shown that the compound of the present invention had weak binding activity with respect to EP$_3$ receptor, and was an antagonist selective to the EP$_4$ receptor. Some measurement results of the compound of the present invention are shown in Table 2. Note here that binding activities with respect to EP1 and EP2 receptors can be measured by the same method as the measurement experiment of the EP3 binding activity measurement experiment.

TABLE 2

| Example No. | EP$_3$ binding activity Ki (µM) |
|---|---|
| 1 | >10 |
| 3-9(2) | 0.41 |
| 8-3(2) | 1.5 |
| 8-13(2) | 1.6 |
| 11-15(2) | 2.3 |
| 18-5(2) | 0.12 |

FORMULATION EXAMPLES

Formulation Example

The following components were mixed and punched using an ordinary method to obtain 10,000 tablets containing 10 mg of the active component per tablet.

| | |
|---|---|
| 4-{4-[(1,1-dioxide-1,2-thiazolidin-2-yl)methyl]-2-({2-[3-methyl-6-(methylcarbamoyl)-1H-indol-1-yl]propanoyl}amino)phenyl}butanoic acid ... | 100 g |
| Carboxymethyl cellulose calcium (disintegrator): | 20 g |
| Magnesium stearate (lubricant): | 10 g |
| Microcrystalline cellulose: | 870 g |

INDUSTRIAL APPLICABILITY

A compound of the present invention has antagonistic activity with respect to an EP$_4$ receptor, and is effective for preventing and/or treating diseases caused by activation of an EP$_4$ receptor.

The invention claimed is:
1. A compound of formula (I-0), or a pharmaceutically acceptable salt thereof:

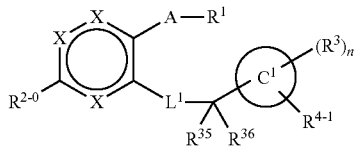

(I-0)

wherein
$R^1$ represents $COOR^5$, tetrazole, $SO_3H$, $SO_2NH_2$, $SO_2NHR^6$, $CONHSO_2R^7$, $SO_2NHCOR^8$, or hydroxamic acid,
$R^5$ represents a hydrogen atom, C1-4 alkyl, or benzyl,
$R^6$, $R^7$, and $R^8$ each independently represent C1-4 alkyl, a C3-10 carbon ring, or a 3- to 10-membered heterocycle, wherein C1-4 alkyl, benzyl, a C3-10 carbon ring, and a 3- to 10-membered heterocycle in $R^5$, $R^6$, $R^7$, and $R^8$, each independently may be substituted with 1 to 5 $R^9$s,
$R^9$ represents a halogen atom, C1-4 alkyl, C1-4 alkoxy, C1-4 alkylthio, or cyano, wherein when two or more $R^9$s are present, a plurality of $R^9$'s may be the same as or different from each other, and wherein C1-4 alkyl, C1-4 alkoxy, and C1-4 alkylthio in $R^9$ may be substituted with a halogen atom,
A represents C1-5 alkylene, C2-5 alkenylene, C2-5 alkynylene, —(C1-3 alkylene)-$G^1$-(C1-3 alkylene)-, -$G^1$-(C1-5 alkylene)-, —(C1-3 alkylene)-(5- to 6-membered aromatic ring)-, or -$G^1$-(5- to 6-membered aromatic ring)-,
$G^1$ represents —O—, —S—, or —$NR^{10}$—,
$R^{10}$ represents a hydrogen atom, C1-4 alkyl, or C2-5 acyl,
A may be substituted with 1 to 5 substituents which may be the same as or different from each other, and the substituent is selected from a halogen atom or C1-4 alkyl,
X is $CR^{2-2}$, or N, wherein each X may be the same as or different from each other,
$R^{2-2}$ represents a hydrogen atom or $R^2$, wherein a plurality of $R^{2-2}$s may be the same as or different from each other, respectively,
$R^{2-0}$ represents $R^2$,
$R^2$ represents a halogen atom, nitro, cyano, a hydroxyl group, mercapto (—SH), carboxyl, C1-4 alkyl, C2-4 alkenyl, C2-4 alkynyl, C1-4 alkoxy, C1-4 alkylthio, —$C(O)R^{101}$, —$SO_2R^{102}$, —$CONR^{103}R^{104}$, —$NR^{105}C(O)R^{106}$, —$NR^{107}SO_2R^{108}$, —$SO_2NR^{109}R^{110}$, —$NR^{111}R^{112}$, or -$L^3$-$R^{11}$, wherein $R^{101}$, $R^{102}$, $R^{103}$, $R^{104}$, $R^{105}$, $R^{106}$, $R^{107}$, $R^{108}$, $R^{109}$, $R^{110}$, $R^{111}$, and $R^{112}$ each independently represent a hydrogen atom, C1-4 alkyl, C2-4 alkenyl, C2-4 alkynyl, a C3-10 carbon ring, or a 3- to 10-membered heterocycle, and wherein C1-4 alkyl, C2-4 alkenyl, C2-4 alkynyl, C1-4 alkoxy, C1-4 alkylthio, a C3-10 carbon ring, and a 3- to 10-membered heterocycle in $R^2$, $R^{101}$, $R^{102}$, $R^{103}$, $R^{104}$, $R^{105}$, $R^{106}$, $R^{107}$, $R^{108}$, $R^{109}$, $R^{110}$, $R^{111}$, and $R^{112}$ each independently may be substituted with a halogen atom, a hydroxyl group, cyano, C1-4 alkyl, C1-4 alkoxy, C1-4 alkylthio, —$NR^{113}R^{114}$, a C3-10 carbon ring, -$G^2$-(C3-10 carbon ring), a 3- to 10-membered heterocycle, or a -$G^2$-(3- to 10-membered heterocycle), $G^2$ represents —$CH_2$—, —O—, —S—, or —$NR^{115}$—, wherein $R^{113}$, $R^{114}$, and $R^{115}$ each independently represent a hydrogen atom, C1-4 alkyl, or C2-5 acyl,
$L^3$ represents a bond, —$CR^{12}R^{13}$—, —O—, —$CR^{14}(OR^{15})$—, —C(O)—, —$NR^{16}$—, —$CR^{17}R^{18}O$—, —$CR^{19}R^{20}NR^{21}$—, —$CR^{22}R^{23}NR^{24}CO$—, —$C(O)NR^{25}$—, or —$S(O)_s$—,
s represents an integer of 0 to 2,
$R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ each independently represent a hydrogen atom, or C1-4 alkyl,
$R^{11}$ represents a C3-10 carbon ring or a 3- to 10-membered heterocycle optionally substituted with 1 to 5 $R^{26}$s,
$R^{26}$ represents a halogen atom, a hydroxyl group, a mercapto, oxo, thioxo, —$NR^{27}R^{28}$, nitro, cyano, carboxyl, C1-4 alkyl, C2-4 alkenyl, C2-4 alkynyl, C1-4 alkoxy, C1-4 alkylthio, C2-5 acyl, —$SO_2NR^{29}R^{30}$, a C3-10 carbon ring, a -$G^3$-(C3-10 carbon ring), 3- to a 10-membered heterocycle, or a -$G^3$-(3- to 10-membered heterocycle),
$G^3$ represents —$CH_2$—, —O—, —S—, or —$NR^{31}$—,
$R^{27}$, $R^{28}$, $R^{29}$, $R^{30}$, and $R^{31}$ each independently represent a hydrogen atom, C1-4 alkyl, or C2-5 acyl, wherein C1-4 alkyl, C2-4 alkenyl, C2-4 alkynyl, C1-4 alkoxy, C1-4 alkylthio, C2-5 acyl, a C3-10 carbon ring, a -$G^3$-(C3-10 carbon ring), a 3- to 10-membered heterocycle, or a -$G^3$-(3- to 10-membered heterocycle) in $R^{26}$, $R^{27}$, $R^{28}$, $R^{29}$, $R^{30}$, and $R^{31}$ may be substituted with a halogen atom, and wherein, when a plurality of $R^{26}$'s are present, they may be the same as or different from each other, respectively,
$L^1$ represents —NHCO—,
$R^{35}$ and $R^{36}$ each independently represent a hydrogen atom or C1-4 alkyl, wherein C1-4 alkyl in $R^{35}$ and $R^{36}$ may be substituted with a halogen atom or a hydroxyl group, and wherein
$R^{35}$ and $R^{36}$ may be bonded to each other to form a C3-8 saturated carbon ring,
ring $C^1$ represents a bicyclic C9-10 aromatic carbon ring or a bicyclic 9- to 10-membered aromatic heterocycle,
$R^3$ represents a halogen atom, nitro, cyano, a hydroxyl group, mercapto, oxo, thioxo, carboxyl, C1-4 alkyl, C2-4 alkenyl, C2-4 alkynyl, C1-4 alkoxy, C1-4 alkylthio, a C3-8 saturated carbon ring, a 3- to 8-membered saturated heterocycle, —$C(O)R^{201}$, —$SO_2R^{202}$, —$CONR^{203}R^{204}$, —$NR^{205}C(O)R^{206}$, —$NR^{207}SO_2R^{208}$, —$SO_2NR^{209}R^{210}$, or —$NR^{211}R^{212}$, wherein C1-4 alkyl, C2-4 alkenyl, C2-4 alkynyl, C1-4 alkoxy, C1-4 alkylthio, a C3-8 saturated carbon ring, and a 3- to 8-membered saturated heterocycle in $R^3$, each independently may be substituted with a halogen atom, a hydroxyl group, cyano, C1-4 alkyl, C1-4 alkoxy, C1-4 alkylthio, —$NR^{37}R^{38}$, a C3-10 carbon ring, a -$G^4$-(C3-10 carbon ring), a 3- to 10-membered heterocycle, or a -$G^4$-(3- to 10-membered heterocycle),
$R^{201}$, $R^{202}$, $R^{203}$, $R^{204}$, $R^{205}$, $R^{206}$, $R^{207}$, $R^{208}$, $R^{209}$, $R^{210}$, $R^{211}$, and $R^{212}$, each independently represent a hydrogen atom, C1-4 alkyl, C2-4 alkenyl, C2-4 alkynyl, a C3-10 carbon ring, or a 3- to 10-membered heterocycle, wherein C1-4 alkyl, C2-4 alkenyl, C2-4 alkynyl, a C3-10 carbon ring, and a 3- to 10-membered heterocycle in $R^{201}$, $R^{202}$, $R^{203}$, $R^{204}$, $R^{205}$, $R^{206}$, $R^{207}$, $R^{208}$, $R^{209}$, $R^{210}$, $R^{211}$, and $R^{212}$, each independently may be substituted with a halogen atom, a hydroxyl group, cyano, C1-4 alkyl, C1-4 alkoxy, C1-4 alkylthio, —$NR^{37}R^{38}$, a C3-10 carbon ring, a -$G^4$-(C3-10 carbon ring), a 3- to 10-membered heterocycle, or a -$G^4$-(3- to 10-membered heterocycle), $G^4$ represents —$CH_2$—, —O—, —S—, or —$NR^{115}$—, $R^{37}$ and $R^{38}$ each independently represent a hydrogen atom, C1-4 alkyl or C2-5 acyl, n represents an integer of 0 to 5, when n is two or more, a plurality of $R^3$'s may be the same as or different from each other, $R^{4-1}$ represents —$CONR^{41}R^{42}$ or —$C(O)R^{45-1}$, $R^{41}$ and $R^{42}$ each independently represent a hydrogen atom, C1-6 alkyl, C2-6 alkenyl, C2-6 alkynyl, a C3-10 carbon ring, or a 3- to 10-membered heterocycle, wherein C1-6 alkyl, C2-6 alkenyl, C2-6 alkynyl, a C3-10 carbon ring, and a 3- to 10-membered heterocycle in $R^{41}$ and $R^{42}$ may be substituted with 1 to 6 $R^{50}$s, $R^{50}$ represents a halogen atom, a hydroxyl group, oxo, thioxo, cyano, nitro, —$NR^{51}R^{52}$, C1-6 alkoxy, C1-6 alkylthio, C3-10 carbon ring, -$G^6$-(C3-10 carbon ring), a 3- to 10-membered heterocycle, or a -$G^6$-(3- to 10-membered heterocycle), wherein, when two or more $R^{50}$ are present, $R^{50}$s may be the same as or different from each other, $G^6$ represents —$CH_2$—, —O—, —S—, or —$NR^{53}$—, $R^{51}$, $R^{52}$ and $R^{53}$, each independently represent a hydrogen atom, C1-4 alkyl or C2-5 acyl, $R^{41}$ and $R^{42}$ may form a 3- to 8-membered saturated heterocycle together with nitrogen atoms bonded thereto, and $R^{45-1}$ represents C1-6 alkyl, C2-6 alkenyl, C2-6 alkynyl.

2. The compound according to claim 1, or a pharmaceutically acceptable salt thereof, wherein the ring $C^1$ is indole.

3. The compound according to claim 1, or a pharmaceutically acceptable salt thereof, wherein the ring represented by the formula:

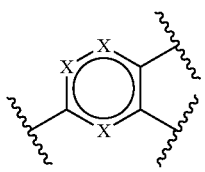

is benzene, pyridine, pyrazine, pyrimidine, or pyridazine.

4. The compound according to claim 1, or a pharmaceutically acceptable salt thereof, wherein the compound of formula (I-0) is represented by formula (I-1):

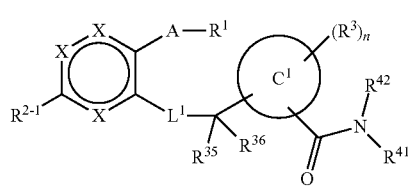

(I-1)

wherein in the formula, $R^{2-1}$ represents a halogen atom, cyano, or -$L^3$-$R^{11}$, and $R^3$, $R^{11}$, and other symbols have the same meanings as defined in claim 1.

5. The compound according to claim 1, or a pharmaceutically acceptable salt thereof, wherein $R^{41}$ is methyl, ethyl, propyl, isopropyl, t-butyl, cyclopropyl, cyclobutyl, cyclopentyl, cyclohexyl, cyclopropylmethyl, benzyl, methoxyethyl, cyclopentyloxyethyl, or phenoxyethyl.

6. The compound according to claim 1, or a pharmaceutically acceptable salt thereof, wherein $R^{50}$ is (1) a hydroxyl group, (2) oxo, (3) thioxo, (4) cyano, (5) nitro, (6) —$NR^{51}R^{52}$, (7) C1-6 alkoxy, (8) C1-6 alkylthio, (9) -$G^6$-(C3-10 carbon ring), (10) a 3- to 10-membered heterocycle, and (11) -$G^6$-(3- to 10-membered -(heterocycle), wherein the symbols have the same meanings as defined in claim 1.

7. The compound according to claim 1, which is:

(1) 4-{4-[(3,5-dimethyl-1H-pyrazol-1-yl)methyl]-2-({2-[3-methyl-6-(methylcarbamoyl)-1H-indol-1-yl]propanoyl}amino)phenyl}butanoic acid, (2) 4-[2-({2-[3-methyl-6-(methylcarbamoyl)-1H-indol-1-yl]propanoyl}amino)-4-{[5-methyl-3-(trifluoromethyl)-1H-pyrazol-1-yl]methyl}phenyl]butanoic acid, (3) 4-{2-({2-[6-(ethylcarbamoyl)-3-methyl-1H-indol-1-yl]propanoyl}amino)-4-[(4-methyl-1H-pyrazol-1-yl)methyl]phenyl}butanoic acid, (4) 4-{2-({2-[3-methyl-6-(propylcarbamoyl)-1H-indol-1-yl]propanoyl}amino)-4-[(4-methyl-1H-pyrazol-1-yl)methyl]phenyl}butanoic acid, (5) 4-{2-({2-[6-(isopropylcarbamoyl)-3-methyl-1H-indol-1-yl]propanoyl}amino)-4-[(4-methyl-1H-pyrazol-1-yl)methyl]phenyl}butanoic acid, (6) 4-{2-[(2-{6-[(2-methoxyethyl)carbamoyl]-3-methyl-1H-indol-1-yl}propanoyl)amino]-4-[(4-methyl-1H-pyrazol-1-yl)methyl]phenyl}butanoic acid, (7) 4-{2-({2-[(6-(dimethylcarbamoyl)-3-methyl-1H-indol-1-yl]propanoyl}amino)-4-[(4-methyl-1H-pyrazol-1-yl)methyl]phenyl}butanoic acid, (8) 4-{2-[(2-{6-[(cyclopropylmethyl)carbamoyl]-3-methyl-1H-indol-1-yl}propanoyl)amino]-4-[(4-methyl-1H-pyrazol-1-yl)methyl]phenyl}butanoic acid, (9) 4-{4-[(3-cyclopropyl-1H-1,2,4-triazol-1-yl)methyl]-2-({2-[3-methyl-6-(methylcarbamoyl)-1H-indol-1-yl]propanoyl}amino)phenyl}butanoic acid,

(10) 4-{4-[(4-fluoro-1H-pyrazol-1-yl)methyl]-2-({2-[3-methyl-6-(methylcarbamoyl)-1H-indol-1-yl]propanoyl}amino)phenyl}butanoic acid,

(11) 4-{4-[(4-isopropyl-1H-1,2,3-triazol-1-yl)methyl]-2-({2-[3-methyl-6-(methylcarbamoyl)-1H-indol-1-yl]propanoyl}amino)phenyl}butanoic acid,

(12) 4-(2-[(2-{6-[(2-methoxyethyl)carbamoyl]-3-methyl-1H-indol-1-yl}propanoyl)amino]-4-{[3-(trifluoromethyl)-1H-1,2,4-triazol-1-yl]methyl}phenyl)butanoic acid,

(13) 4-[2-({2-[3-methyl-6-(methylcarbamoyl)-1H-indol-1-yl]propanoyl}amino)-4-{[3-(trifluoromethyl)-1H-1,2,4-triazol-1-yl]methyl}phenyl]butanoic acid,

(14) 4-{2-({2-[3-methyl-5-(methylcarbamoyl)-1H-indol-1-yl]propanoyl}amino)-4-[(4-methyl-1H-pyrazol-1-yl)methyl]phenyl}butanoic acid,

(15) 4-{2-({2-[5-(isopropylcarbamoyl)-3-methyl-1H-indol-1-yl]propanoyl}amino)-4-[(4-methyl-1H-pyrazol-1-yl)methyl]phenyl}butanoic acid,

(16) 4-{2-[(2-{5-[(2-methoxyethyl)carbamoyl]-3-methyl-1H-indol-1-yl}propanoyl)amino]-4-[(4-methyl-1H-pyrazol-1-yl)methyl]phenyl}butanoic acid,

(17) 4-{2-({2-[3-cyclopropyl-6-(methylcarbamoyl)-1H-indol-1-yl]propanoyl}amino)-4-[(4-methyl-1H-pyrazol-1-yl)methyl]phenyl}butanoic acid,

(18) 4-{2-[(2-{3-cyclopropyl-6-[(2-methoxyethyl)carbamoyl]-1H-indol-1-yl}propanoyl)amino]-4-[(4-methyl-1H-pyrazol-1-yl)methyl]phenyl}butanoic acid,

(19) 4-{4-cyano-2-[(2-{6-[(2-methoxyethyl)carbamoyl]-1H-indol-1-yl}propanoyl)amino]phenyl}butanoic acid,

(20) 4-[4-cyano-2-({2-[6-(ethylcarbamoyl)-3-methyl-1H-indol-1-yl]propanoyl}amino)phenyl]butanoic acid,

(21) 4-[4-cyano-2-({2-[3-methyl-6-(methylcarbamoyl)-1H-indol-1-yl]propanoyl}amino)phenyl]butanoic acid,

(22) 4-{4-cyano-2-[(2-{3-methyl-6-[(2-methyl-2-propanyl)carbamoyl]-1H-indol-1-yl}propanoyl)amino]phenyl}butanoic acid,

(23) 4-{4-cyano-2-[(2-{6-([2-methoxyethyl)carbamoyl]-3-methyl-1H-indol-1-yl}propanoyl)amino]phenyl}butanoic acid,

(24) 4-[4-cyano-2-({2-[3-cyclopropyl-6-(methylcarbamoyl)-1H-indol-1-yl]propanoyl}amino)phenyl]butanoic acid,

(25) 4-{4-cyano-2-[(2-{3-cyclopropyl-6-[(2-methoxyethyl)carbamoyl]-1H-indol-1-yl}propanoyl)amino]phenyl}butanoic acid,

(26) 4-{2-({2-[3-methyl-6-(methylcarbamoyl)-1H-indol-1-yl]propanoyl}amino)-4-[(4-methyl-1H-pyrazol-1-yl)methyl]phenyl}butanoic acid,

(27) 4-[2-({2-[3-methyl-6-(methylcarbamoyl)-1H-indol-1-yl]propanoyl}amino)-4-phenoxyphenyl]butanoic acid, or

(28) 4-[2-({2-[3-methyl-6-(methylcarbamoyl)-1H-indol-1-yl]propanoyl}amino)-4-(5-methyl-1,3,4-oxadiazol-2-yl)phenyl]butanoic acid, or a pharmaceutically acceptable salt thereof.

8. A pharmaceutical composition comprising (a) the compound of formula (I-0) according to claim 1, or a pharmaceutically acceptable salt thereof as an active ingredient and (b) a pharmaceutically acceptable carrier.

9. The pharmaceutical composition according to claim 8, which is an $EP_4$ receptor antagonist.

10. A medicament comprising a combination of a compound of formula (I-0) according to claim 1, or a pharmaceutically acceptable salt thereof, and at least one or more agents selected from an alkylating agent, an antimetabolite, an anticancer antibiotic, a plant-based preparation, a hormone, a platinum compound a topoisomerase inhibitor a kinase inhibitor, an anti-CD 20 antibody, an anti-HER2 antibody, an anti-EGFR antibody, an anti-VEGF antibody, a proteasome inhibitor, a HDAC inhibitor, an immune checkpoint inhibitor, and an immunomodulator.

11. A method for treating a disease caused by activation of an $EP_4$ receptor, the method comprising: administering to a patient in need thereof an effective amount of compound of formula (I-0) according to claim 1, or a pharmaceutically acceptable salt thereof, wherein the disease caused by activation of an EP4 receptor is cancer, aneurysm, rheumatoid arthritis, osteoarthritis, ulcerative colitis, Crohn's disease, pain, Alzheimer's, or endometriosis.

12. The method according to claim 11, wherein the cancer is breast cancer, ovarian cancer, large intestine cancer, lung cancer, prostate cancer, head and neck cancer, lymphoma, uveal malignant melanoma, thymoma, mesothelioma, esophageal cancer, stomach cancer, duodenal cancer, hepatocellular cancer, bile duct cancer, gallbladder cancer, pancreatic cancer, renal cell cancer, renal pelvis and ureter cancer, bladder cancer, penile cancer, testicular cancer, uterine cancer, vaginal cancer, vulvar cancer, skin cancer, malignant bone tumor, soft tissue sarcoma, chondrosarcoma, leukemia, myelodysplastic syndrome, or multiple myeloma.

* * * * *

UNITED STATES PATENT AND TRADEMARK OFFICE
CERTIFICATE OF CORRECTION

PATENT NO. : 11,479,550 B2
APPLICATION NO. : 16/614877
DATED : October 25, 2022
INVENTOR(S) : Masaki Asada, Kousuke Tani and Satonori Higuchi It is certified that error appears in the above-identified patent and that said Letters Patent is hereby corrected as shown below:

In the Claims

In Claim 4, Column 127, Line 66, delete "$R^3$," and insert --$L^3$,-- therefor;

In Claim 6, Column 128, Line 12, delete "-(heterocycle)," and insert --heterocycle),-- therefor;

In Claim 7, Column 128, Line 41, delete "4-{2-({2-[(6-" and insert --4-{2-({2-[6- -- therefor;

In Claim 7, Column 129, Line 35, delete "4-{4-cyano-2-[(2-{6-([2-" and insert --4-{4-cyano-2-[(2-{6-[(2- -- therefor; and In Claim 11, Column 130, Line 32, delete "EP4" and insert --$EP_4$-- therefor.

Signed and Sealed this
Tenth Day of January, 2023

Katherine Kelly Vidal
*Director of the United States Patent and Trademark Office*